US011185581B2

(12) United States Patent
Jiang et al.

(10) Patent No.: US 11,185,581 B2
(45) Date of Patent: Nov. 30, 2021

(54) HUMAN ROTAVIRUS G9P[6] STRAIN AND USE AS A VACCINE

(71) Applicant: THE UNITED STATES OF AMERICA, AS REPRESENTED BY THE SECRETARY, DEPARTMENT OF HEALTH AND HUMAN SERVICES, Bethesda, MD (US)

(72) Inventors: Baoming Jiang, Duluth, GA (US); Yuhuan Wang, Liburn, GA (US)

(73) Assignee: The United States of America as represented by the Secretary, Department of Health and Human Services, Bethesda, MD (US)

( * ) Notice: Subject to any disclaimer, the term of this patent is extended or adjusted under 35 U.S.C. 154(b) by 48 days.

(21) Appl. No.: 16/717,946

(22) Filed: Dec. 17, 2019

(65) Prior Publication Data

US 2020/0121781 A1 Apr. 23, 2020

Related U.S. Application Data

(62) Division of application No. 15/765,716, filed as application No. PCT/US2016/054211 on Sep. 28, 2016, now Pat. No. 10,548,970.

(60) Provisional application No. 62/237,452, filed on Oct. 5, 2015.

(51) Int. Cl.

| | |
|---|---|
| ***A61K 39/15*** | (2006.01) |
| ***C12N 7/00*** | (2006.01) |
| ***A61P 31/14*** | (2006.01) |
| ***A61K 9/00*** | (2006.01) |
| ***A61K 39/39*** | (2006.01) |
| *A61K 39/00* | (2006.01) |

(52) U.S. Cl.

CPC ............ *A61K 39/15* (2013.01); *A61K 9/0053* (2013.01); *A61K 39/39* (2013.01); *A61P 31/14* (2018.01); *C12N 7/00* (2013.01); *A61K 2039/5252* (2013.01); *A61K 2039/5254* (2013.01); *A61K 2039/54* (2013.01); *A61K 2039/55505* (2013.01); *C12N 2720/12021* (2013.01); *C12N 2720/12034* (2013.01); *C12N 2720/12043* (2013.01)

(58) Field of Classification Search

CPC ............ A61K 2039/5258; A61K 39/12; A61K 39/15; A61P 31/14; C12N 2720/12334; C12N 15/8258

See application file for complete search history.

(56) References Cited

U.S. PATENT DOCUMENTS

| | | | |
|---|---|---|---|
| 6,290,968 B1 | 9/2001 | Clark et al. | |
| 7,150,984 B2 | 12/2006 | Hoshino et al. | |
| 7,579,008 B2 | 8/2009 | Colau et al. | |
| 8,192,747 B2 | 6/2012 | Velde | |
| 8,822,192 B2 | 9/2014 | Jiang et al. | |
| 9,169,296 B2 | 10/2015 | Jiang | |
| 2003/0016613 A1 | 9/2003 | Choi et al. | |
| 2009/0028828 A1 | 1/2009 | Colau et al. | |
| 2015/0216961 A1* | 8/2015 | D'Aoust ............. | C07K 14/005 424/186.1 |
| 2018/0028644 A1 | 2/2018 | Jiang et al. | |

FOREIGN PATENT DOCUMENTS

| | | |
|---|---|---|
| WO | WO 2001/012797 A2 | 2/2001 |
| WO | WO 2005/021033 A2 | 3/2005 |
| WO | WO 2006/007555 A2 | 1/2006 |
| WO | WO 2007/020078 | 2/2007 |
| WO | WO 2010/132561 A2 | 11/2010 |

OTHER PUBLICATIONS

Kirkword et al. (Virology, 1999, vol. 256, pp. 45-53).*

Wang et al., "A DS-1 like G9P[6] human strain CDC-6 as a new rotavirus vaccine candidate," *Vaccine* 36(45): 6844-6849 (e-Pub Sep. 24, 2018).

Agbemabiese et al., "Evolution of a G6P[6] rotavirus strain isolated from a child with acute gastroenteritis in Ghana, 2012," *Journal of General Virology* 96: 2219-2231 (2015).

Dennehy, "Rotavirus vaccines: an overview," *Clinical Microbiology Reviews* 21(1): 198-208 (Jan. 2008).

Esona et al., "Molecular characterization of human rotavirus vaccine strain CDC-9 during sequential passages in Vero cells," *Human Vaccines* 6(3): 247-253 (published online Mar. 1, 2010).

International Search Report from PCT Application No. PCT/US2016/054211, 9 pages (dated Jan. 10, 2017).

Iturriza-Gómara et al., "Reassortment in Vivo: Driving force for Diversity of human rotavirus strains isolated in the United Kingdom between 1995 and 1999," *Journal of Virology* 75(8): 3696-3705 (Apr. 15, 2001).

Koch et al., "Halting progressive neurodegeneration in advanced retinitis pigmentosa," *Journal of Clinical Investigation* 125(9): 3704-3713 (Sep. 2015).

Mukherjee et al., "Full genomic analysis of a human group A rotavirus G9P[6] strain from Eastern India provides evidence for porcine-to-human interspecies transmission," *Arch Virol* 154(5): 733-746 (Mar. 31, 2009).

Patton, "Rotavirus diversity and evolution in the post-vaccine world," *Discovery Medicine* 13: 85-97 (Jan. 2012).

(Continued)

*Primary Examiner* — Bao Q Li

(74) *Attorney, Agent, or Firm* — Klarquist Sparkman, LLP

(57) ABSTRACT

Attenuated G9P[6] rotavirus is disclosed herein. In some embodiments, pharmaceutical compositions are disclosed that include an attenuated G9P[6] rotavirus, or a component thereof. These compositions can be used to induce an immune response, such as a protective immune response, to a rotavirus. The compositions can be used as vaccines, such as for children (infants), for example in a prime boost strategy.

19 Claims, 4 Drawing Sheets

Specification includes a Sequence Listing.

(56) References Cited

OTHER PUBLICATIONS

Rahman et al., "Genetic characterization of a novel, naturally occurring recombinant human G6P[6] rotavirus," *Journal of Clinical Microbiology* 41(5): 2088-2095 (May 2003).

Ramachandran et al., "Detection and characterization of novel rotavirus strains in the United States," *Journal of Clinical Microbiology* 36(11): 3223-3229 (Nov. 1, 1998).

Ramachandran et al., "Unusual diversity of human rotavirus G and P genotypes in India," *Journal of Clinical Microbiology* 34(2): 436-439 (Feb. 1, 1996).

Reesu et al., "Emergence of an Unusual Genotype of Rotavirus in Andaman and Nicobar Islands, India," *Intervirology* 56:134-139 (published online Dec. 28, 2012).

Ruiz-Palacios et al. "Safety and efficacy of an attenuated vaccine against severe rotavirus gastroenteritis," *New England Journal of Medicine* 354(1): 11-22 (2006).

Tsugawa et al., "Virulence-associated genome mutations of murine rotavirus identified by alternating serial passages in mice and cell cultures," *Journal of Virology* 88(10): 5543-5558 (May 2014).

Written Opinion from PCT Application No. PCT/US2016/054211, 11 pages (dated Jan. 10, 2017).

Yamamoto et al., "Detection and full genomic analysis of G[6]P9 human rotavirus in Japan," *Virus Genes* 43: 215-223 (2011)(abstract only).

Zeller et al., "Full genome characterization of a porcine-like human G9P[6] rotavirus strain isolated from an infant in Belgium," *Infection, Genetics and Evolution* 12: 1492-1500 (e-Pub Mar. 10, 2012).

* cited by examiner

Purification of TLPs

CDC-6

Wa stool p41 DS-1

RNA electropherotype

FIG. 3

| CDC-6 NT & AA sequence changes from stool to p41 | | | |
|---|---|---|---|
| Gene Segment | Length (nt) | NT changes (position) | AA changes (position) |
| VP1 | 3302 | T→G (2725) | L→V (903) |
| VP2 | 2684 | NC | NC |
| VP3 | 2591 | NC | NC |
| VP4 | 2359 | A→G (806); A→C (1171) | Y→C (266); I→L (388) |
| VP6 | 1356 | NC | NC |
| VP7 | 1061 | G→A (493) | E→K (149) |
| NSP1 | 1566 | T→C (345) | L→S (112) |
| NSP2 | 1059 | NC | NC |
| NSP3 | 1066 | NC | NC |
| NSP4 | 687 | T→T/C (645) | NC |
| NSP5 | 816 | NC | NC |

FIG. 4

CDC-6 & GR10924/99 NT and AA identity comparison

| Gene | NT Ident. | Accession | AA Ident. | Accession |
|---|---|---|---|---|
| VP1 | 99.6% | FJ183353.1 | 99.7% | ACJ06213.1 |
| VP2 | 99.4% | FJ183354.1 | 99.9% | ACJ06214.1 |
| VP3 | 99.3% | FJ183355.1 | 99.5% | ACJ06215.1 |
| VP4 | 99.2% | FJ183356.1 | 99.0% | ACJ06216.1 |
| VP6 | 99.6% | FJ183358.1 | 100.0% | ACJ06218.1 |
| VP7 | 99.3% | FJ183360.1 | 98.8% | ACJ06220.1 |
| NSP1 | 99.1% | FJ183357.1 | 98.8% | ACJ06217.1 |
| NSP2 | 99.7% | FJ183361.1 | 100.0% | ACJ06221.1 |
| NSP3 | 99.2% | FJ183359.1 | 98.7% | ACJ06219.1 |
| NSP4 | 99.5% | FJ183363.1 | 100.0% | ACJ06223.1 |
| NSP5 | 99.5% | FJ183362.1 | 99.5% | ACJ06222.1 |

HUMAN ROTAVIRUS G9P[6] STRAIN AND USE AS A VACCINE

CROSS REFERENCE TO RELATED APPLICATION

This is a divisional of U.S. patent application Ser. No. 15/765,716, filed Apr. 3, 2018, which is a § 371 U.S. national stage of International Application No. PCT/US2016/054211, filed Sep. 28, 2016, which was published in English under PCT Article 21(2), which claims the benefit of U.S. Provisional Application No. 62/237,452, filed Oct. 5, 2015. The prior applications are all incorporated by reference in their entirety.

FIELD OF THE DISCLOSURE

This relates to the field of virology, specifically to methods for inducing an immune response to a rotaviral infection using an attenuated G9P[6] rotavirus.

BACKGROUND

Rotavirus is the most common cause of diarrhea in children; nearly every child in the world has been infected with a rotavirus by the age of five. The virus is believed to be highly contagious by the fecal-oral route, and affects no particular socioeconomic or geographic group disproportionately. While the majority of children survive infection, a large number of children become severely ill, and the number of deaths associated with the virus is considerable. In addition to its impact on human health, rotavirus also infects animals, and is a pathogen of livestock.

Rotavirus A accounts for more than 90% of rotavirus gastroenteritis in humans. Rotavirus A is an icosahedral virus in the family Reoviridae with a distinct hub-and-spoke morphology. Rotavirus particles contain three protein layers surrounding the viral genome which consists of 11 segments of double-stranded RNA, each segment encoding a protein. There are six viral proteins (VPs) that form the virus particle, called VP1-VP7, and six nonstructural proteins (NSPs), called NSP1-NSP6. Rotaviruses are classified by group, subgroup and serotype according to properties characteristic of the viral capsid proteins.

A number of the structural proteins are particularly important in eliciting an immune response in a host since these proteins are present on the outermost surface of the viral particles. It is believed that VP7 and VP4 play an important role in the host immune response. Variants of VP7 and VP4 structural proteins characterize distinct rotavirus A serotypes. In particular, variants of human VP7 are identified as "G" serotypes including at least serotypes G1, G2, G3, G4, G5, G6, G8, G9, G10, G11, G12, G13 and G14. Variants of the VP4 structural protein are identified as "P" serotypes including P1A, P1B, P2A, P3, P4, P5, P6 and P8. Because intact rotaviruses are characterized by both a VP7 protein and a VP4 protein, individual virus serotypes are named according to the identity of the variant of these two proteins contained in the particular virus. The G1 serotype of rotavirus A is the most common serotype associated with human disease worldwide. A common rotavirus A contains both G1 and P[8] variants of VP7 and VP4, and is called G1P[8]. A number of vaccines have been developed which use rotavirus A G1 strains with the goal of developing immunity in a host against rotavirus A G1 strains as well as rotavirus A strains having other serotypes.

A diversity of human rotavirus types is increasingly recognized as contributing to acute severe diarrhea disease worldwide. This diversity underscores the need for robust vaccines capable of generating immunity against several strains. ROTARIX® is a vaccine that has broad cross-reactive immunity and cross protection against homotypic Wa-like and heterotypic DS-1 like strains among children worldwide. However, this vaccine confers lower efficacy against DS-1 like strains in some regions. Thus, there is a continuing need for vaccines against human rotavirus A of both common and less common types.

SUMMARY OF THE DISCLOSURE

An attenuated G9P[6] rotavirus is disclosed herein. In some embodiments, pharmaceutical compositions are disclosed that include an attenuated G9P[6] rotavirus. Optionally, the pharmaceutical compositions can include an adjuvant and/or an inactivated G1P[8] rotavirus. In additional embodiments, methods are also disclosed for inducing an immune response in a subject, by administering to the subject a pharmaceutical composition including an attenuated G9P[6] rotavirus. In some non-limiting examples, the pharmaceutical composition is administered orally and does not include an adjuvant. In other non-limiting examples, the composition is administered parentally, and includes an adjuvant. Optionally, the G9P[6] rotavirus is inactivated. Optionally, the pharmaceutical compositions can include an inactivated G1P[8] rotavirus. In a specific non-limiting example, the G1P[8] rotavirus is CDC-9. The G1P[8] rotavirus can be attenuated and/or inactivated.

The inactivated attenuated rotavirus can also be included in pharmaceutical compositions to induce a response to other pathogens, such as, but not limited to, diphtheria, tetanus, pertussis, *Haemophilus influenzae* type b, hepatitis B (HBV), polio and/or pneumococcal disease.

The immune response can be a protective immune response. The subject can be a child, such as a human child of less than 5 years of age or 1 year of age. The method can include at least one prime and boost.

In further embodiments, isolated nucleic acid molecules from the G9P[6] and isolated polypeptides from the G9P[6] rotavirus are disclosed. These molecules can be included in pharmaceutical compositions and can be used to induce an immune response.

The foregoing and other features and advantages of the invention will become more apparent from the following detailed description of several embodiments which proceeds with reference to the accompanying figures.

BRIEF DESCRIPTION OF THE FIGURES

FIG. 3 is a table showing the nucleotide and amino acid sequence changes that occurred in the attenuated form of the virus.

FIG. 4 is a table showing the sequence identity between CDC-6 and GR10924, a virulent G9P[6] rotavirus, for each nucleotide and protein sequence.

SEQUENCE LISTING

Figure 1:
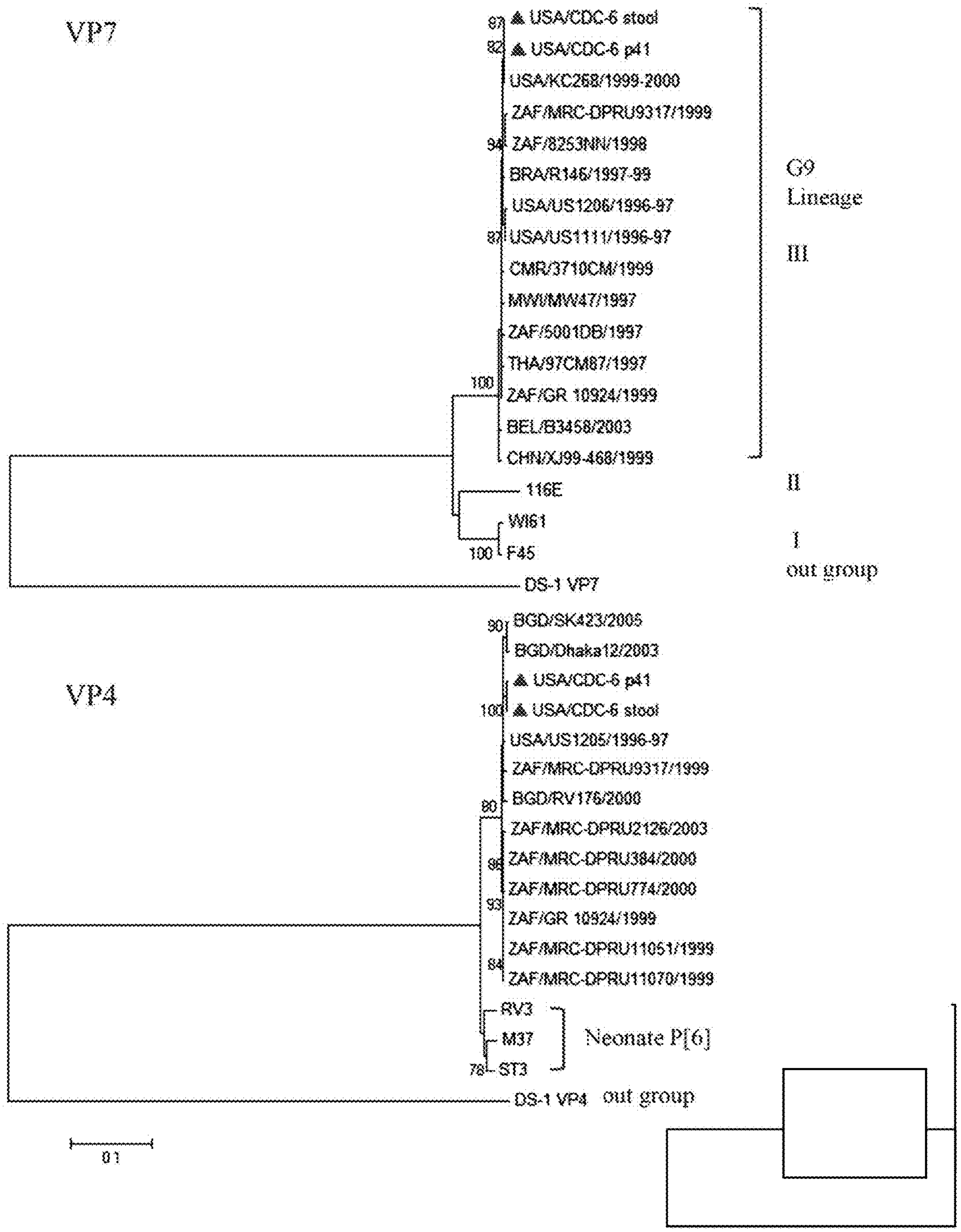
FIG. 1 shows the relationship of the VP4 and VP7 sequences to other rotaviruses.
Figure 2:
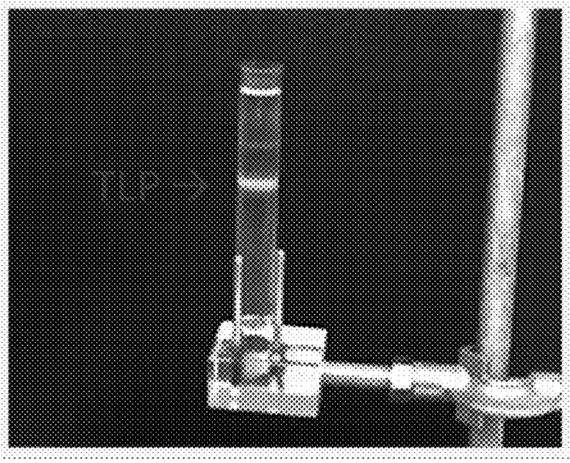
FIG. 2 are digital images showing the purification of TLPs and the RNA eleptropherotype.
Figure 2:
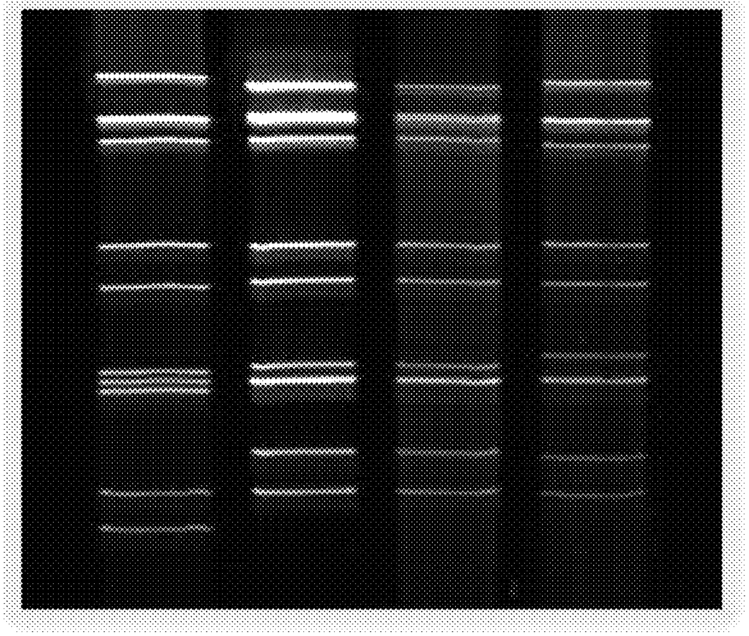

The nucleic and amino acid sequences listed are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file [Sequence_Listing, Dec. 16, 2019, 74.1 KB], which is incorporated by reference herein. In the accompanying sequence listing:

SEQ ID NO: 1 is an amino acid sequence of a VP1 polypeptide from an attenuated G9P[6] rotavirus:

MGKYNLILSEYLSFIYNSQSAVQIPIYYSSNSELESRCIEFHSKCLENSKNGLSLKKLFNEYSDVIENATLLSILSY
SYDKYNAVERKLVKYAKGKPLEADLTVNELDYENNKITSELFPTAEEYTDSLMDPAILTSLSSNLNAVMFWL
EKHENDTAEKFKIYKRRLDLFTIVASTVNKYGVPRHNAKYRYEYDVMKDKPYYLVTWANSSIEMLMSVFSH
EDYLIARELIVLSYSNRSTLAKLVSSPMSILVALVDINGTFITNEELELEFSNKYVRAIVPDQTFDELKQMLNSM
RKAGLVDIPKMIQDWLVDCSIEKFPLMAKIYSWSFHVGFRKQKMLDAALDQLKTEYTEDVDDEMYREYTML
IRDEVVKMLEESVKHDDHLLQDSELAGLLSMSSASNGESRQLKFGRKTVFSTKKNMHVMDDMANGRYTPGII
PPVNADKPIPLGRRDVPGRRTRIIFILPYEYFIAQHAVVEKMLIYAKHTREYAEFYSQSNQLLSYGDVTRFLSNN
AMVLYTDVSQWDSSQHNTQPFRKGIIMGLDILANMTNDAKVIQTLNLYKQTQINLMDSYVQIPDGNVIKKIQ
YGAVASGEKQTKAANSIANLALIKTVLSRISNKYSFATKIIRVDGDDNYAVLQFNlEVTKQMVQDVSNDVRET
YARMNAKVKALVSTVGIEIAKRYIAGGKIFFRAGINLLNNEKRGQSTQWDQAAVLYSNYIVNRLRGFETDREF
ILTKIMQMTSVAITGSLRLFPSERVLTTNSTFKVFDSEDFIIEYGTTDDEVYIQRAFMSLSSQRSGIADEIAASPTF
KNYVSRLSEQLLFSKNNIVSRGIALlEKAKLNSYAPISLEKRRAQISALLTMLQKPVTFKSNKITINDILKDIKPF
FTVSEAHLPIQYQKFMPTVPENVQYIIQCIGSRTYQIEDDGSKSAISRLISKYSVYKPSIEELYKVISLHENEIQLY
LISLGIPKIDADTYVGSKIYSQDKYRILESYVYNLLSINYGCYQLFDFNSPDLEKLIRIPFKGKIPAVTFILHLYAK
LEVINHAIKNGSWISLFCNYPKSEMIKLWKKMWNITSLRSPYTNANFFQD

SEQ ID NO: 2 is an amino acid sequence of a VP2 polypeptide from an attenuated G9P[6] rotavirus:

MAYRKRGARREANLNNNDRMQEKIDEKQDSNKIQLSDKVLSKKEEIVTDSHEEVKVTDELKKSTKEESKQLL
EVLKTKEEHQKEIQYEILQKTIPTFEPKETILRKLEDIKPELAKKQTKLFRIFEPKQLPIYRANGERELRNRWYW
KLKKDTLPDGDYDVREYFLNLYDQVLlEMPDYLLLKDMAVENKNSRDAGKVVDSETASICDAIFQDEETEG
AVRRFIAEMRQRVQADRNVVNYPSILHPIDYAFNEYFLQHQLVEPLNNDITNYIPERIRNDVNYILNMDRNLPS
TARYIRPNLLQDRLNLHDNFESLWDTITTSNYILARSVVPDLKELVSTEAQIQKMSQDLQLEALTIQSETQFLTG
INSQAANDCFKTLIAAMLSQRTMSLDFVTTNYMSLISGMWLLTVVPNDMFIRESLVACQLAIVNTIIYPAFGM
QRMHYRNGDPQTPFQIAEQQIQNFQVANWLHFVNNNQFRQAVIDGVLNQVLNDNIRNGHVINQLMEALMQL
SRQQFPTMPIDYKRSIQRGILLLSNRLGQLVDLTRLLAYNYETLMACITMNMQHVQTLTTEKLQLTSVTSLCM
LIGNATVIPSPQTLFHYYNVNVNFHSNYNERINDAVAIITAANRLNLYQKKMKAIVEDFLKRLYIFDVSRVPDD
QMYRLRDRLRLLPVEIRRLDIFNLILMNMDQIERASDKIAQGVIIAYRDMHLERDEMYGYVNIARNLEGFQQIN
LEELMRSGDYAQVINMLLNNQPVALVGALPFITDSSVISLIAKLDATVFAQIVKLRKVDTLKPILYKINSDSNDF
YLVANYDWVPTSTTKVYKQVPQQFDFRNSMHMLTSNLTFTVYSDLLAFVSADTVEPINAVAFDNMRIMNEL

SEQ ID NO: 3 is an amino acid sequence of a VP3 polypeptide from an attenuated G9P[6] rotavirus:

MKVLALRHSVAQVYADTQVYTHDDSKDEYENAFLISNLTTHNILYLNYNVKTLQILNKSGIAAVEIQKIDELF
TLIRCNFTYDYIDDVVYLHDYSYYTNNEIRTDQHWITKTNIEDYLLPGWKLTYVGYNGSDTRGHYNFSFRCQ
NAATDDDAIIEYIYSDELDFQSFILKKIKERMTTSLPIARLSNRVFRDKLFKTLSVNHDKVVNIGPRNESMFTFL
DYPSIKQFSNGPYLVKDTIKLKQERWLGKRLSQFDIGQYKNMLNVLTTLYQYYDIYHEKPIVYMIGSAPSYWI
YDVKQYSNLKFETWDPLDTPYSNLHHKELFYMNDVQKLKDNSILYIDIRTDRGTVDWKEWRKIVERQTIDNL
HIAYKYLSTGKAKVCCVKMTAMDLELPISAKLLHHPTlEIRSEFYLVMDIWDSKNIKRFIPKGVLYSYINNTIlE
NVFIQQPFKLKTLKNEYIIALYALSNDFNNREDVVKLINNQKKALMTVRINNTFKDEPKVGFKNIYDWTFLPT
DFETNGSIITSYDGCLGIFGLSISLASKPTGNNHLFILSGTDKYFKLDQFANHMSISRRSHQIRFSESATSYSGYIF
RDLSNNNFNLIGTNIENSVSGHVYNALIYYRYNYSFDLKRWIYLHSTGKASIEGGKYYEHAPIELIYACRSARE
FAKLQDDLTVLRYSNEIENYINKVYSITYADDPNYFIGVKFKNIPYKYNVKVPHLTFGVLNISEQMLPDVITILK
RFKNELFGMEVTTSYTYMLSDEVYVANISGVLSTYFKIYNEFYKEQITFGQSRMFIPHVTLSFSNEKTVRIDTTK
LYIDSIYLRKIKGDTVFDMTG

SEQ ID NO: 4 is an amino acid sequence of a VP4 polypeptide from an attenuated G9P[6] rotavirus:

MASLIYRQLLTNSYTVELSDEINTIGSEKSQNVTINPGPFAQTNYAPVTWSHGEVNDSTTIEPVLDGPYQPTNFK
PPNDYWILLNPTNQQVVLEGTNKIDIWVALLLVEPNVTNQSRQYTLFGETKQITVENNTNKWKFFEMFRSNVS
AEFQHKRTLTSDTKLAGFMKFYNSVWTFRGETPHATTDYSSTSNLSEVETVIHVEFYIIPRSQESKCSEYINTGL
PPMQNTRNIVPVALSSRSVTYQRAQVNEDIIISKTSLWKEMQCNRDIIIRFKFNNSIVKLGGLGYKWSEISFKAA
NYQYSYLRDGEQVTAHTTCSVNGVNNFSYNGGSLPTDFSVSRYEVIKENSYVYVDYWDDSQAFRNMVYVRS
LAANLNSVKCSGGTYNFQLPVGAWPVMSGGAVSLHFAGVTLSTQFTDFVSLNSLRFRFSLTVEEPPFSILRTRV
SGLYGLPAFNPNDGHEYYEIAGRFSLISLVPSNDDYQTPIMNSVTVRQDLERQLGDLREEFNSLSQEIAMTQLID
LALLPLDMFSMFSGIKSTIDVAKSMVTKVMKKFKKSGLATSISELTGSLSNAASSVSRSSSIRSNISSISVWTDVS
EQIAGSSDSVRNISTQTSAISKRLRLREITTQlEGMNFDDISAAVLKTKIDRSTHISPNTLPDIITESSEKFIPKRAY
RVLKDDEVMEADVDGKFFAYKVGTFEEVPFDVDKFVDLVTDSPVISAIIDFKTLKNLNDNYGITRSQALDLIRS
DPRVLRDFINQNNPIIKNRIEQLILQCRL

SEQ ID NO: 5 is an amino acid sequence of a VP6 polypeptide from an attenuated G9P[6] rotavirus:

MDVLYSLSKTLKDARDKIVEGTLYSNVSDLIQQFNQMIITMNGNEFQTGGIGNLPIRNWNFDFGLLGTTLLNL
DANYVETARNTIDYFVDFVDNVCMDEMVRESQRNGIAPQSDSLRKLSGIKFKRINFDNSSEYIENWNLQNRRQ
RTGFTFHKPNIFPYSASFTLNRSQPAHDNLMGTMWLNAGSEIQVAGFDYSCAINAPANTQQFEHIVQLRRVLT
TATITLLPDAERFSFPRVINSADGATTWYFNPVILRPNNVEVEFLLNGQIINTYQARFGTIVARNFDTIRLSFQLM
RPPNMTPSVAALFPNAQPFEHHATVGLTLKIESAVCESVLADASETMLANVTSVRQEYAIPVGPVFPPGMNWT
DLITNYSPSREDNLQRVFTVASIRSMLVK

SEQ ID NO: 6 is an amino acid sequence of a VP7 polypeptide from an attenuated G9P[6] rotavirus:

MYGIEYTTILTFLISIVLLNYILKSLTSAMDFITYRFLLLIVIASPFVKTQNYGINLPITGSMDTAYANSSQQETFLT
STLCLYYPlEASTQIGDlEWKDTLSQLFLTKGWPTGSVYFKEYTDIASFSIDPQLYCDYNVVLMKYDSTLKLD

-continued

MSELADLILNEWLCNPMDITLYYYQQTDEANKWISMGQSCTIKVCPLNTQTLGIGCITTNTATFEEVATNEKL
VITDVVDGVNHKLDVTTNTCTIRNCKKLGPRENVAIIQVGGSDVLDITADPTTAPQTERMMRVNWKKWWQV
FYTVVDYINQIVQVMSKRSRLLNSAAFYYRV

SEQ ID NO: 7 is an amino acid sequence of a NSP1 polypeptide from an attenuated G9P[6] rotavirus:
MATFKDACYQYKKLNKLNNAVLKLGANDVWRPSTLTKRKGWCLDCCQHTDLTYCQGCLIYHVCEWCSQY
SRCFLDNDPHLLRMRTFRNEITKSDLENLINMYDTSFPINQKIVNKFANAIKQHKCRNEYLIQWYNHFLMPITL
QSLSIELDGDIYYIFGYYDDMHKINQTPFSFTNLISKYDVLLLDSINFDRMAFLPLTLQQEYALRYFSKSRFIlER
RKCIEISHFSDNILNDLHNPNFTLQVIRNCSNMSVEWNKACNLIRNISNYFDIFKSSHlESYNISPRCRVFTQYKL
KIASKLIKPNYVASNHNSLATEVHNCKWCSINNNSIVWTDFRIKNVYNDIFNFIRALVKSNLYVGHCSSEEKIY
ESIKDILNVCKENEWNMLVTEIFNQLDPIKLNEDSYVLLNYEINWNVMNVLINSIGKVPKILTLSDVISILRIIIYD
WFDIRFMRNTPMTTFTVNKLKQLYEKDRTAEYDSGVSDVE SEQ ID NO: 8 is an amino acid sequence of a NSP2 polypeptide from an attenuated G9P[6] rotavirus:
MAELACFCYPHLENDSYKFIPFNNLAIKCMLTAKVEKKDQDKFYNSITYGIAPPPQFKKRYNTNDNSRGMNYE
TAMFNKVAVLICEALNSIKVTQSDVASVLSRVVSVRHLENLVLRRENHQDVLFHSKELLLKSVLIAIGHSKEIE
TTATAEGGEIVFQNAAFTMWKLTYLEHKLMPILDQNFIEYKITLNEDKPISESHVKELIAELRWQYNKFAVITH
GKGHYRVVKYSSVANHADRVYATFKSNNKNGGPLEFNLLDQRIIWQNWYAFTSSMKQGNALDVCKKLLFQ
KMKRESNPFKGLSTDRKMDEVSQVGI SEQ ID NO: 9 is an amino acid sequence of a NSP3 polypeptide from an attenuated G9P[6] rotavirus:
MLKMESTQQMASSIINSSFEAAVVAATSTLELMGIQYDYNEVYTRVKSKFDFVMDDSGVKNNLIGKAATIDQ
ALNGKFSSSIRNRNWMTDSKTVARLDEDVNKLRLLLSSKGIDQKMRVLNACFSVKRVPEKSSSIIKCTRLMKE
KIERGEVEVDDTFIEEKMEIDTIDWKSRYDQLERRFESLKQRVNEKYNNWVIKARKINENMNSLQNVISQQQA
HINELQIYNDKLERDLQSKIGSVISSIEWYLRSMELSDDIKSDIEQQLNSIDHINPVNAFDDFESILRNLISDYDRIF
IMIXGLLQQSNYTYTYE SEQ ID NO: 10 is an amino acid sequence of a NSP4 polypeptide from an attenuated G9P
MEKFTDLNYTLSVITLMNSTLHTILEDPGMAYFPYIASVLTVLFTLHKASIPTMKIALKTSKCSYKVVKYCIVTI
LNTLLKLAGYKEQITTKDEIEKQMDRVVKEMRRQLEMIDKLTTREIEQVELLKRIYDKLIVRSTDEIDMTKEIN
QKNVRTLEEWESGKNPYEPKEVTAAM SEQ ID NO: 11 is an amino acid sequence of a NSP5 polypeptide from an attenuated G9P
MSLSIDVNSLPSISSSVYKNESFSTTSTISGKSIGRSEQYISPDAEAFNKYMLSKSPEDIGPSDSASNDPLTSFSIRS
NAVKTNADAGVSMDSSAQSRPSSDIGYDQMDFSLNKGIKIDATMDSSISISTTSKKEKSKQENKNKYKKCYPK
IEAESDSDEYVLDDSDSDDGKCKNCKYKKKYFALRLRMKQVAMQLIKDL SEQ ID NO: 12 is an exemplary nucleic acid sequence encoding a VP1 polypeptide from an attenuated G9P
GGCTATTAAAGCTATACAATGGGGAAGTATAATCTAATCTTGTCAGAATACTTATCATTT
ATATATAATTCACAATCTGCAGTTCAAATTCCAATTTATTACTCTTCCAATAGTGAGTTG
GAAAGTAGATGTATAGAATTTCATTCCAAATGTTTAGAAAATTCAAAAAATGGTCTATCA
CTGAAAAAACTATTTAATGAATATAGTGATGTCATTGAGAATGCTACGTTATTATCAATA
TTATCATACTCCTACGACAAATATAACGCCGTTGAACGGAAATTAGTCAAATATGCGAAA
GGTAAACCGCTTGAGGCAGACCTAACGGTGAACGAATTGGATTATGAAAATAATAAAATA
ACGTCTGAGCTGTTTCCAACAGCGGAAGAATACACCGACTCATTGATGGATCCAGCAATT
CTAACTTCCTTGTCATCAAATTTAAACGCAGTCATGTTTTGGTTGGAAAAACACGAAAAT
GATACTGCTGAAAAATTTAAAATTTATAAAAGAAGATTAGACTTATTCACTATAGTAGCT
TCAACCGTAAACAAATATGGTGTACCAAGGCACAATGCAAAATATAGATACGAATATGAT
GTGATGAAAGATAAACCATATTACTTAGTGACATGGGCAAATTCTTCAATTGAAATGCTA
ATGTCAGTCTTTTCTCATGAAGATTATTTAATTGCAAGAGAATTGATAGTGTTGTCATAT
TCTAATAGATCAACTTTGGCAAAACTAGTATCATCTCCAATGTCAATTTTAGTTGCTTTA
GTGGATATTAATGGAACGTTTATTACGAATGAAGAGTTAGAATTAGAGTTTTCAAATAAG
TACGTGCGGGCCATAGTACCAGATCAAACATTTGATGAATTAAAACAGATGCTTAACAGT
ATGAGAAAAGCTGGATTGGTTGATATACCTAAGATGATACAAGACTGGTTAGTTGATTGT
TCCATCGAAAAATTTCCACTAATGGCTAAAATATACTCATGGTCGTTTCATGTTGGATTC
AGAAAGCAAAAAATGTTAGATGCTGCCTTAGACCAATTGAAAACTGAGTATACAGAAGAT
GTAGATGACGAAATGTATCGTGAATACACAATGCTAATAAGAGATGAAGTTGTTAAAATG
CTTGAAGAATCAGTAAAACATGATGACCACCTATTACAAGATTCTGAATTAGCTGGTTTG
TTGTCAATGTCTTCAGCATCGAATGGAGAATCCAGACAGCTTAAATTTGGTAGAAAAACA
GTTTTTTCAACTAAAAAGAACATGCATGTTATGGATGATATGGCTAATGGAAGATATACA
CCAGGCATAATTCCACCTGTAAATGCTGATAAACCAATACCGTTAGGAAGAAGAGACGTA
CCAGGAAGAAGAACTAGAATAATATTCATATTACCGTATGAATATTTTATAGCACAGCAT
GCTGTGGTTGAGAAAATGTTGATCTATGCAAAGCATACTAGAGAATATGCTGAATTCTAT
TCGCAATCAAATCAACTCTTATCATACGGTGATGTTACACGTTTCCTTTCTAATAATGCT
ATGGTGTTATATACAGACGTGTCTCAATGGGATTCATCTCAACATAATACGCAACCGTTT
AGGAAAGGAATAATAATGGGATTGGATATACTAGCTAACATGACTAATGATGCTAAAGTT
ATTCAGACATTAAATTTATATAAACAAACGCAAATTAACTTGATGGACTCATACGTTCAA
ATACCAGATGGTAATGTTATTAAGAAAATACAGTATGGAGCTGTAGCATCAGGGGAAAAA
CAAACGAAGGCAGCTAACTCTATAGCGAATCTGGCACTAATTAAAACGGTTTTATCACGT
ATTTCTAATAAATATTCATTTGCCACAAAAATAATAAGAGTTGACGGTGATGATAACTAT
GCTGTGCTACAATTTAATACAGAAGTAACTAAACAAATGGTTCAGGATGTTTCGAACGAT
GTAAGAGAAACTTATGCACGAATGAATGCTAAAGTTAAAGCTCTAGTATCCACAGTAGGA
ATAGAAATAGCTAAAAGATATATTGCAGGAGGAAAAATATTCTTTAGAGCAGGAATAAAT -continued TTGCTTAATAATGAAAAAAGAGGACAAAGTACACAATGGGATCAGGCAGCAGTTTTATAC
TCTAATTATATCGTAAACAGACTTAGAGGGTTTGAGACTGATAGAGAATTTATTTTAACT
AAAATAATGCAAATGACGTCTGTTGCTATTACTGGATCGCTAAGACTTTTTCCTTCTGAA
CGTGTATTGACTACGAACTCTACATTTAAGGTGTTTGATTCAGAGGATTTTATTATAGAG
TATGGAACAACTGATGATGAAGTATATATACAGAGAGCATTCATGTCTTTGTCAAGTCAG
AGATCAGGAATAGCTGATGAAATAGCCGCATCACCAACATTTAAAAATTATGTGTCTAGA
TTATCAGAACAGCTACTTTTTTCAAAGAATAATATAGTATCTAGAGGAATAGCTTTGACT
GAAAAAGCAAAGTTGAATTCATATGCACCAATATCACTTGAAAAAAGACGTGCGCAGATA
TCAGCTTTGTTAACAATGTTGCAGAAACCAGTTACCTTCAAATCAAACAAAATAACTATA
AACGACATACTTAAAGACATAAAACCATTTTTTACAGTAAGCGAAGCACATTTGCCAATA
CAGTATCAAAAGTTTATGCCGACCGTACCAGAAAATGTACAATATATAATTCAGTGTATA
GGGTCAAGAACTTACCAGATTGAAGATGATGGCTCAAAATCAGCAATATCCCGGCTTATA
TCAAAGTACTCAGTTTATAAACCGTCGATCGAGGAACTATATAAAGTAATTTCATTACAT
GAGAATGAAATACAACTATATTTAATTTCATTAGGCATACCAAAAATAGATGCTGATACA
TATGTTGGTTCAAAAATTTACTCTCAAGATAAATACAGGATATTGGAATCATATGTATAT
AACCTGTTATCCATCAATTACGGATGCTATCAATTATTTGACTTTAATTCACCGGACTTG
GAAAAATTAATTAGAATACCATTCAAAGGGAAGATACCAGCTGTCACATTTATATTACAT
TTATATGCTAAATTAGAAGTTATAAACCATGCTATTAAGAATGGTTCATGGATAAGTCTA
TTCTGTAACTATCCAAAATCAGAAATGATAAAGTTATGGAAGAAAATGTGGAACATTACG
TCGTTACGTTCGCCATATACCAATGCAAATTTCTTTCAAGATTAGAGCGCTTAGATGTGA
CC SEQ ID NO: 13 is an exemplary nucleic acid sequence encoding a VP2 polypeptide from an attenuated G9P GGCTATTAAAGGCTCAATGGCGTACAGGAAACGTGGAGCGCGCCGTGAGGCGAACTTAAA
TAATAATGATCGAATGCAGGAGAAAATTGATGAAAAACAAGATTCAAATAAAATACAATT
ATCTGATAAGGTACTTTCGAAGAAAGAAGAAATTGTAACGGATAGTCATGAGGAAGTTAA
AGTTACTGATGAGTTAAAAAAATCAACGAAAGAAGAATCAAAACAATTGCTTGAAGTGTT
GAAAACAAAGGAAGAACATCAGAAAGAAATACAATATGAAATATTACAGAAAACTATACC
AACATTCGAACCTAAAGAGACGATATTGAGAAAATTAGAGGATATTAAACCAGAACTAGC
GAAAAAACAGACTAAGCTATTTAGAATATTTGAACCGAAACAATTACCGATTTATAGAGC
AAATGGAGAGAGAGAATTGCGTAATAGATGGTATTGGAAATTAAAAAAAGATACACTACC
AGACGGAGACTATGATGTGAGAGAGTATTTTCTGAATTTGTATGATCAAGTGCTTACTGA
AATGCCAGACTACTTATTATTGAAAGATATGGCAGTAGAAAATAAGAATTCTAGGGATGC
AGGTAAAGTCGTTGACTCAGAAACGGCTAGTATATGCGATGCCATATTTCAAGATGAAGA
AACGGAAGGTGCCGTTAGAAGATTCATTGCAGAAATGAGACAACGTGTGCAAGCTGATAG
AAATGTTGTCAATTATCCATCAATATTACATCCAATAGATTATGCATTTAATGAATACTT
TTTACAACATCAATTGGTTGAACCATTGAATAATGATATAATATTTAATTATATACCAGA
AAGGATAAGAAATGATGTTAATTATATTCTCAATATGGACAGAAATTTACCATCAACTGC
CAGATATATAAGACCTAATTTACTGCAAGATAGATTAAATTTGCACGATAATTTTGAATC
ACTATGGGATACAATAACTACATCAAATTATATTTTGGCGAGATCGGTAGTACCAGATTT
AAAGGAATTAGTGTCAACGGAAGCACAAATTCAGAAAATGTCACAAGATTTGCAATTAGA
AGCATTAACAATTCAGTCAGAAACACAATTTCTAACAGGTATAAATTCACAAGCAGCTAA
CGATTGTTTTAAAACCTTAATTGCAGCAATGTTAAGTCAACGTACTATGTCATTAGATTT
TGTGACTACTAATTATATGTCATTGATTTCAGGTATGTGGCTATTGACTGTCGTGCCAAA
TGATATGTTTATAAGGGAATCGTTAGTCGCGTGTCAACTAGCTATAGTAAATACAATAAT
CTATCCAGCATTTGGAATGCAACGAATGCATTATAGAAACGGGGATCCACAAACACCGTT
TCAGATAGCAGAACAGCAAATTCAAAATTTCCAAGTCGCAAATTGGTTACATTTTGTTAA
TAATAATCAATTTAGACAGGCAGTTATTGATGGTGTATTGAATCAGGTACTGAATGACAA
TATTAGAAATGGTCATGTTATTAACCAACTGATGGAAGCTCTAATGCAGCTGTCGCGACA
ACAATTTCCAACCATGCCAATTGATTATAAGAGATCAATTCAACGTGGAATATTACTGTT
ATCTAACAGACTTGGTCAGTTAGTTGATTTAACTAGATTATTAGCTTACAATTATGAGAC
ATTAATGGCATGCATTACAATGAACATGCAACATGTTCAAACCTTAACAACAGAAAAATT
ACAATTAACGTCAGTTACATCATTATGTATGCTTATTGGAAATGCGACTGTTATACCAAG
TCCACAAACATTATTTCATTATTATAACGTTAACGTTAATTTTCATTCAAATTACAATGA
GAGAATTAATGATGCAGTAGCTATAATAACTGCTGCTAACAGACTGAATCTATATCAGAA
AAAAATGAAGGCTATTGTTGAGGATTTCTTAAAAAGATTATACATTTTTGATGTATCTAG
AGTTCCGGACGACCAAATGTATAGATTAAGGGATAGATTACGCTTATTGCCAGTAGAAAT
CAGAAGATTGGATATCTTCAATCTAATACTAATGAACATGGATCAAATTGAACGTGCCTC
AGATAAAATTGCTCAAGGTGTAATCATTGCTTATCGTGACATGCATCTTGAAAGAGATGA
GATGTACGGATATGTAAATATAGCTAGAAATTTAGAGGGATTTCAACAGATAAATTTAGA
GGAGCTGATGAGATCAGGTGACTATGCGCAAATAACTAACATGCTTTTGAATAATCAACC
AGTAGCATTGGTTGGAGCACTTCCATTTATTACTGATTCATCAGTTATATCGCTAATAGC
AAAACTTGACGCTACAGTGTTCGCTCAAATAGTTAAATTACGAAAAGTTGATACTTTAAA
ACCAATATTATACAAGATAAATTCAGACTCAAATGACTTTTATTTAGTAGCCAATTACGA
TTGGGTGCCAACTTCGACTACAAAAGTATACAAACAGGTTCCGCAACAATTTGATTTTAG
AAATTCAATGCATATGTTAACTTCGAATCTTACTTTTACGGTTTATTCAGATCTTCTCGC
GTTCGTATCAGCTGACACAGTAGAACCTATAAATGCAGTTGCATTTGACAATATGCGCAT
CATGAACGAATTGTAGACGCCAACCCCACTGTGGAGATATGACC SEQ ID NO: 14 is an exemplary nucleic acid sequence encoding a VP3 polypeptide from an attenuated G9P GGCTTTTAAAGCAATATCAGTAGTGTGTTTTACCTCTGATGGTGTAAATATGAAAGTATT
AGCTTTAAGACATAGTGTGGCTCAGGTGTATGCAGACACTCAGGTGTACACACATGATGA
TTCTAAAGATGAGTATGAGAACGCATTCTTAATTTCTAATCTCACTACACATAATATATT
ATATTTAAATTATAATGTAAAAACGCTACAAATATTGAATAAATCTGGTATAGCTGCAGT
AGAGATACAGAAGATAGATGAATTATTCACGTTAATTAGATGTAACTTTACATATGATTA
CATTGATGATGTTGTTTACTTACATGACTATTCATATTATACTAATAATGAAATACGGAC
TGACCAACATTGGATAACCAAGACAAATATAGAAGATTATTTATTACCAGGATGGAAGCT -continued GACATACGTTGGATACAATGGAAGTGATACGCGCGGACATTATAATTTTTCATTTAGATG
TCAAAATGCAGCTACAGATGATGATGCAATAATAGAGTATATCTATTCAGATGAATTAGA
CTTCCAGAGTTTTATACTCAAGAAGATTAAAGAAAGGATGACAACATCACTACCAATAGC
AAGACTTTCAAATCGCGTATTTAGAGATAAGTTATTTAAAACGTTATCAGTAAATCATGA
TAAAGTAGTTAATATTGGGCCCAGAAATGAATCTATGTTTACTTTTTTAGACTATCCATC
AATAAAACAGTTTTCGAATGGACCGTATTTAGTTAAAGATACAATTAAACTCAAACAAGA
GAGATGGCTTGGTAAAAGATTATCACAGTTTGATATTGGTCAATATAAGAATATGCTAAA
TGTATTAACGACTTTGTATCAATATTACGATATATATCATGAAAAACCAATCGTATACAT
GATAGGATCAGCGCCCTCATATTGGATATATGACGTCAAACAGTATTCTAACTTGAAATT
TGAAACGTGGGATCCACTAGATACACCATACTCTAATTTACATCATAAGGAATTATTTTA
CATGAATGACGTGCAAAAACTTAAAGATAATTCAATACTATATATAGATATAAGAACAGA
TAGAGGAACTGTAGACTGGAAGGAATGGCGAAAAATAGTGGAAAGGCAAACTATTGACAA
TTTGCATATTGCATACAAATATCTATCTACAGGGAAAGCTAAGGTATGTTGCGTTAAAAT
GACCGCCATGGATTTAGAATTACCGATATCTGCAAAATTGCTTCACCATCCAACTACAGA
GATTAGATCAGAATTTTATCTAGTGATGGATATATGGGACTCTAAAAATATTAAAAGATT
CATACCAAAAGGTGTATTATACTCATATATAAACAATACAATTACTGAAAACGTATTCAT
ACAACAACCTTTTAAGTTGAAAACATTGAAAAACGAATATATAATAGCACTTTATGCTTT
ATCAAATGATTTTAACAACAGAGAAGATGTGGTGAAACTAATTAATAATCAGAAAAAAGC
GTTAATGACAGTGAGAATTAATAATACGTTTAAAGATGAACCAAAAGTCGGATTTAAAAA
CATTTACGATTGGACATTTCTACCAACGGATTTTGAAACTAATGGATCAATAATTACTTC
ATATGATGGGTGTCTAGGTATCTTTGGTTTATCAATATCGCTAGCTTCAAAACCAACTGG
TAATAATCATTTGTTCATTTTAAGTGGAACAGACAAGTATTTTAAACTGGATCAATTTGC
AAATCATATGAGCATATCACGACGATCACATCAGATACGATTTTCGGAGTCAGCCACTTC
ATATTCGGGATATATTTTTAGGGATTTGTCTAATAATAATTTCAATTTAATAGGTACGAA
TATAGAGAATTCAGTATCCGGACACGTATATAATGCATTGATTTATTATAGATATAATTA
TTCATTTGACCTTAAACGATGGATATACTTACATTCAACAGGTAAAGCTAGTATTGAAGG
TGGTAAGTATTATGAACATGCTCCAATTGAATTGATTTATGCATGCAGATCAGCAAGAGA
ATTTGCGAAACTGCAAGATGATTTAACGGTATTAAGATATTCAAATGAGATAGAAAACTA
TATCAATAAAGTTTATAGCATAACATACGCCGACGATCCTAATTACTTTATTGGAGTTAA
GTTTAAAAATATTCCTTATAAGTATAACGTTAAAGTACCACATCTCACATTTGGCGTGTT
AAATATTTCTGAACAAATGCTACCAGATGTAATAACGATTTTAAAGAGATTTAAGAATGA
GTTATTTGGAATGGAAGTAACAACGAGTTATACGTATATGTTATCTGATGAGGTGTATGT
AGCAAATATAAGTGGTGTACTATCAACATATTTCAAAATTTATAATGAGTTTTATAAAGA
GCAAATCACATTTGGACAGTCAAGAATGTTTATTCCTCATGTAACGTTGAGTTTTAGTAA
TGAGAAAACGGTGAGAATAGACACTACAAAACTGTACATAGATTCTATTTACTTAAGAAA
AATAAAAGGTGACACAGTGTTTGATATGACTGGGTGAGCTAAAAACTTAACACACTGGTC
ACGATGTGACC SEQ ID NO: 15 is an exemplary nucleic acid sequence encoding a VP4 polypeptide from an attenuated G9P GGCTATAAAATGGCTTCGCTCATTTATAGACAGCTACTCACTAATTCATACACAGTTGAA
TTATCAGATGAAATTAATACAATTGGATCAGAAAAAAGTCAAAATGTAACGATTAATCCC
GGACCGTTTGCTCAAACAAATTATGCACCAGTGACTTGGAGTCATGGGGAAGTGAATGAT
TCGACAACGATAGAGCCAGTACTCGATGGTCCTTATCAACCAACAAATTTTAAGCCACCA
AATGATTACTGGATATTATTGAATCCAACTAATCAACAAGTTGTATTAGAGGGTACCAAT
AAAATTGATATTTGGGTTGCTTTATTACTTGTTGAACCAAACGTAACCAATCAAAGTAGA
CAATACACATTATTTGGAGAAACGAAACAAATTACTGTAGAAAATAACACAAACAAATGG
AAATTCTTCGAAATGTTCAGAAGTAATGTTAGTGCCGAATTTCAACATAAGCGCACTTTA
ACATCAGACACTAAATTAGCTGGGTTTATGAAATTTTATAATAGTGTTTGGACTTTCCGC
GGTGAAACGCCGCATGCTACAACTGATTACTCGTCAACTTCAAATTTATCTGAAGTAGAA
ACTGTAATACATGTTGAGTTTTATATAATACCAAGATCGCAAGAATCTAAGTGTAGTGAA
TACATAAATACTGGATTACCACCAATGCAGAATACAAGGAATATAGTTCCAGTTGCGTTA
TCATCTAGGTCAGTGACTTATCAACGTGCTCAGGTTAATGAGGATATCATTATATCAAAG
ACATCGTTGTGGAAAGAAATGCAATGTAACAGAGATATTATAATAAGGTTTAAATTTAAT
AATAGTATAGTAAAACTTGGTGGGCTAGGTTATAAATGGTCAGAAATTTCGTTTAAAGCG
GCTAATTATCAGTACAGTTACTTGCGAGATGGAGAGCAAGTTACGGCACATACTACTTGC
TCAGTTAATGGTGTGAATAACTTCAGTTATAATGGAGGATCACTACCAACTGATTTTAGT
GTATCAAGATATGAAGTGATTAAAGAGAATTCTTATGTTTATGTTGATTATTGGGATGAC
TCACAAGCATTTAGGAACATGGTATATGTCAGGTCATTGGCAGCAAATTTAAATTCAGTG
AAGTGTAGCGGAGGAACTTATAATTTTCAACTACCAGTTGGTGCATGGCCAGTGATGAGT
GGAGGTGCAGTGTCTTTACATTTCGCAGGAGTCACTTTATCCACTCAATTTACTGACTTC
GTATCACTTAATTCGTTAAGATTTAGATTCAGTTTAACCGTTGAAGAGCCACCGTTTTCA
ATTTTACGTACACGTGTGTCAGGATTGTACGGGCTACCAGCATTCAATCCGAATGACGGA
CATGAATACTATGAAATAGCTGGGAGATTTTCTCTTATTTCATTAGTGCCGTCTAATGAC
GATTATCAAACTCCAATCATGAATTCAGTTACAGTGCGACAAGATCTTGAACGTCAACTA
GGTGATTTAAGGGAGGAATTCAATTCCTTATCACAAGAAATAGCAATGACGCAATTGATA
GATTTAGCATTATTGCCATTAGATATGTTTTCTATGTTTTCAGGTATTAAAAGCACAATT
GACGTAGCCAAATCAATGGTCACAAAGGTGATGAAAAAGTTTAAGAAATCAGGATTAGCT
ACATCAATCTCTGAATTGACTGGATCATTATCAAACGCTGCTTCATCAGTTTCCAGAAGT
TCATCTATTAGATCTAACATATCATCCATATCAGTGTGGACGGATGTTTCCGAACAAATA
GCGGGTTCGTCAGACTCCGTCAGGAACATTTCCACGCAAACGTCAGCTATTAGTAAAAGA
TTGCGACTACGCGAAATTACTACACAAACTGAAGGTATGAATTTTGATGATATTTCAGCG
GCAGTTCTTAAAACTAAAATAGATAGATCAACTCACATAAGCCCAAATACATTACCAGAC
ATAATAACTGAGTCATCTGAAAAGTTTATACCAAAACGAGCTTATAGAGTTCTAAAAGAT
GATGAAGTGATGGAAGCTGATGTGGATGGGAAGTTCTTTGCATATAAAGTTGGCACTTTT
GAAGAAGTACCATTTGACGTAGATAAATTTGTTGATTTGGTAACCGATTCTCCTGTAATT
TCAGCTATAATTGATTTTAAGACGTTGAAGAATTTAAACGACAATTATGGTATAACGCGA -continued TCTCAAGCGTTAGACTTAATCAGATCTGATCCCAGAGTTTTACGCGATTTTATCAACCAG
AATAATCCAATTATTAAAAATAGAATTGAACAGCTAATATTGCAATGTAGACTGTGAGAG
CTCTATAGAGGATGTGACC SEQ ID NO: 16 is an exemplary nucleic acid sequence encoding a VP6 polypeptide from an attenuated G9P GGCTTTAAAACGAAGTCTTCAACATGGATGTCCTGTACTCCTTATCAAAAACTCTTAAAG
ATGCTAGAGACAAAATTGTCGAAGGCACATTATACTCTAATGTGAGTGATCTAATTCAAC
AATTTAACCAAATGATAATTACTATGAATGGAAATGAGTTCCAAACTGGAGGAATTGGTA
ATCTACCAATTAGAAATTGGAATTTTGATTTTGGATTACTTGGAACAACTCTACTAAATT
TAGACGCTAACTACGTCGAAACAGCCCGTAACACAATTGATTATTTTGTAGATTTTGTAG
ATAACGTATGTATGGATGAAATGGTTAGAGAATCACAAAGAAATGGAATTGCACCACAGT
CAGACTCACTTAGAAAATTGTCAGGCATTAAGTTCAAAAGGATAAATTTTGATAATTCAT
CGGAATATATAGAGAACTGGAATCTGCAAAACAGAAGACAACGAACAGGTTTTACATTTC
ATAAACCAAATATTTTTCCTTATTCAGCGTCATTCACACTGAATAGATCACAACCAGCTC
ATGATAACTTGATGGGTACAATGTGGCTGAACGCAGGATCAGAAATTCAGGTCGCTGGAT
TCGACTATTCGTGTGCAATTAATGCGCCAGCTAATACACAACAATTTGAACATATTGTAC
AGCTCCGAAGAGTTTTAACTACAGCTACAATAACACTTTTACCGGATGCAGAAAGATTCA
GTTTTCCAAGAGTGATTAATTCAGCTGATGGAGCAACTACATGGTATTTTAATCCAGTAA
TTCTTAGACCAAATAACGTTGAAGTGGAGTTTCTACTAAACGGGCAGATAATAAACACTT
ACCAGGCTAGATTTGGAACGATCGTAGCTAGAAATTTTGATACAATCAGATTGTCGTTTC
AGTTGATGAGACCACCAAATATGACACCATCGGTAGCAGCATTATTTCCAAATGCGCAAC
CATTTGAACATCATGCTACAGTAGGACTTACATTGAAAATTGAATCTGCAGTTTGTGAAT
CTGTACTTGCTGACGCAAGCGAGACAATGCTAGCAAATGTGACATCTGTTAGACAAGAAT
ACGCGATACCAGTTGGACCAGTCTTTCCACCAGGTATGAATTGGACTGATTTGATCACTA
ACTATTCACCATCTAGAGAGGATAACTTGCAGCGTGTATTTACAGTGGCTTCCATTAGAA
GCATGCTTGTCAAATAAGGACCAAGCTAACCACTTGGTATCCAACTTTGGTGAGTATGTA
GCTACGTCAAGCTGTTTGAACTCTGTAAGTAAGGATGCGCTTACGTATTCGCTACACAGA
GTAATCACTCAGATGACGTAGTGAGAGGATGTGACC SEQ ID NO: 17 is an exemplary nucleic acid sequence encoding a VP7 polypeptide from an attenuated G9P GGCTTTAAAAGAGAGAATTTCCGTTTGGCTAGCGGTTAGCTCCTTTTAATGTATGGTATT
GAATATACTACAATTCTAACCTTTCTGATATCAATAGTTTTATTGAACTATATATTAAAA
TCACTAACTAGTGCGATGGACTTTATAATTTATAGATTTCTTTTACTTATTGTTATTGCA
TCACCTTTTGTTAAAACACAAAATTATGGAATTAATTTACCGATCACTGGCTCCATGGAT
ACAGCATATGCAAATTCATCACAGCAAGAAACATTTTTGACTTCAACGCTATGCTTATAT
TATCCTACAGAAGCATCAACTCAAATTGGAGATACGGAATGGAAGGATACTCTGTCCCAA
TTATTCTTGACTAAAGGGTGGCCAACTGGATCAGTCTATTTTAAAGAATACACCGATATC
GCTTCATTCTCAATTGATCCGCAACTTTATTGTGATTATAATGTTGTACTGATGAAGTAT
GATTCAACGTTAAAGCTAGATATGTCTGAATTAGCTGATTTAATTCTAAATGAATGGTTA
TGTAACCCAATGGATATAACATTATATTATTATCAGCAAACAGATGAAGCGAATAAATGG
ATATCGATGGGACAGTCTTGTACCATAAAAGTATGTCCATTGAATACGCAGACTTTAGGA
ATAGGTTGTATTACCACAAATACAGCGACATTTGAAGAGGTGGCTACAAATGAAAAATTA
GTAATAACCGATGTTGTTGATGGTGTGAACCATAAACTTGATGTGACTACAAATACCTGT
ACAATTAGGAATTGTAAGAAGTTGGGACCAAGAGAAAATGTAGCGATTATACAAGTCGGT
GGCTCAGATGTGTTAGATATTACAGCGGATCCAACTACTGCACCACAAACTGAACGTATG
ATGCGAGTAAATTGGAAGAAATGGTGGCAAGTTTTCTATACAGTAGTAGATTATATTAAT
CAGATTGTGCAAGTTATGTCCAAAAGATCACGGTTATTAAATTCAGCAGCTTTTTACTAT
AGGGTTTGATATATCTTAGGTTAGAATTGGTCGATGTGACC SEQ ID NO: 18 is an exemplary nucleic acid sequence encoding a NSP1 polypeptide from an attenuated G9P GGCTTTTTTTATGAAAAGTCTTGTGGAAGCCATGGCTACTTTTAAAGACGCTTGCTATCA
ATATAAAAAATTAAACAAATTAAATAATGCAGTTTTAAAGTTAGGAGCTAATGATGTTTG
GAGACCTTCTACTCTAACAAAACGTAAAGGATGGTGCTTAGATTGTTGTCAACATACGGA
CTTGACTTATTGCCAAGGATGCTTAATATATCATGTTTGTGAATGGTGTAGTCAATATAG
TAGATGCTTTCTTGATAATGATCCGCATTTACTAAGAATGCGAACTTTTAGAAATGAAAT
CACAAAGAGTGACTTAGAAAACTTAATTAATATGTATGATACATCATTTCCTATAAATCA
AAAAATAGTTAATAAGTTTGCAAACGCAATTAAACAACATAAATGTAGAAATGAGTATTT
GATACAATGGTATAATCATTTTTTAATGCCAATTACACTACAGTCTTTATCAATAGAATT
AGATGGAGATATATATTATATATTTGGTTACTATGACGATATGCATAAAATTAATCAGAC
TCCCTTCTCATTCACGAATTTAATTAGTAAATATGATGTATTACTGCTAGATAGTATAAA
TTTTGACAGAATGGCATTTTTACCATTAACATTACAGCAAGAGTATGCACTTAGATATTT
TTCAAAATCAAGATTTATTACTGAAAGAAGGAAATGTATTGAAATTTCACATTTTTCAGA
TAATATATTAAATGATTTACATAACCCGAATTTTACATTACAAGTGATTAGAAATTGCAG
TAATATGTCAGTTGAATGGAATAAAGCATGTAATCTTATTAGAAATATAAGTAATTATTT
CGATATATTCAAATCGTCACATACTGAGTCTTATAATATATCTCCTAGATGTAGAGTATT
CACACAATATAAATTAAAAATAGCATCTAAATTAATTAAACCAAATTATGTAGCATCAAA
TCATAATTCCTTGGCTACTGAAGTACACAATTGCAAATGGTGTTCAATTAATAATAATTC
TATTGTATGGACTGATTTCAGAATTAAAAATGTTTATAATGATATATTTAATTTTATTAG
GGCTTTAGTGAAATCAAATCTTTACGTGGGACATTGTTCTTCAGAAGAAAAGATATATGA
ATCTATTAAGGATATTTTAAATGTATGTAAAGAAAACGAATGGAACATGTTGGTAACGGA
AATATTCAATCAATTAGATCCAATAAAGCTAAATGAGGATAGCTATGTTTTGTTGAATTA
TGAAATAAATTGGAATGTTATGAATGTATTAATTAATAGTATCGGTAAAGTACCAAAAAT
ATTAACTTTGAGTGACGTTATTTCGATTTTACGTATAATAATATATGATTGGTTTGACAT
AAGGTTTATGAGAAATACTCCAATGACTACGTTCACAGTTAATAAATTAAAGCAATTATA -continued

```
TGAAAAGGATAGAACTGCAGAATATGATTCAGGTGTATCCGATGTTGAATAATTTCAGAG
AAATTATGTTCGCCACCATGAGACTCTCTGCACTAGAGTAGCGCCTAGGCAGCATAAAAT
GTAACC
```

SEQ ID NO: 19 is an exemplary nucleic acid sequence encoding a NSP2 polypeptide from an attenuated G9P

```
GGCTTTTAAAGCGTCTCAGTCGCCGTTTGAGCCTTGCGGTGTAGCCATGGCTGAGCTAGC
TTGCTTTTGCTATCCCCATTTGGAGAACGATAGCTATAAATTTATTCCTTTTAACAATTT
GGCTATAAAATGTATGTTGACAGCAAAAGTAGAGAAAAAAGATCAGGACAAATTTTACAA
CTCGATAATCTATGGTATTGCGCCGCCGCCACAATTTAAAAAACGCTATAATACAAATGA
TAACTCAAGAGGAATGAATTATGAGACTGCAATGTTTAACAAAGTGGCGGTGCTAATTTG
TGAAGCACTGAATTCAATTAAAGTCACGCAGTCTGATGTTGCAAGTGTACTTTCAAGAGT
AGTTTCTGTGAGACATCTTGAGAATTTAGTATTGAGAAGAGAAAATCATCAGGACGTTCT
TTTTCACTCAAAGGAGCTACTACTCAAATCAGTTTTAATAGCTATTGGTCATTCAAAGGA
GATTGAAACGACTGCCACTGCTGAAGGGGGAGAAATTGTTTTTCAAAATGCAGCATTTAC
AATGTGGAAATTGACATACTTGGAACATAAACTAATGCCAATTCTTGATCAAAACTTTAT
TGAATATAAAATTACATTAAATGAAGATAAACCAATTTCAGAGTCACACGTAAAAGAACT
TATTGCTGAATTACGGTGGCAATACAATAAATTTGCAGTAATTACGCATGGTAAAGGTCA
CTATAGAGTTGTAAAATACTCGTCAGTTGCAAATCACGCAGACCGAGTTTACGCTACTTT
TAAGAGTAATAACAAAAACGGAGGTCCACTAGAGTTTAATTTGCTTGACCAAAGGATAAT
ATGGCAAAATTGGTACGCATTTACGTCCTCAATGAAACAAGGTAATGCTCTTGATGTATG
CAAAAAACTACTCTTCCAAAAAATGAAGCGAGAAAGTAATCCATTTAAGGGGCTGTCAAC
TGATAGAAAAATGGATGAAGTTTCTCAAGTAGGAATCTAATTCGTTATCTGTTTGAAGGT
GGGTATGGCAGAGTAAGAATTGAAAGCGCTTATGTGACC
```

SEQ ID NO: 20 is an exemplary nucleic acid sequence encoding a NSP3 polypeptide from an attenuated G9P

```
GGCTTTTAATGCTTTTCAGTGGTTGATGCTCAAGATGGAGTCTACTCAGCAGATGGCATC
TTCTATTATTAACTCTTCTTTTGAAGCTGCAGTTGTCGCTGCAACTTCTACATTGGAATT
AATGGGTATTCAATATGATTATAATGAAGTATATACTAGAGTTAAAAGTAAGTTTGATTT
TGTAATGGATGATTCTGGCGTTAAGAATAATTTAATAGGTAAAGCAGCTACAATTGATCA
GGCTTTGAATGGTAAGTTTAGTTCATCTATCAGAAATAGAAATTGGATGACTGATTCAAA
AACTGTAGCAAGATTAGATGAAGATGTGAACAAACTTAGATTATTATTGTCATCGAAAGG
AATTGATCAAAAAATGAGAGTTCTTAATGCATGCTTTAGTGTTAAAAGAGTACCTGAAAA
ATCGTCATCTATCATTAAATGTACTAGGTTAATGAAAGAGAAAATAGAACGTGGAGAAGT
CGAAGTGGATGATACATTCATTGAAGAAAAAATGGAAATTGACACTATAGATTGGAAATC
CAGATATGATCAACTTGAAAGACGATTTGAGTCGTTAAAACAGCGAGTTAACGAAAAGTA
CAATAATTGGGTTATTAAGGCAAGGAAAATAAACGAAAACATGAACTCTCTTCAGAATGT
TATTTCGCAACAACAAGCTCATATCAATGAATTACAAATATATAATGATAAACTAGAGCG
TGATTTACAATCAAAAATAGGATCAGTTATTTCATCCATTGAATGGTACTTACGGTCTAT
GGAACTATCAGATGACATTAAATCAGATATTGAACAACAACTCAATTCAATAGATCATAT
TAATCCAGTTAATGCTTTTGATGATTTTGAGTCTATTCTTCGTAATTTAATATCTGATTA
TGATAGAATTTTTATTATGTTTAAAGGATTGTTGCAGCAAAGTAATTACACATATACCTA
TGAGTAAACATAGCATATTACCATCTTCACGTAACCCTCTATGAGCACAATAGTTAAAAG
CTAACACTGTCAAAAACCTAAATGGCTATAGGGGCGTTATGTGACC
```

SEQ ID NO: 21 is an exemplary nucleic acid sequence encoding a NSP4 polypeptide from an attenuated G9P

```
GGCTTTTAAAAGTTCTGTTCCGAGAGAGCGCGTGCGGAAAGATGGAAAAGTTTACCGACCTCAACTACAC
ATTGAGTGTAATCACTTTAATGAATAGCACATTACATACAATACTAGAGGATCCAGGAATGGCGTATTTT
CCTTATATTGCATCTGTCCTGACAGTTTTGTTTACATTACACAAAGCGTCAATTCCAACAATGAAAATAGC
ATTGAAGACGTCAAAATGTTCGTATAAAGTAGTAAAGTATTGCATTGTGACAATCCTTAATACATTATTA
AAGTTAGCAGGTTACAAAGAACAAATTACTACTAAAGATGAAATAGAAAAACAAATGGACAGAGTTGTT
AAAGAAATGAGACGTCAATTAGAGATGATCGATAAACTAACTACACGTGAAATTGAACAAGTCGAATTA
CTTAAACGCATCTACGATAAATTAATAGTGCGATCAACTGATGAGATAGATATGACAAAAGAAATTAATC
AAAAGAACGTAAGAACGCTAGAAGAGTGGGAGAGCGGAAAAAATCCTTATGAACCAAAAGAAGTGACT
GCAGCGATGTGAGAGGTTGAGCTGCCGTCGACTGTCTTCGGAAGCGGCGGAGTTCTTTACAGTAAACTCC
ATTGGACCTGATGGCTGGCTAAGAAGCCATAGTCAGCCATATCGCGTGTGGCTCAAGCCTTAATCCCGTT
TAACTAATCCGGTCAGCACCGGACGTTAATGGAAGGAACGGTCTTAATGTGACC
```

SEQ ID NO: 22 is an exemplary nucleic acid sequence encoding a NSP5 polypeptide from an attenuated G9P

```
GGCTTTTAAAGCGCTACAGTGATGTCTCTTAGTATTGACGTGAATAGTCTTCCTTCAATT
TCTTCTAGCGTTTATAAAAATGAATCGTTTTCAACAACGTCAACTATTTCTGGAAAATCT
ATTGGTAGGAGTGAACAGTACATTTCACCAGATGCAGAAGCTTTCAATAAGTACATGTTG
TCAAAATCTCCAGAAGATATTGGACCTTCTGATTCTGCATCGAACGATCCACTCACCAGC
TTTTCGATTAGATCGAATGCAGTTAAGACAAATGCAGATGCTGGCGTGTCTATGGATTCA
TCAGCACAATCACGACCATCTAGCGACATTGGATACGATCAAATGGATTTCTCCTTAAAT
AAAGGTATTAAAATTGATGCTACAATGGATTCTTCAATATCAATATCTACTACATCAAAG
AAGGAGAAATCTAAACAAGAGAACAAAAATAAATATAAAAAATGTTATCCAAAAATTGAA
GCAGAATCTGATTCTGATGAATACGTATTAGATGATTCAGATAGTGATGATGGAAAATGT
AAAAATTGCAAGTATAAAAAGAAATATTTTGCACTTCGTTTAAGAATGAAACAAGTTGCA
ATGCAATTGATTAAAGATTTGTGAAAATTTTCTGATTACTCTTATCATTAACTGTTAAAT
ATTTACTTATTATACGGATGATAAGTGTTGTTTAATTATATTATATAATAGTATTATTAT
ATCGCGTTATTGAATTTAACAACTTTCTAATGAGAGAAGATTAATGCGTCTACCCTAAGA
GATCACTAGGGAGCTCCCCACTCCCGTTTTGTGACC
```

DETAILED DESCRIPTION OF SEVERAL EMBODIMENTS

Disclosed herein is an attenuated G9P[6] rotavirus that can be included in a pharmaceutical composition for administration to a subject. In additional embodiments, the pharmaceutical composition is a vaccine The attenuated rotavirus can induce an immune response, and/or prevent disease associated with rotavirus infection, from the same rotavirus type (e.g., G9P[6]) and/or another rotavirus type. In some embodiments, the vaccine is effective to induce an immune response against more than one type of rotavirus. In further embodiments, the vaccine can be used to induce a homotypic immune response to DS-1 like strains. In more embodiments, the vaccine can be used to induce a heterotypic immune response to Wa-1 like strains.

The pharmaceutical composition can include other components, such as an inactivated G1P[8] rotavirus. The G1P [8] rotavirus can be a heat inactivated rotavirus. In some embodiments, the pharmaceutical composition includes an adjuvant.

Isolated nucleic acids and proteins from the attenuated G9P[6] rotavirus are also disclosed. These components can also be used in pharmaceutical compositions.

Methods are also disclosed for inducing an immune response to a rotavirus in a subject. The subject can be a child, such as a human of less than five years of age or less than one year of age. The immune response can be a protective immune response. In some embodiments, methods for vaccination are disclosed. In some embodiments, these methods can include at least one prime and boost.

Terms

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). In order to facilitate review of the various embodiments of the disclosure, the following explanations of specific terms are provided:

Adjuvant: A substance or vehicle that non-specifically enhances the immune response to an antigen. Adjuvants can include a suspension of minerals (alum, aluminum salts, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants also include biological molecules, such as costimulatory molecules. Exemplary biological adjuvants include interleukin (IL)-2, RANTES, granulocyte macrophage colony stimulating factor (GM-CSF), tumor necrosis factor (TNF)-α, interferon (IFN)-γ, granulocyte colony stimulating factor (G-CSF), lymphocyte function-associated antigen 3 (LFA-3), CD72, B7-1, B7-2, OX-40L and 4-1BBL. An adjuvant can be an aluminum adjuvant, such as aluminum salts, aluminum phosphate or aluminum hydroxide.

Administer: To give, apply or bring the composition into contact with the subject. Administration can be accomplished by any of a number of routes, such as, for example, topical, transcutaneous, oral, intranasal, subcutaneous, intramuscular, intraperitoneal, intravenous and intrathecal. A composition can be administered therapeutically or prophylactically. Prophylactic administration can occur prior to manifestation of symptoms characteristic of an infection, such as a rotavirus infection.

Animal: Living multicellular vertebrate organisms, a category which includes, for example, mammals and birds.

Antigen: A compound, composition, or substance that can stimulate the production of antibodies or a T-cell response in an animal, including compositions that are injected or absorbed into an animal. An antigen reacts with the products of specific humoral or cellular immunity. Antigens include, but are not limited to VP4 and VP7.

Attenuated: In the context of a live virus, the virus is attenuated if its ability to infect a cell or subject and/or its ability to produce disease is reduced (for example, eliminated) compared to a wild-type virus. Typically, an attenuated virus retains at least some capacity to elicit an immune response following administration to an immunocompetent subject. In some cases, an attenuated virus is capable of eliciting a protective immune response without causing any signs or symptoms of infection, such as a rotavirus infection. In some embodiments, the ability of an attenuated virus to cause disease in a subject is reduced at least about 10%, at least about 25%, at least about 50%, at least about 75% or at least about 90% relative to wild-type virus. Accordingly, an "attenuating mutation" is a mutation in the viral genome and/or an encoded polypeptide that results in an attenuated virus.

Biological sample: A sample obtained from a subject (such as a human or veterinary subject). Exemplary biological samples include fluid, cell and/or tissue samples. In some embodiments herein, the biological sample is a fluid sample. Fluid samples include, but are not limited to, serum, blood, plasma, urine, feces, saliva, cerebral spinal fluid (CSF) or other bodily fluid. Biological samples can also refer to cells or tissue samples, such as biopsy samples, tissue sections or isolated leukocytes.

Contacting: Placement in direct physical association; includes both in solid and liquid form. "Contacting" is often used interchangeably with "exposed." In some cases, "contacting" includes transfecting, such as transfecting a nucleic acid molecule into a cell. In other examples, "contacting" refers to incubating a molecule (such as an antibody) with a biological sample.

Degenerate variant: In the context of the present disclosure, a "degenerate variant" refers to a polynucleotide encoding a polypeptide that includes a sequence that is degenerate as a result of the genetic code. There are 20 natural amino acids, most of which are specified by more than one codon. Therefore, all degenerate nucleotide sequences encoding a peptide are included as long as the amino acid sequence of the peptide encoded by the nucleotide sequence is unchanged. Detecting: Determining the presence, using any method, of the virus or viral particles including viral peptides, inside cells, on cells, and/or in medium with which cells or the virus have come into contact. The methods are exemplified by, but not limited to, the observation of cytopathic effect, detection of viral protein, such as by immunofluorescence, ELISA, or Western blot hybridization, detection of viral nucleic acid sequence, such as by PCR, RT-PCR, Southern blots, and Northern blots, nucleic acid hybridization, nucleic acid arrays, and the like.

Diarrhea: The condition of having at least three loose or liquid bowel movements each day. It often lasts for a few days and can result in dehydration due to fluid loss. Signs of dehydration often begin with loss of the normal stretchiness of the skin and changes in personality. This can progress to decreased urination, loss of skin color, a fast heart rate, and a decrease in responsiveness as it becomes more severe. The most common cause is an infection of the intestines due to either a virus, bacteria, or parasite; a condition known as gastroenteritis. Diarrhea is most commonly due to viral gastroenteritis with rotavirus, which accounts for 40% of cases in children under five.

Expression Vector: A plasmid, a virus or another medium, known in the art, into which a nucleic acid sequence for encoding a desired protein can be inserted or introduced.

Heterologous: A heterologous sequence is a sequence that is not normally (i.e. in the wild-type sequence) found adjacent to a second sequence. In one embodiment, the sequence is from a different genetic source, such as a different virus or organism, than the second sequence.

Host cell: A cell that is susceptible to transformation, transfection, transduction, conjugation, and the like with an exogenous nucleic acid construct or expression vector. Host cells can be from mammals, plants, bacteria, yeast, fungi, insects, animals, etc. A host cell can be from a human or a non-human primate.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are discussed by Sambrook et al. (ed.), *Molecular Cloning: A Laboratory Manual,* $2^{nd}$ ed., vol. 1-3, Cold Spring Harbor Laboratory Press, Cold Spring Harbor, N.Y., 1989, chapters 9 and 11; and Ausubel et al. *Short Protocols in Molecular Biology,* $4^{th}$ ed., John Wiley & Sons, Inc., 1999.

For purposes of the present disclosure, "stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize.

"Specific hybridization" refers to the binding, duplexing, or hybridizing of a molecule only or substantially only to a particular nucleotide sequence when that sequence is present in a complex mixture (for example, total cellular DNA or RNA). Specific hybridization may also occur under conditions of varying stringency. Hybridization conditions resulting in particular degrees of stringency will vary depending upon the nature of the hybridization method and the composition and length of the hybridizing nucleic acid sequences. The following is an exemplary set of hybridization conditions and is not limiting:

Very High Stringency (detects sequences that share at least 90% identity)

Hybridization: 5×SSC at 65° C. for 16 hours

Wash twice: 2×SSC at room temperature (RT) for 15 minutes each

Wash twice: 0.5×SSC at 65° C. for 20 minutes each

High Stringency (detects sequences that share at least 80% identity)

Hybridization: 5×-6×SSC at 65° C.-70° C. for 16-20 hours

Wash twice: 2×SSC at RT for 5-20 minutes each

Wash twice: 1×SSC at 55° C.-70° C. for 30 minutes each

Low Stringency (detects sequences that share at least 60% identity)

Hybridization: 6×SSC at RT to 55° C. for 16-20 hours

Wash at least twice: 2×-3×SSC at RT to 55° C. for 20-30 minutes each

Immune response: A response of a cell of the immune system, such as a B-cell, T-cell, macrophage or polymorphonucleocyte, to a stimulus such as a rotaviral antigen or a vaccine. An immune response can include any cell of the body involved in a host defense response, including for example, an epithelial cell that secretes an interferon or a cytokine. An immune response includes, but is not limited to, an innate immune response or inflammation. As used herein, a "protective" immune response refers to an immune response that protects a subject from infection (prevents infection or prevents the development of disease associated with infection) or reduces the effects of the infection.

Immunogen: A compound, composition, or substance which is capable, under appropriate conditions, of stimulating an immune response, such as the production of antibodies or a T-cell response in an animal, such as to a rotavirus. An immunogen includes compositions that are injected or absorbed into an animal. As used herein, an "immunogenic composition" is a composition comprising an immunogen. Exemplary immunogens include a rotavirus, a rotavirus polypeptide, or a nucleic acid encoding a rotavirus polypeptide that can be expressed in a cell.

Immunize: To render a subject protected from an infectious disease, such as by vaccination.

Isolated: An "isolated" biological component (such as a nucleic acid, protein or virus) has been substantially separated or purified away from other biological components (such as cell debris, or other proteins or nucleic acids). Biological components that have been "isolated" include those components purified by standard purification methods. The term "isolated" also embraces recombinant biological components, such as nucleic acids, proteins or viruses, as well as chemically synthesized nucleic acids or peptides, that are not in their natural environment. An isolated composition can be at least 90%, 91%, 92%, 93%, 94%, 95%, 96%, 97%, 98%, 99% or 100% pure.

Label: A detectable moiety or any atom, molecule or a portion thereof, the presence, absence or level of which is directly or indirectly monitorable. A variety of detectable moieties are well known to those skilled in the art, and can be any material detectable by spectroscopic, photochemical, biochemical, immunochemical, electrical, optical or chemical means. Such detectable labels can include, but are not limited to, magnetic beads, fluorescent dyes, radiolabels, enzymes, and colorimetric labels such as colloidal gold or colored glass or plastic beads.

Mammal: This term includes both human and non-human mammals. Similarly, the term "subject" includes both human and veterinary subjects.

Nucleic acid: Deoxyribonucleotides, ribonucleotides, and polymers thereof, in either single-stranded or double-stranded form. This term includes complements of single stranded nucleotides and cDNAs. This term also includes RNA. Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions can be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleotide sequence can encompass "splice variants," which as the name suggests, are products of alternative splicing of a gene. After transcription, an initial nucleic acid transcript can be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. A polynucleotide is generally a linear nucleotide sequence, including sequences of greater than 100 nucleotide bases in length.

Oligonucleotide: A short nucleic acid polymer. Oligonucleotides are generally less than 100 nucleotides in length. In some embodiments herein, the oligonucleotide is 8-100, 10-50, 12-40, 16-30 or 18-24 nucleotides in length. In particular examples, the oligonucleotide is 12, 13, 14, 15, 16, 17, 18, 19, 20, 21, 22, 23, 24, 25, 26, 27, 28, 29 or 30 nucleotides in length.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

ORF (open reading frame): A series of nucleotide triplets (codons) coding for amino acids without any termination codons. These sequences are usually translatable into a peptide.

Pharmaceutically acceptable carrier: The pharmaceutically acceptable carriers (vehicles) useful in this disclosure are conventional. Remington's Pharmaceutical Sciences, by E. W. Martin, Mack Publishing Co., Easton, Pa., 15th Edition (1975), describes compositions and formulations suitable for pharmaceutical delivery of one or more therapeutic compounds or molecules, such as one or more rotaviruses, such as attenuated and/or inactivated viruses, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced. The term "residue" or "amino acid residue" includes reference to an amino acid that is incorporated into a protein, polypeptide, or peptide.

Conservative amino acid substitutions are those substitutions that, when made, least interfere with the properties of the original protein, that is, the structure and especially the function of the protein is conserved and not significantly changed by such substitutions. Examples of conservative substitutions are shown below.

| Original Residue | Conservative Substitutions |
|---|---|
| Ala | Ser |
| Arg | Lys |
| Asn | Gln, His |
| Asp | Glu |

-continued

| Original Residue | Conservative Substitutions |
|---|---|
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Preventing, treating or ameliorating a disease or infection: "Preventing" a disease refers to inhibiting the full development of a disease or symptoms of an infection. "Treating" refers to a therapeutic intervention that ameliorates a sign or symptom of a disease or pathological condition, such as an infection after it has begun to develop. "Ameliorating" refers to the reduction in the number or severity of signs or symptoms of a disease.

Probes and primers: A probe comprises an isolated nucleic acid molecule attached to a detectable label or other reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, for example, in Sambrook et al. (ed.), *Molecular Cloning: A Laboratory Manual,* $2^{nd}$ ed., vol. 1-3, Cold Spring Harbor Laboratory Press, Cold Spring Harbor, N.Y., 1989 and Ausubel et al. *Short Protocols in Molecular Biology,* $4^{th}$ ed., John Wiley & Sons, Inc., 1999.

Primers are short nucleic acid molecules, for instance DNA oligonucleotides 10 nucleotides or more in length, for example that hybridize to contiguous complementary nucleotides or a sequence to be amplified. Longer DNA oligonucleotides may be about 12, 15, 18, 20, 25, 30, or 50 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, for example, by the polymerase chain reaction (PCR) or other nucleic-acid amplification methods known in the art. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification; gap filling ligase chain reaction amplification, as disclosed in 5,427,930; and NASBA™ RNA transcription-free amplification, as disclosed in U.S. Pat. No. 6,025,134.

Methods for preparing and using nucleic acid probes and primers are described, for example, in Sambrook et al. (ed.), *Molecular Cloning: A Laboratory Manual,* $2^{nd}$ ed., vol. 1-3, Cold Spring Harbor Laboratory Press, Cold Spring Harbor, N.Y., 1989; Ausubel et al. *Short Protocols in Molecular Biology,* $4^{th}$ ed., John Wiley & Sons, Inc., 1999; and Innis et al. *PCR Protocols, A Guide to Methods and Applications, Academic Press, Inc., San Diego, Calif.,* 1990. Amplification primer pairs can be derived from a known sequence, for example, by using computer programs intended for that purpose such as Primer (Version 0.5, © 1991, Whitehead Institute for Biomedical Research, Cambridge, Mass.).

Promoter: A promoter is an array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription.

Purified: The term "purified" does not require absolute purity; rather, it is intended as a relative term. Thus, for example, a purified protein preparation is one in which the protein referred to is more pure than the protein in its natural environment within a cell. For example, a preparation of a protein is purified such that the protein represents at least 50% of the total protein content of the preparation. Similarly, a purified oligonucleotide preparation is one in which the oligonucleotide is more pure than in an environment including a complex mixture of oligonucleotides. A purified population of nucleic acids or proteins is greater than about 90%, 91%, 92%, 93%, 94%, 95%, 96%, 97%, 98%, 99% or 100% pure, or free other nucleic acids or proteins, respectively.

Recombinant: A recombinant nucleic acid, protein or virus is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, for example, by genetic engineering techniques. In some examples, the recombinant rotavirus comprises one or more deletions in a viral virulence factor, such as NSs. In other examples, the recombinant viruses include a heterologous gene, such as a reporter gene.

Reporter gene: A reporter gene is a gene operably linked to another gene or nucleic acid sequence of interest (such as a promoter sequence). Reporter genes are used to determine whether the gene or nucleic acid of interest is expressed in a cell or has been activated in a cell. Reporter genes typically have easily identifiable characteristics, such as fluorescence, or easily assayed products, such as an enzyme. Reporter genes can also confer antibiotic resistance to a host cell or tissue. Reporter genes include, for example, labels such as green fluorescent protein (GFP or eGFP) or other fluorescence genes, luciferase, β-galactosidase and alkaline phosphatase.

Rotavirus: A double stranded RNA virus; the genome of a rotavirus consists of 11 unique double helix molecules of RNA which are 18,555 nucleotides in total. Each helix, or segment, is a gene, numbered 1 to 11 by decreasing size. Each gene codes for one protein, except genes 11, which codes for two proteins. There are eight species of rotavirus, referred to as A, B, C, D, E, F, G, and H. Humans are primarily infected by species A, B, C and H, most commonly by species A. The A-E species cause disease in other animals. Within rotavirus A there are different strains, called serotypes. There are six viral proteins (VPs) that form the virus particle (virion). These structural proteins are called VP1, VP2, VP3, VP4, VP6 and VP7. In addition to the VPs, there are six nonstructural proteins (NSPs), that are only produced in cells infected by rotavirus. These are called NSP1, NSP2, NSP3, NSP4, NSPS and NSP6. The glycoprotein VP7 defines the G serotypes and the protease-sensitive protein VP4 defines P serotypes. Wild-type rotaviruses replicate mainly in the gut, and infect enterocytes of the villi of the small intestine, leading to structural and functional changes of the epithelium. Two well-known rotavirus A prototype strains are Wa (G1-P[8]-I1-R1-C1-M1-A1-N1-T1-E1-H1) and DS-1 (G2-P[4]-I2-R2-C2-M2-A2-N2-T2-E2-H2). Rotavirus A strains G1P[8], G3P[8], G4P[8], and G9P[8] are pure Wa genogroup members because they have a Wa-like constellation (Gx-P[x]-I1-R1-C1-M1-A1-N1-T1-E1-H1) composed of genotype 1 genes; G2P[4] is a pure DS-1 genogroup member because it has a DS-1-like constellation (Gx-P[x]-I2-R2-C2-M2-A2-N2-T2-E2-H2) composed of genotype 2 genes. The segmented nature of rotavirus A genomes enables them to undergo gene reassortment during co-infection in 1 cell, leading to the emergence of progeny viruses containing mixed segments from ≥2 different parental strains. However, some human rotavirus G/P-types have a purely Wa-like or a DS-1-like genome constellation.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a given gene or protein will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237-244, 1988; Higgins and Sharp, *CABIOS* 5:151-153, 1989; Corpet et al., *Nucleic Acids Research* 16:10881-10890, 1988; and Pearson and Lipman, *Proc. Natl. Acad. Sci. U.S.A.* 85:2444, 1988. Altschul et al., *Nature Genet.* 6:119-129, 1994.

The NCBI Basic Local Alignment Search Tool (BLAST™) (Altschul et al., *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx.

In some embodiments herein, provided are nucleotide or amino acid sequences at least 80%, at least 85%, at least 90%, at least 95%, at least 96%, at least 97%, at least 98% or at least 99% identical to any one of SEQ ID NOs: 1-10.

Subject: Living multi-cellular vertebrate organisms, a category that includes both human and non-human mammals.

Therapeutically effective amount: A quantity of a specified agent sufficient to achieve a desired effect in a subject being treated with that agent. For example, this may be the amount of an attenuated rotavirus useful for eliciting an immune response in a subject and/or for preventing infection by a rotavirus. Ideally, in the context of the present disclosure, a therapeutically effective amount of an attenuated rotavirus is an amount sufficient to increase resistance to, prevent, ameliorate, and/or treat infection caused by a rotavirus a subject without causing a substantial deleterious effects in the subject. The effective amount of an attenuated rotavirus useful for increasing resistance to, preventing, ameliorating, and/or treating infection in a subject will be dependent on, for example, the subject being treated, the manner of administration of the therapeutic composition and other factors.

Vaccine: A preparation of immunogenic material capable of stimulating an immune response, administered for the prevention, amelioration, or treatment of infectious or other types of disease. The immunogenic material may include attenuated or killed microorganisms (such as attenuated viruses), antigenic proteins, peptides or DNA encoding an antigenic protein or peptide. Vaccines may elicit both prophylactic (preventative) and therapeutic responses. Methods of administration vary according to the vaccine, but may include inoculation, ingestion, inhalation or other forms of administration. Inoculations can be delivered by any of a number of routes, including parenteral, such as intravenous, subcutaneous or intramuscular. Vaccines may be administered with an adjuvant to boost the immune response.

Vector: A nucleic acid molecule as introduced into a host cell, thereby producing a transformed host cell. A vector may include nucleic acid sequences that permit it to replicate in a host cell, such as an origin of replication (DNA sequences that participate in initiating DNA synthesis). A vector may also include one or more selectable marker genes and other genetic elements known in the art.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. All GENBANK® Accession numbers are incorporated by reference herein as they appear in the database on Apr. 19, 2013. In case of conflict, the present specification, including explanations of terms, will control. In addition, the materials, methods, and examples are illustrative only and not intended to be limiting.

Immunogenic Compositions

Attenuated forms of G9P[6] rotaviruses have not been previously produced or identified. An attenuated rotavirus is particularly advantageous because it can be used to induce an immune response, while not causing diarrhea. This type of rotavirus is also advantageous because the immune response can be directed to DS-1 like viruses. In a specific non-limiting example, the attenuated G9P[6] rotavirus is CDC-6, that is non-naturally occurring. Compositions can be produced including an attenuated G9P[6] rotavirus that can be used as vaccines, such as to produce an immune response to Wa (genogroup 1) and/or DS-1 (genogroup2) rotaviruses.

In some embodiments the attenuated G9P[6] rotavirus can be included in a pharmaceutical composition and can be used to induce an immune response to a rotavirus. In some embodiments, the attenuated G9P[6] rotavirus grows to a titer of at least about $10^7$ to about $10^8$ when propagated in host cells in vitro. Higher titers are contemplated.

In some embodiments, the disclosed attenuated G9P[6] rotavirus can be used to induce an immune response to a G9P[6] rotavirus, such as a protective immune response. The attenuated G9P[6] rotavirus can be used to induce an immune response to more than one type rotavirus, such as the DS-1 like strains. In additional embodiments, the rotavirus can be used to induce an immune response to at least a G9P[6] rotavirus and a G1P[8] rotavirus. In further embodiments, the rotavirus can be used to induce an immune response to at least a G2P[4] rotavirus and a G1P[8] rotavirus.

A rotavirus includes 11 RNA segments (nucleic acid molecules) encoding a VP1, VP2, VP3, VP4, NSP1, NSP1, NSP3, NSPS and NSP4 polypeptides. The function and active domains of these proteins are known in the art, see, for example, Prasad B V, Chiu W (1994), *Curr. Top. Microbiol. Immunol.* 185: 9-29; Patton J T (1995) *Gen. Virol.* 76 (11): 2633-44; and Pesavento et al., (2006), *Curr. Top. Microbiol. Immunol.* 309: 189-219, all incorporated by reference herein. In a specific non-limiting example, the attenuated rotavirus. It should be noted that in this context, for any of the G9P[6] polypeptides or polynucleotides, "about" for a percentage identity indicates within 0.05%.

In some embodiments, the attenuated G9P[6] rotavirus includes a nucleic acid molecule encoding a VP1 polypeptide comprising an amino acid sequence at least about 99.8% identical, or at least about 99.9% identical, to the amino acid sequence set forth as SEQ ID NO: 1. In a specific non-limiting example, the rotavirus includes a nucleic acid sequence encoding a VP1 polypeptide comprising the amino acid sequence set forth as SEQ ID NO: 1. In additional embodiments, the rotavirus includes a VP1 nucleic acid sequence at least about 99.7% identical, at least about 99.8% identical, or at least about 99.9% identical, to the nucleic acid sequence set forth as SEQ ID NO: 12. In a specific non-limiting example, the rotavirus includes the nucleic sequence set forth as SEQ ID NO: 12. In other embodiments, the rotavirus includes a VP1 polypeptide at least about 99.8% identical, or at least about 99.9% identical, to the amino acid sequence set forth as SEQ ID NO: 1. In a specific non-limiting example, the rotavirus includes a VP1 polypeptide including the amino acid sequence set forth as SEQ ID NO: 1.

In some embodiments, the attenuated G9P[6] rotavirus includes a nucleic acid molecule encoding a VP2 polypeptide comprising the amino acid sequence set forth as SEQ ID NO: 2. In additional embodiments, the rotavirus includes a VP2 nucleic acid sequence at least about 99.5% identical, at least about 99.6% identical, at least about 99.7% identical, at least about 99.8% identical, or at least about 99.9% identical to the nucleic acid sequence set forth as SEQ ID NO: 13. In a specific non-limiting example, the rotavirus includes the nucleic acid sequence set forth as SEQ ID NO: 13. In other embodiments, the rotavirus includes a VP2 polypeptide comprising the amino acid sequence set forth as SEQ ID NO: 2.

In some embodiments, the attenuated G9P[6] rotavirus includes a nucleic acid molecule encoding a VP3 polypeptide comprising an amino acid sequence at least about 99.6% identical, at least 99.7% identical, at least 99.8% identical, or at least about 99.9% identical, to the amino acid sequence set forth as SEQ ID NO: 3. In a specific non-limiting example, the rotavirus includes a nucleic acid sequence encoding a VP3 polypeptide comprising the amino acid sequence set forth as SEQ ID NO: 3. In additional embodiments, the rotavirus includes a VP3 nucleic acid sequence at least about 99.4% identical, about 99.5% identical, about 99.6% identical, about 99.7% identical, at least about 99.8% identical, or at least about 99.9% identical, to the nucleic acid sequence set forth as SEQ ID NO: 14. In a specific non-limiting example, the rotavirus includes the nucleic sequence set forth as SEQ ID NO: 14. In other embodiments, the rotavirus includes a VP3 polypeptide at least about 99.6% identical, about 99.7% identical, about 99.8% identical, or at least about 99.9% identical, to the amino acid sequence set forth as SEQ ID NO: 3. In a specific non-limiting example, the rotavirus includes a VP3 polypeptide comprising the amino acid sequence set forth as SEQ ID NO: 3.

In some embodiments, the attenuated G9P[6] rotavirus includes a nucleic acid molecule encoding a VP4 polypeptide comprising an amino acid sequence at least about 99.1% identical, at least about 99.2% identical, at least about 99.3% identical, at least about 99.4% identical, at least about 99.5% identical, at least about 99.6% identical, at least 99.7% identical, at least 99.8% identical, or at least about 99.9% identical, to the amino acid sequence set forth as SEQ ID NO: 4. In a specific non-limiting example, the rotavirus includes a nucleic acid sequence encoding a VP4 polypeptide comprising the amino acid sequence set forth as SEQ ID NO: 4. In additional embodiments, the rotavirus includes a VP4 nucleic acid sequence at least about 99.2% identical, at least about 99.3% identical, at least about 99.4% identical, about 99.5% identical, about 99.6% identical, about 99.7% identical, at least about 99.8% identical, or at least about 99.9% identical, to the nucleic acid sequence set forth as SEQ ID NO: 15. In a specific non-limiting example, the rotavirus includes the nucleic sequence set forth as SEQ ID NO: 15. In other embodiments, the rotavirus includes a VP4 polypeptide at least about 99.1% identical, at least about 99.2% identical, at least about 99.3% identical, at least about 99.4% identical, at least about 99.5% identical, at least about 99.6% identical, at least 99.7% identical, at least 99.8% identical, or at least about 99.9% identical, to the amino acid sequence set forth as SEQ ID NO: 4. In a specific non-limiting example, the rotavirus includes a VP4 polypeptide comprising the amino acid sequence set forth as SEQ ID NO: 4.

In some embodiments, the attenuated G9P[6] rotavirus includes a nucleic acid molecule encoding a VP6 polypeptide comprising the amino acid sequence set forth as SEQ ID NO: 5. In additional embodiments, the rotavirus includes a VP6 nucleic acid sequence at least about 99.7% identical, at least about 99.8% identical, or at least about 99.9% identical to the nucleic acid sequence set forth as SEQ ID NO: 16. In a specific non-limiting example, embodiments, the rotavirus includes the nucleic acid sequence set forth as SEQ ID NO: 16. In other embodiments, the rotavirus includes a VP6 polypeptide comprising the amino acid sequence set forth as SEQ ID NO: 5.

In some embodiments, the attenuated G9P[6] rotavirus includes a nucleic acid molecule encoding a VP7 polypeptide comprising an amino acid sequence at least about 98.9% identical, at least about 99.0% identical, at least about 99.1% identical, at least about 99.2% identical, at least about 99.3% identical, at least about 99.4% identical, at least about 99.5% identical, at least about 99.6% identical, at least 99.7% identical, at least 99.8% identical, or at least about 99.9% identical, to the amino acid sequence set forth as SEQ ID NO: 6. In a specific non-limiting example, the rotavirus includes a nucleic acid sequence encoding a VP7 polypeptide comprising the amino acid sequence set forth as SEQ ID NO: 6. In additional embodiments, the rotavirus includes a VP7 nucleic acid sequence at least about 99.4% identical, about 99.5% identical, about 99.6% identical, about 99.7% identical, at least about 99.8% identical, or at least about 99.9% identical, to the nucleic acid sequence set forth as SEQ ID NO: 17. In a specific non-limiting example, the rotavirus includes the nucleic sequence set forth as SEQ ID NO: 17. In other embodiments, the rotavirus includes a VP7 polypeptide at least about 98.9% identical, at least about 99.0% identical, at least about 99.1% identical, at least about 99.2% identical, at least about 99.3% identical, at least about 99.4% identical, at least about 99.5% identical, at least about 99.6% identical, at least 99.7% identical, at least 99.8% identical, or at least about 99.9% identical, to the amino acid sequence set forth as SEQ ID NO: 6. In a specific non-limiting example, the rotavirus includes a VP7 polypeptide comprising the amino acid sequence set forth as SEQ ID NO: 6.

In some embodiments, the attenuated G9P[6] rotavirus includes a nucleic acid molecule encoding an NSP1 polypeptide comprising an amino acid sequence at least about 98.9% identical, at least about 99.0% identical, at least about 99.1% identical, at least about 99.2% identical, at least about 99.3% identical, at least about 99.4% identical, at least about 99.5% identical, at least about 99.6% identical, at least 99.7% identical, at least 99.8% identical, or at least about 99.9% identical, to the amino acid sequence set forth as SEQ ID NO: 7. In a specific non-limiting example, the rotavirus includes a nucleic acid sequence encoding a NSP1 polypeptide comprising the amino acid sequence set forth as SEQ ID NO: 7. In additional embodiments, the rotavirus includes a NSP1 nucleic acid sequence at least about at least about 99.2% identical, at least 99.3% identical, at least 99.4% identical, about 99.5% identical, about 99.6% identical, about 99.7% identical, at least about 99.8% identical, or at least about 99.9% identical, to the nucleic acid sequence set forth as SEQ ID NO: 18. In a specific non-limiting example, the rotavirus includes the nucleic sequence set forth as SEQ ID NO: 18. In other embodiments, the rotavirus includes a NSP1 polypeptide at least about 98.9% identical, at least about 99.0% identical, at least about 99.1% identical, at least about 99.2% identical, at least about 99.3% identical, at least about 99.4% identical, at least about 99.5% identical, at least about 99.6% identical, at least 99.7% identical, at least 99.8% identical, or at least about 99.9% identical, to the amino acid sequence set forth as SEQ ID NO: 7. In a specific non-limiting example, the rotavirus includes a NSP1 polypeptide comprising the amino acid sequence set forth as SEQ ID NO: 7.

In some embodiments, the attenuated G9P[6] rotavirus includes a nucleic acid molecule encoding a NSP2 polypeptide comprising the amino acid sequence set forth as SEQ ID NO: 8. In additional embodiments, the rotavirus includes a NSP2 nucleic acid sequence at least about 99.8% identical, or at least about 99.9% identical to the nucleic acid sequence set forth as SEQ ID NO: 19. In a specific non-limiting example, embodiments, the rotavirus includes the nucleic acid sequence set forth as SEQ ID NO: 19. In other embodiments, the rotavirus includes a NSP2 polypeptide comprising the amino acid sequence set forth as SEQ ID NO: 8.

In some embodiments, the attenuated G9P[6] rotavirus includes a nucleic acid molecule encoding a NSP3 polypeptide comprising an amino acid sequence at least about 99.8% identical, or at least about 99.9% identical, to the amino acid sequence set forth as SEQ ID NO: 9. In a specific non-limiting example, the rotavirus includes a nucleic acid sequence encoding a NSP3 polypeptide comprising the amino acid sequence set forth as SEQ ID NO: 9. In additional embodiments, the rotavirus includes a NSP3 nucleic acid sequence at least about 99.3% identical, at least about 99.4% identical, at least about 99.5% identical, at least about 99.6% identical, at least 99.7% identical, at least 99.8% identical, or at least about 99.9% identical, to the nucleic acid sequence set forth as SEQ ID NO: 20. In a specific non-limiting example, the rotavirus includes the nucleic sequence set forth as SEQ ID NO: 20. In other embodiments, the rotavirus includes a NSP3 polypeptide at least about 99.8% identical, or at least about 99.9% identical, to the amino acid sequence set forth as SEQ ID NO: 9. In a specific non-limiting example, the rotavirus includes a NSP3 polypeptide comprising the amino acid sequence set forth as SEQ ID NO: 9.

In some embodiments, the attenuated G9P[6] rotavirus includes a nucleic acid molecule encoding a NSP4 polypeptide comprising the amino acid sequence set forth as SEQ ID NO: 10. In additional embodiments, the rotavirus includes a NSP4 nucleic acid sequence at least about 99.2% identical, at least 99.3% identical, at least 99.4% identical, about 99.5% identical, about 99.6% identical, about 99.7% identical, at least about 99.8% identical, or at least about 99.9% identical, to the nucleic acid sequence set forth as SEQ ID NO: 21. In a specific non-limiting example, embodiments, the rotavirus includes the nucleic acid sequence set forth as SEQ ID NO: 21. In other embodiments, the rotavirus includes a NSP4 polypeptide comprising the amino acid sequence set forth as SEQ ID NO: 10.

In some embodiments, the attenuated G9P[6] rotavirus includes a nucleic acid molecule encoding a NSPS polypeptide comprising an amino acid sequence at least about 99.6% identical, at least 99.7% identical, at least 99.8% identical, or at least about 99.9% identical, to the amino acid sequence set forth as SEQ ID NO: 11. In a specific non-limiting example, the rotavirus includes a nucleic acid sequence encoding a NSPS polypeptide comprising the amino acid sequence set forth as SEQ ID NO: 11. In additional embodiments, the rotavirus includes a NSPS nucleic acid sequence at least about 99.6% identical, about 99.7% identical, at least about 99.8% identical, or at least about 99.9% identical, to the nucleic acid sequence set forth as SEQ ID NO: 22. In a specific non-limiting example, the rotavirus includes the nucleic sequence set forth as SEQ ID NO: 22. In other embodiments, the rotavirus includes a NSPS polypeptide at least about 99.6% identical, about 99.7% identical, about 99.8% identical, or at least about 99.9% identical, to the amino acid sequence set forth as SEQ ID NO: 11. In a specific non-limiting example, the rotavirus includes a NSPS polypeptide comprising the amino acid sequence set forth as SEQ ID NO: 11.

In some embodiments, the attenuated G9P[6] rotavirus includes a) a nucleic acid molecule encoding a polypeptide comprising an amino acid sequence at least 99.8% identical to the amino acid sequence set forth as SEQ ID NO: 1 (VP1); b) a nucleic acid molecule encoding a polypeptide comprising an amino acid sequence set forth as SEQ ID NO: 2 (VP2); c) a nucleic acid molecule encoding a polypeptide comprising an amino acid sequence at least 99.6% identical to the amino acid sequence set forth as SEQ ID NO: 3 (VP3); d) a nucleic acid molecule encoding a polypeptide comprising an amino acid sequence at least 99.1% identical to the amino acid sequence set forth as SEQ ID NO: 4 (VP4); e) a nucleic acid molecule encoding a polypeptide comprising an amino acid sequence set forth as SEQ ID NO: 5 (VP6); f) a nucleic acid molecule encoding a polypeptide comprising an amino acid sequence at least 98.9% identical to the amino acid sequence set forth as SEQ ID NO: 6 (VP7); h) a nucleic acid molecule encoding a polypeptide comprising an amino acid sequence at least 98.9% identical to the amino acid sequence set forth as SEQ ID NO: 7 (NSP1); i) a nucleic acid molecule encoding a polypeptide comprising an amino acid sequence set forth as SEQ ID NO: 8 (NSP2); j) a nucleic acid molecule encoding a polypeptide comprising an amino acid sequence at least 98.8% identical to the amino acid sequence set forth as SEQ ID NO: 9 (NSP3); k) a nucleic acid molecule encoding a polypeptide comprising an amino acid sequence set forth as SEQ ID NO: 10 (NSP4); and 1) a nucleic acid molecule encoding a polypeptide comprising an amino acid sequence at least 99.6% identical to the amino acid sequence set forth as SEQ ID NO: 11 (NSPS). This rotavirus can include comprising one, two, three, four or all of: a) a nucleic acid molecule encoding a polypeptide comprising the amino acid sequence set forth as SEQ ID NO: 1 (VP1); b) a nucleic acid molecule encoding a polypeptide comprising the amino acid sequence set forth as SEQ ID NO: 4 (VP4); c) a nucleic acid encoding a polypeptide comprising the amino acid sequence set forth as SEQ ID NO: 6 (VP7); d) a nucleic acid molecule encoding a polypeptide comprising the amino acid sequence set forth as SEQ ID NO: 8 (NSP1); and e) a nucleic acid molecule encoding a polypeptide comprising the amino acid sequence set forth as SEQ ID NO: 10 (NSP3).

In some embodiments, the attenuated G9P[6] rotavirus includes a) a nucleic acid molecule encoding a polypeptide including the amino acid sequence set forth as SEQ ID NO: 1 (VP1); b) a nucleic acid molecule encoding a polypeptide including the amino acid sequence set forth as SEQ ID NO: 2 (VP2); c) a nucleic acid molecule encoding a polypeptide including the amino acid sequence set forth as SEQ ID NO: 3 (VP3); d) a nucleic acid molecule encoding a polypeptide including the amino acid sequence set forth as SEQ ID NO: 4 (VP4) e) a nucleic acid molecule encoding a polypeptide including the amino acid sequence set forth as SEQ ID NO: 5 (VP6); f) a nucleic acid molecule encoding a polypeptide including the amino acid sequence set forth as SEQ ID NO: 6 (VP7); h) a nucleic acid molecule encoding a polypeptide including the amino acid sequence set forth as SEQ ID NO: 7 (NSP1); i) a nucleic acid molecule encoding a polypeptide including the amino acid sequence set forth as SEQ ID NO: 8 (NSP2); j) a nucleic acid molecule encoding a polypeptide including the amino acid sequence set forth as SEQ ID NO: 9 (NSP3); k) a nucleic acid molecule encoding a polypeptide including the amino acid sequence set forth as SEQ ID NO: 10 (NSP4); and 1) a nucleic acid molecule encoding a polypeptide including the amino acid sequence set forth as SEQ ID NO: 11 (NSP5).

In further embodiments, the attenuated G9P[6] rotavirus includes a) a polypeptide including the amino acid sequence set forth as SEQ ID NO: 1 (VP1); b) a polypeptide including the amino acid sequence set forth as SEQ ID NO: 2 (VP2); c) a polypeptide including the amino acid sequence set forth as SEQ ID NO: 3 (VP3); d) a polypeptide including the amino acid sequence set forth as SEQ ID NO: 4 (VP4) e) a polypeptide including the amino acid sequence set forth as SEQ ID NO: 5 (VP6); f) a polypeptide including the amino acid sequence set forth as SEQ ID NO: 6 (VP7); h) a polypeptide including the amino acid sequence set forth as SEQ ID NO: 7 (NSP1); i) a polypeptide including the amino acid sequence set forth as SEQ ID NO: 8 (NSP2); j) a polypeptide including the amino acid sequence set forth as SEQ ID NO: 9 (NSP3); k) a polypeptide including the amino acid sequence set forth as SEQ ID NO: 10 (NSP4); and 1) a polypeptide including the amino acid sequence set forth as SEQ ID NO: 11 (NSP5).

The disclosed rotaviruses generally include a nucleic acid molecule, e.g. an RNA, encoding the rotavirus proteins. In some embodiments, the attenuated G9P[6] rotavirus is CDC-6.

Suitable pharmaceutical carriers for use with the attenuated G9P[6] rotavirus include those known in the art as being suitable for oral administration, especially to children of less than five years of age, or less than one year of age. Such carriers include and are not limited to carbohydrates, polyalcohols, amino acids, aluminium hydroxide, magnesium hydroxide, hydroxyapatite, talc, titanium oxide, iron hydroxide, magnesium stearate, carboxymethylcellulose, hydroxypropylmethylcellulose, microcrystalline cellulose, gelatin, vegetal peptone, xanthane, caraghenane, arabic gum, β-cyclodextrin. Also provided vaccines prepared by freeze drying the virus in the presence of suitable stabilizer. The pharmaceutical compositions can be formulated for systemic administration or local administration. In one embodiment, the pharmaceutical composition is formulated for oral administration. Optionally, an adjuvant can be included. The adjuvant can be an aluminum adjuvant, such as aluminum salt, aluminum phosphate, or aluminum hydroxide. The adjuvant can be a biological molecule, such as an immunostimulatory nucleic acid or a cytokine. Suitable adjuvants are disclosed above.

In some embodiments, the attenuated G9P[6] rotavirus is also inactivated, such as by heat inactivation methods for heat inactivation are disclosed, for example, in PCT Publication No. WO2009/032913, which is incorporated herein by reference.

Pharmaceutical compositions and vaccines can also contain other compounds, which can be biologically active or inactive. For example, one or more immunogenic portions of other antigens can be present, either incorporated into a fusion polypeptide or as a separate compound, within the composition or vaccine. In some embodiments, and additional rotavirus can be included, such as but not limited to, a live or an inactivated G1P[8] rotavirus, such as a heat inactivated G1P[8] rotavirus. As noted above, methods for heat inactivation are disclosed, for example, in PCT Publication No. WO2009/032913. In some embodiments, the present attenuated G9P[6] rotavirus is combined with ROTATEQ® or ROTARIX®. In additional embodiments, the present attenuated G9P[6] rotavirus is combined with CDC-9, or an variant thereof, see PCT Publication No. WO 2010/132561, which is incorporated herein by reference. The G1P[8] rotavirus, such as CDC-9 can be attenuated and/or inactivated. These pharmaceutical compositions can generally be used for prophylactic and therapeutic purposes. These pharmaceutical compositions can be formulated for oral or parenteral administration.

The inactivated attenuated rotavirus can also be included in pharmaceutical compositions to induce a response to other pathogens, such as diphtheria, tetanus, pertussis, *Haemophilus influenzae* type b, hepatitis B (HBV), polio and/or pneumococcal disease. Thus, it can be included with DTaP, Hib, Hepatitis B, polio, and/or PCV-13, such as multiple vaccine VIS. In some embodiments, the disclosed attenuated G9P[6] rotavirus can be combined with IPV as a bivalent vaccine, or with penta (DT, whole cell pertussis, Hib, hepatitis B virus (HBV)) as a hexavalent vaccine. Optionally, an inactivated G1P[8] rotavirus, such as, but not limited to, CDC-9, can also be included in the composition. The G1P[8] rotavirus can be attenuated and/or inactivated. In some embodiments, these pharmaceutical compositions can be used for prophylactic purposes.

The inactivated attenuated G9P[6] rotavirus can be formulated in lipid-based vehicles such as virosomes or liposomes, in oil in water emulsions or with carrier particles. Alternatively or in addition, immunostimulants, such as those known in the art for oral vaccines may be included in the formulation. Such immunostimulants include bacterial toxins, particularly cholera toxin (CT) in the form of the holotoxin (entire molecule) or the B chain only (CTB) and the heat labile enterotoxin of *E. coli* (LT). Mutated LTs (mLTs) which are less likely to convert to their active form than the native LT, see PCT Publication No. WO 96/06627, PCT Publication No. WO 93/13202 and U.S. Pat. No. 5,182,109. These compositions can be formulated for parenteral delivery with or without an adjuvant.

In some embodiments, saponin derivatives can be included such as QS21 and monophosphoryl lipid A, in particular 3-de-O-acylated monophosphoryl lipid A (3D-MPL). Purified saponins for use as oral adjuvants are disclosed in PCT Publication No. WO 98/56415. Saponins and monophosphoryl lipid A can be used, see PCT Publication No. WO 94/00153, and can be formulated in adjuvant systems together with other agents. 3D-MPL is a well-known adjuvant manufactured by Ribi Immunochem, Montana and its manufacture is described in GB 2122204. Vehicles and adjuvants re also disclosed in Vaccine Design, The Subunit and Adjuvant Approach, edited by Powell and Newman, Plenum Press, New York, 1995. These compositions can be formulated for parenteral delivery.

For oral formulations, the attenuated G9P[6] rotavirus can be formulated with an antacid to minimize inactivation of the vaccine by acid in the stomach. Suitable antacid components include inorganic antacids for example aluminium hydroxide $Al(OH)_3$ and magnesium hydroxide $Mg(OH)_2$. Commercially available antacids which are suitable for use include both aluminium hydroxide and magnesium hydroxide, which are insoluble in water but can be provided in suspension. Aluminium hydroxide also can be used as an adjuvant. Organic acid carboxylate salts can also be included in the composition. Non-limiting examples are a salt of citric acid such as sodium citrate or potassium citrate. In one non-limiting example, the insoluble inorganic salt, calcium carbonate ($CaCO_3$) can be utilized. Calcium carbonate is able to associate with a rotavirus and activity is maintained. In addition, sodium bicarbonate can be included.

In some embodiments, to prevent sedimentation of calcium carbonate during the filling step, viscous agents are suitably present in the formulation. Viscous agents include pseudoplastic excipients. A pseudoplastic solution is defined as a solution having higher viscosity on standing compared to its viscosity under agitation. Excipients of this type are natural polymers such as arabic gum, adragante gum, agar-agar, alginates, pectines or semi-synthetic polymers for example: carboxymethylcellulose (TYLOSES®), methylcellulose (METHOCELS A®, VISCOTRANS MC® and TYLOSE MH®) hydroxypropylcellulose (KLUCELS®), and hydroxypropylmethylcellulose (METHOCELS E® and K®, VISCONTRANS MPHC®). In general the pseudoplastic excipients is used together with thixotropic agents.

Alternative viscous agents that may be used are pseudoplastic excipients with low flowing capacity. Those polymers, at a sufficient concentration, give rise to a structural fluid arrangement resulting in a high viscosity solution having low flowing capacity on standing. A certain quantity of energy needs to be given to the system to allow flowing and transfer. Agitation can be needed to destroy temporarily the structural fluid arrangement in order to obtain a fluid solution. Examples of such polymers are CARBOPOLS® and xanthan gum.

Thixotropic excipients become a gel structure on standing whilst under agitation they form a fluid solution. Examples of thixotropic excipients are: VEEGUM® (Magnesium-aluminium silicate) and AVICEL RC® (about 89% microcrystalline cellulose and 11% Carboxymethylcellulose Na).

In some embodiments, the pharmaceutical composition includes a viscous agent selected from xanthan gum or starch. The composition can include a combination of calcium carbonate and xanthan gum.

Other components include sugars for example sucrose and/or lactose. The composition can include additional components including for example flavorings (particularly for an oral vaccine) and bacteriostatic agents.

In one suitable embodiment, the pharmaceutical composition is administered as a liquid formulation. Suitably the liquid formulation is reconstituted prior to administration from at least the following two components: i) virus component ii) liquid component. In this embodiment, the virus component and the liquid component are normally present in separate containers, which may conveniently be separate compartments of a single vessel, or separate vessels which can be connected in such a way that the final vaccine composition is reconstituted without exposing it to the air.

Prior to reconstitution, the virus can be in a dry form or a liquid form. Suitably the virus component is lyophilized. Lyophilized virus can be more stable than virus in an aqueous solution. The lyophilized virus may be suitably reconstituted using a liquid antacid composition to produce a liquid vaccine formulation. Alternatively the lyophilized virus may be reconstituted with water or aqueous solution, in which case the lyophilized virus composition can contain an antacid component. In some embodiments, the virus component is formulated with calcium carbonate and xanthane gum in one compartment or vessel and this is reconstituted with water or aqueous solution present in the second compartment or vessel. In another embodiment, the composition is a solid formulation, suitably a lyophilized cake which is suitable for immediate dissolution when placed in the mouth.

Lyophilized formulations may conveniently be provided in the form of tablets in a pharmaceutical blister pack. An attenuated G9P[6] rotavirus can be provided in the form of a quick dissolving tablet for oral administration. Thus the composition can include a live attenuated rotavirus strain, in particular an attenuated G9P[6] rotavirus strain, wherein the composition is a lyophilized solid capable of immediate dissolution when placed in the mouth. The rotavirus can be provided in a quick dissolving tablet that dissolves in the mouth of the subject sufficiently quickly to prevent swallowing of the undissolved tablet. This approach is particularly advantageous for pediatric rotavirus vaccines.

Thus, formulations suitable for oral administration can include or consists of (a) liquid solutions, such as an effective amount suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Aerosol formulations (i.e., they can be "nebulized") can be administered via inhalation. Aerosol formulations can be placed into pressurized acceptable propellants, such as dichlorodifluoromethane, propane, nitrogen, and the like.

Formulations suitable for parenteral administration, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Compositions can be administered, for example, by intravenous infusion, inhalation, parenterally, orally, topically, intradermally, intraperitoneally, intravenously, intravesically, rectally or intrathecally. The formulations can be presented in unit-dose or multi-dose sealed containers, such as ampules and vials. Pharmaceutically acceptable carriers are determined in part by the particular composition being administered (e.g., nucleic acid, protein, modulatory compounds or transduced cell), as well as by the particular method used to administer the composition. Accordingly, there are a wide variety of suitable formulations of pharmaceutical compositions of the present invention (see, e.g., *Remington's Pharmaceutical Sciences*, $17^{th}$ ed., 1989).

For any route of administration, the compositions can include buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention can be formulated as a lyophilizate.

Injection solutions and suspensions can be prepared from sterile powders, granules, and tablets of the kind previously described. The disclosed compositions can be administered parenterally.

The dose administered to a subject should be sufficient to affect a beneficial immune response in the subject. The dose will be determined by the efficacy of the particular composition employed and the condition of the subject, as well as the body weight or surface area of the subject to be treated. The size of the dose also will be determined by the existence, nature, and extent of any adverse side-effects that accompany the administration of a particular vector, or transduced cell type in a particular patient. Administration can be accomplished via single or divided doses.

Immunogenic compositions such as vaccines can be formulated and administered by known techniques, using a suitable amount of live virus to provide effective protection against rotavirus infection without significant adverse side effects in typical vaccines. A suitable amount of live virus can be between $10^4$ and $10^8$ focus forming units (ffu), such as between $10^4$ and $10^7$ per dose. A typical dose of vaccine may comprise $10^5$-$10^6$ ffu per dose and may be given in several doses over a period of time, for example in two doses given with a two-month interval. Thus, the composition can be given in a prime boost strategy. Benefits may however be obtained by having more than 2 doses, for example a 3 or 4 dose regimen, particularly in developing countries. The interval between doses may be more or less than two months long. An optimal amount of live virus for a single dose compositions, or for multiple dose kits, and optimal timing for the doses, can be ascertained by standard studies involving observation of antibody titers and other responses in subjects.

Methods for Inducing an Immune Response

Methods are disclosed herein for inducing an immune response to a rotavirus. The methods include administering a pharmaceutical composition as disclosed herein. The administration of the immunogenic compositions can be for either prophylactic or therapeutic purpose. When provided prophylactically, the immunogenic composition is provided in advance of any symptom, for example in advance of infection with a rotavirus. The prophylactic administration of the immunogenic compositions serves to prevent or ameliorate any subsequent infection. The immunogenic composition can thus be provided prior to the anticipated exposure to rotavirus so as to attenuate the anticipated severity, duration or extent of an infection and/or associated disease symptoms, after exposure or suspected exposure to the virus, or after the actual initiation of an infection. Thus, the methods can induce a protective immune response. In some embodiments, a therapeutically effective amount can decrease or eliminate symptoms, such as diarrhea, from a subsequent exposure to a rotavirus.

A subject can be selected for treatment that has, or is at risk for developing rotavirus infection, for example because of exposure or the possibility of exposure to a rotavirus. Following administration of a disclosed immunogen, the subject can be monitored for rotaviral infection or symptoms associated therewith, or both.

When provided therapeutically, the immunogenic composition is provided at or after the onset of a symptom of disease or infection, for example after development of a symptom of a rotavirus infection, or after diagnosis of a rotavirus infection. A therapeutically effective amount of the disclosed immunogenic compositions is that which provides either subjective relief of a symptom(s) or an objectively identifiable improvement as noted by the clinician or other qualified observer.

The subject can be any subject of interest, such as a human or a veterinary subject. In some embodiments, the subject does not have a rotavirus infection, such as a healthy subject. In some non-limiting examples, the subject is a human, such as a human child. The human child can be less than 5 years of age, such as less than one year of age. In some non-limiting examples, vaccination can occur at birth, about 1 to 2 months of age, about 4 months of age, about 6 months of age, from about 6 months to 18 months of age, from 12 to 15 months of age. In some embodiments, two to three doses are administered before six months of age. Optionally, one or more boost doses between six and 18 months of age is also administered. Thus, several administration to a child (infant) is contemplated.

Any route of administration can be utilized as set forth above. In a specific non-limiting example, the pharmaceutical composition is administered parenterally or orally.

In particular embodiments, the composition includes least two rotavirus strains. The two or more rotavirus strains each independently have a G1, G2, G3, G4, G5, G6, G7, G8, G9, G10, G11, G12, G13 or G14 G serotype. Thus, for example, at least one of CDC-6 is present in a composition along with at least a second human rotavirus strain which has a G1, G2, G3, G4, G5, G6, G7, G8, G9, G10, G11, G12, G13 or G14G serotype. Each of the at least two rotavirus strains included in a composition has a P serotype which is P1A, P1B, P2A, P3, P4, P5, P6, P8, P11, or P12 in particular embodiments. A composition for enhancing immunological protection against a rotavirus-mediated disease in a subject includes a first human rotavirus strain characterized as having a G9 serotype and a second human rotavirus strain characterized as having a G1 serotype in particular embodiments of the composition. Each of the two rotavirus strains independently has a P group serotype, wherein the G9 virus has a P6 serotype and the other rotavirus can be a P1A, P1B, P2A, P3, P4, P5, P6, P8, P11 or P12 serotype.

In some embodiments, an attenuated or inactivated G1P [8] rotavirus is also administered to the subject. In some embodiments, the present attenuated G9P[6] rotavirus is administered with ROTATEQ®, ROTARIX®, or a CDC-9 or CDC-66 rotavirus (see PCT Publication No. WO 2010/132561, incorporated herein by reference), either simultaneously or sequentially. Provided are pharmaceutical compositions including an attenuated G9P[6] rotavirus as disclosed herein, and at least one of CDC-9 or CDC-66. Optionally, the attenuated G9P[6] rotavirus is also inactivated. The G9P[6] rotavirus can be CDC-6. These compositions can be formulated for oral or parenteral administration. CDC-9 and CDC-66 are disclosed, for example, in published U.S. Patent No. 2012/0121629, incorporated herein by reference.

The choice of live attenuated rotavirus or inactivated rotavirus depends on factors such as route of vaccine composition administration. In a particular embodiment, the composition includes a human rotavirus A strain CDC-9, and/or CDC-66, one or more rotavirus A CDC-9, and/or CDC-66 polypeptides and/or an immunogenic fragment of one or more rotavirus A CDC-9, and/or CDC-66 polypeptides. In some embodiments, inactivated CDC-9 and an inactivated G9P[6] are included and the composition is formulated for parenteral administration. This composition can include an adjuvant. In a specific non-limiting example, the G9P[6] rotavirus is CDC-6.

Administration induces a sufficient immune response to treat or prevent the pathogenic infection, for example, to inhibit the infection and/or reduce the signs and/or symptoms of the rotavirus such as diarrhea. Amounts effective for this use will depend upon the severity of the disease, the general state of the subject's health, and the robustness of the subject's immune system.

For prophylactic and therapeutic purposes, the immunogenic composition can be administered to the subject in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the immunogenic composition can be provided as repeated doses within a prolonged prophylaxis or treatment regimen that will yield clinically significant results to alleviate one or more symptoms or detectable conditions associated with a rotavirus infection. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, porcine, feline, ferret, non-human primate, and other accepted animal model subjects known in the art. Alternatively, effective dosages can be determined using in vitro models (for example, immunologic and histopathologic assays). Using such models, only ordinary calculations and adjustments are required to determine an appropriate concentration and dose to administer a therapeutically effective amount of the immunogenic composition (for example, amounts that are effective to elicit a desired immune response or alleviate one or more symptoms of a targeted disease). In alternative embodiments, an effective amount or effective dose of the immunogenic composition may inhibit or enhance one or more selected biological activities.

In one embodiment, a suitable immunization regimen includes at least two or three separate inoculations with one or more immunogenic compositions, with a second inoculation being administered more than about two, about three to eight, or about four, weeks following the first inoculation, or about 2, about 4, about 6, about 8, about 10 or about 12 months following a first inoculation. A third inoculation can be administered months after the second inoculation, such as one to two months, and in specific embodiments, more than about five months after the first inoculation, more than about six months to about two years after the first inoculation, or about eight months to about one year after the first inoculation. Periodic inoculations beyond the third also can be used to enhance the subject's "immune memory." These inoculations can be given to older children or adults.

The adequacy of the vaccination parameters chosen, e.g., formulation, dose, regimen and the like, can be determined by taking aliquots of serum from the subject and assaying antibody titers during the course of the immunization program. If such monitoring indicates that vaccination is suboptimal, the subject can be boosted with an additional dose of immunogenic composition, and the vaccination parameters can be modified in a fashion expected to potentiate the immune response. It is contemplated that there can be several boosts.

For prime-boost protocols, the prime can be administered as a single dose or multiple doses, for example two doses, three doses, four doses, five doses, six doses or more can be administered to a subject over days, weeks or months. The boost can be administered as a single dose or multiple doses, for example two to six doses, or more can be administered to a subject over a day, a week or months. Multiple boosts can also be given, such one to five, or more. Different dosages can be used in a series of sequential inoculations. For example a relatively large dose in a primary inoculation and then a boost with relatively smaller doses. The immune response against the selected antigenic surface can be generated by one or more inoculations of a subject with an immunogenic composition disclosed herein.

In some embodiments, the administration results in cross-protection. Cross-protection can be homotypic or heterotypic. Homotypic cross-protection is a protection afforded by a rotavirus strain against a strain of either a G or a P type, such as for example a G9P[6] strain affording cross-protection against a non-G9, P[6] strain (e.g. G2P[6]) via the P[6] type. Another example of a homotypic cross-protection is that afforded by a G9P[6] strain against a G9 non-P[6] strain (e.g. G9P[4]) via the G1 type. Heterotypic cross-protection is a protection afforded by a rotavirus strain against a rotavirus strain of different P and G types such as for example the protection afforded by a G9P[6] against a non G9-non P[6]-strain (e.g. G1P[8]) (heterotypic protection afforded via both G and P types). In some embodiments, the attenuated rotavirus serotype is G9 and is able to provide cross protection against disease caused by G9 and non-G9 rotavirus serotypes such as serotypes selected from the group consisting of: G1, G2, G3, G4, G5, G6, G7, G8, G10, G11, G12, G13 and G14. In additional embodiments, the rotavirus attenuated strain type is P[6] and is able to provide cross-protection against disease caused by P[6] rotavirus type and by non-P[6] rotavirus types such as types selected from the group consisting of: P[1], P[2], P[3], P[4], P[5], P[7], P[8], P[9], P[10], P[11], P[12], P[14] and P[19].

Immunity can be measured, for example, by neutralizing antibody responses to the pharmaceutical composition or by serum rotavirus IgA antibody response, such as seroconversion factor (i.e. 23-fold increase in serum antibody IgA levels following vaccination, as described in Ward et al., 1990, J. Infect. Disease, 161, 440-445). In most instances it will be sufficient to assess the antibody titer in serum or plasma obtained from the subject. Decisions as to whether to administer booster inoculations and/or to change the amount of the therapeutic agent administered to the individual can be at least partially based on the antibody titer level.

Determination of effective dosages is typically based on animal model studies followed up by human clinical trials and is guided by administration protocols that significantly reduce the occurrence or severity of targeted disease symptoms or conditions in the subject, or that induce a desired response in the subject (such as a neutralizing immune response). Suitable models in this regard include, for example, mouse, pig, non-human primate, and other accepted animal model subjects known in the art (see below). Using such models, only ordinary calculations and adjustments are required to determine an appropriate concentration and dose to administer a therapeutically effective amount of the composition (for example, amounts that are effective to elicit a desired immune response or alleviate one or more symptoms).

Methods are disclosed herein for inducing an immune response to more than one pathogen.

In some embodiments, and additional rotavirus can be included in the pharmaceutical composition. The additional rotavirus can be, but is not limited to, a live or an inactivated G1P[8] rotavirus, such as a heat inactivated G1P[8] rotavirus. As noted above, methods for heat inactivation are disclosed, for example, in PCT Publication No. WO2009/032913. In some embodiments, the present attenuated G9P[6] rotavirus is combined with ROTATEQ® or ROTARIX® and used to induce an immune response in a subject. In additional embodiments, the present attenuated G9P[6] rotavirus is combined with CDC-9, or an variant thereof, see PCT Publication No. WO 2010/132561, which is incorporated herein by reference, and used to induce an immune response in a subject. The G1P[8] rotavirus, such as CDC-9 can be attenuated and/or inactivated and administered to the subject. These pharmaceutical compositions can generally be used for prophylactic and therapeutic purposes. In some embodiments, the composition is administered orally or parenterally to the subject.

The inactivated attenuated rotavirus can also be included in pharmaceutical compositions to and used to induce a response to different pathogens, such as diphtheria, tetanus, pertussis, *Haemophilia influenzae* type b, hepatitis B (HBV), polio and/or pneumococcal disease. Thus, it can be administered with DTaP, Hib, Hepatitis B, polio, and/or PCV-13, such as multiple vaccine VIS. In some embodiments, the disclosed attenuated G9P[6] rotavirus can be combined with IPV as a bivalent vaccine, or with penta (DT, acellular or whole cell pertussis, Hib, hepatitis B virus (HBV)) as a hexavalent vaccine, and used to induce an immune response in a subject. Optionally, an inactivated G1P[8] rotavirus, such as, but not limited to, CDC-9, can also be included in the composition and administered to a subject. The G1P[8] rotavirus can be attenuated and/or inactivated. In some embodiments, a multivaccine includes with penta (DT, acellular or whole cell pertussis, Hib, hepatitis B virus (HBV)), a G1P[8] rotavirus, and a G9P[6] rotavirus, such as CDC-6. In further embodiments, a multivaccine includes with penta (DT, acellular or whole cell pertussis, Hib, hepatitis B virus (HBV)), CDC-9 and/or CDC66, and a G9P[6] rotavirus, such as CDC-6. In some embodiments, these pharmaceutical compositions can be used for prophylactic purposes. In some embodiments, the composition is administered orally or parenterally to the subject.

Nucleic Acid Molecules and Polypeptides

Isolated nucleic acid molecules and polypeptides are also provided herein. These isolated nucleic acid molecules and polypeptides can also be included in pharmaceutical compositions and used in the methods disclosed above. One or more polypeptides, or one or more polynucleotides, can be included in a pharmaceutical composition.

In some embodiments, a VP1 polypeptide is provided that includes an amino acid sequence at least about 99.8% identical, or at least about 99.9% identical, to the amino acid sequence set forth as SEQ ID NO: 1. In a specific non-limiting example, the VP1 polypeptide includes or consists of the amino acid sequence set forth as SEQ ID NO: 1. In other embodiments, a VP2 polypeptide is provided that includes or consists of the amino acid sequence set forth as SEQ ID NO: 2. In other embodiments, a VP3 polypeptide is provided that includes an amino acid sequence at least about 99.6% identical, about 99.7% identical, about 99.8% identical, or at least about 99.9% identical, to the amino acid sequence set forth as SEQ ID NO: 3. In a specific non-limiting example, the VP3 polypeptide includes or consists of the amino acid sequence set forth as SEQ ID NO: 3. In other embodiments, a VP4 polypeptide is provided that includes an amino acid sequence at least about 99.1% identical, at least about 99.2% identical, at least about 99.3% identical, at least about 99.4% identical, at least about 99.5% identical, at least about 99.6% identical, at least 99.7% identical, at least 99.8% identical, or at least about 99.9% identical, to the amino acid sequence set forth as SEQ ID NO: 4. In a specific non-limiting example, the VP4 polypeptide includes or consists of the amino acid sequence set forth as SEQ ID NO: 4. In other embodiments, the a VP6 polypeptide is provided that includes or consists of the amino acid sequence set forth as SEQ ID NO: 5. In other embodiments, a VP7 polypeptide is provided that includes an amino acid sequence at least about 98.9% identical, at least about 99.0% identical, at least about 99.1% identical, at least about 99.2% identical, at least about 99.3% identical, at least about 99.4% identical, at least about 99.5% identical, at least about 99.6% identical, at least 99.7% identical, at least 99.8% identical, or at least about 99.9% identical, to the amino acid sequence set forth as SEQ ID NO: 6. In a specific non-limiting example, the VP7 polypeptide includes or consists of the amino acid sequence set forth as SEQ ID NO: 6. One or more of these polypeptides, or immunogenic fragments thereof, can be included in a pharmaceutical composition. In specific non-limiting examples, the composition includes VP4, VP7, or both VP4 and VP7. Also provided are polypeptides that include at most 1, 2, 3, 4, 5, 6, 7, 8, 9 or 10 conservative amino acid substitutions in the amino acid sequences set forth as SEQ ID NOs: 1-6.

In other embodiments, a NSP1 polypeptide is provided that includes an amino acid sequence at least about 98.9% identical, at least about 99.0% identical, at least about 99.1% identical, at least about 99.2% identical, at least about 99.3% identical, at least about 99.4% identical, at least about 99.5% identical, at least about 99.6% identical, at least 99.7% identical, at least 99.8% identical, or at least about 99.9% identical, to the amino acid sequence set forth as SEQ ID NO: 7. In a specific non-limiting example, the NSP1 polypeptide includes or consists of the amino acid sequence set forth as SEQ ID NO: 7. In other embodiments, a NSP2 polypeptide is provided that includes or consists of the amino acid sequence set forth as SEQ ID NO: 8. In other embodiments, a NSP3 polypeptide is provided that includes or consists of an amino acid sequence at least about 99.8% identical, or at least about 99.9% identical, to the amino acid sequence set forth as SEQ ID NO: 9. In a specific non-limiting example, the NSP3 polypeptide includes or consists of the amino acid sequence set forth as SEQ ID NO: 9. In other embodiments, a NSP4 polypeptide is provided that includes or consists of the amino acid sequence set forth as SEQ ID NO: 10. In other embodiments, a NSP5 polypeptide is provided that includes an amino acid sequence at least about 99.6% identical, about 99.7% identical, about 99.8% identical, or at least about 99.9% identical, to the amino acid sequence set forth as SEQ ID NO: 11. In a specific non-limiting example, the VP3 polypeptide includes or consists of the amino acid sequence set forth as SEQ ID NO: 11. Also provided are polypeptides that include at most 1, 2, 3, 4, 5, 6, 7, 8, 9 or 10 conservative amino acid substitutions in the amino acid sequences set forth as SEQ ID NOs: 7-11.

One or more of these polypeptides, or fragments thereof, can be included in a pharmaceutical composition.

In some embodiments, a nucleic acid molecule is disclosed encoding a VP1 polypeptide including an amino acid sequence at least about 99.8% identical, or at least about 99.9% identical, to the amino acid sequence set forth as SEQ ID NO: 1. In a specific non-limiting example, the nucleic acid molecule encodes a VP1 polypeptide comprising the amino acid sequence set forth as SEQ ID NO: 1. In additional embodiments, the nucleic acid molecule is at least about 99.7% identical, at least about 99.8% identical, or at least about 99.9% identical, to the nucleic acid sequence set forth as SEQ ID NO: 12. In a specific non-limiting example, the nucleic acid molecule includes or consists of the nucleic acid sequence set forth as SEQ ID NO: 12.

In some embodiments, a nucleic acid molecule is disclosed encoding a VP2 polypeptide comprising the amino acid sequence set forth as SEQ ID NO: 2. In additional embodiments, the nucleic acid molecule is at least about 99.5% identical, at least about 99.6% identical, at least about 99.7% identical, at least about 99.8% identical, or at least about 99.9% identical to the nucleic acid sequence set forth as SEQ ID NO: 13. In a specific non-limiting example, embodiments, the nucleic acid molecule includes or consists of the nucleic acid sequence set forth as SEQ ID NO: 13.

In some embodiments, a nucleic acid molecule is disclosed encoding a VP3 polypeptide is disclosed that includes an amino acid sequence at least about 99.6% identical, at least 99.7% identical, at least 99.8% identical, or at least about 99.9% identical, to the amino acid sequence set forth as SEQ ID NO: 3. In a specific non-limiting example, the nucleic acid molecule includes a nucleic acid sequence encoding a VP3 polypeptide comprising the amino acid sequence set forth as SEQ ID NO: 3. In additional embodiments, the nucleic acid sequence is at least about 99.4% identical, about 99.5% identical, about 99.6% identical, about 99.7% identical, at least about 99.8% identical, or at least about 99.9% identical, to the nucleic acid sequence set forth as SEQ ID NO: 14. In a specific non-limiting example, the nucleic acid molecule includes or consists of the nucleic sequence set forth as SEQ ID NO: 14.

In some embodiments, a nucleic acid molecule is disclosed that encodes a VP4 polypeptide comprising an amino acid sequence at least about 99.1% identical, at least about 99.2% identical, at least about 99.3% identical, at least about 99.4% identical, at least about 99.5% identical, at least about 99.6% identical, at least 99.7% identical, at least 99.8% identical, or at least about 99.9% identical, to the amino acid sequence set forth as SEQ ID NO: 4. In a specific non-limiting example, the nucleic acid molecule includes a nucleic acid sequence encoding a VP4 polypeptide comprising the amino acid sequence set forth as SEQ ID NO: 4. In additional embodiments, the nucleic acid molecule includes a nucleic acid sequence at least about 99.2% identical, at least about 99.3% identical, at least about 99.4% identical, about 99.5% identical, about 99.6% identical, about 99.7% identical, at least about 99.8% identical, or at least about 99.9% identical, to the nucleic acid sequence set forth as SEQ ID NO: 15. In a specific non-limiting example, the nucleic acid molecule includes or consists of the nucleic sequence set forth as SEQ ID NO: 15.

In some embodiments, a nucleic acid molecule is disclosed encoding a VP6 polypeptide comprising the amino acid sequence set forth as SEQ ID NO: 5. In additional embodiments, the nucleic acid molecule includes a nucleic acid sequence at least about 99.7% identical, at least about 99.8% identical, or at least about 99.9% identical to the nucleic acid sequence set forth as SEQ ID NO: 16. In a specific non-limiting example, embodiments, the rotavirus includes or consists of the nucleic acid sequence set forth as SEQ ID NO: 16.

In some embodiments, a nucleic acid molecule is disclosed encoding a VP7 polypeptide comprising an amino acid sequence at least about 98.9% identical, at least about 99.0% identical, at least about 99.1% identical, at least about 99.2% identical, at least about 99.3% identical, at least about 99.4% identical, at least about 99.5% identical, at least about 99.6% identical, at least 99.7% identical, at least 99.8% identical, or at least about 99.9% identical, to the amino acid sequence set forth as SEQ ID NO: 6. In a specific non-limiting example, the nucleic acid molecule encodes a VP7 polypeptide comprising the amino acid sequence set forth as SEQ ID NO: 6. In additional embodiments, nucleic acid molecule includes a nucleic acid sequence at least about 99.4% identical, about 99.5% identical, about 99.6% identical, about 99.7% identical, at least about 99.8% identical, or at least about 99.9% identical, to the nucleic acid sequence set forth as SEQ ID NO: 17. In a specific non-limiting example, the nucleic acid molecule includes or consists of the nucleic sequence set forth as SEQ ID NO: 17.

In some embodiments, a nucleic acid molecule is disclosed encoding a NSP1 polypeptide comprising an amino acid sequence at least about 98.9% identical, at least about 99.0% identical, at least about 99.1% identical, at least about 99.2% identical, at least about 99.3% identical, at least about 99.4% identical, at least about 99.5% identical, at least about 99.6% identical, at least 99.7% identical, at least 99.8% identical, or at least about 99.9% identical, to the amino acid sequence set forth as SEQ ID NO: 7. In a specific non-limiting example, the nucleic acid molecule includes a nucleic acid sequence encoding a NSP1 polypeptide comprising the amino acid sequence set forth as SEQ ID NO: 7. In additional embodiments, the nucleic acid molecule includes a nucleic acid sequence at least about at least about 99.2% identical, at least 99.3% identical, at least 99.4% identical, about 99.5% identical, about 99.6% identical, about 99.7% identical, at least about 99.8% identical, or at least about 99.9% identical, to the nucleic acid sequence set forth as SEQ ID NO: 18. In a specific non-limiting example, the nucleic acid molecule includes or consists of the nucleic sequence set forth as SEQ ID NO: 18.

In some embodiments, a nucleic acid molecule is disclosed encoding a NSP2 polypeptide comprising the amino acid sequence set forth as SEQ ID NO: 8. In additional embodiments, the nucleic acid molecule includes a NSP2 nucleic acid sequence at least about 99.8% identical, or at least about 99.9% identical to the nucleic acid sequence set forth as SEQ ID NO: 19. In a specific non-limiting example, embodiments, the nucleic acid molecule includes or consists of the nucleic acid sequence set forth as SEQ ID NO: 19.

In some embodiments, a nucleic acid molecule is disclosed encoding a NSP3 polypeptide comprising an amino acid sequence at least about 99.8% identical, or at least about 99.9% identical, to the amino acid sequence set forth as SEQ ID NO: 9 (NSP3). In a specific non-limiting example, the nucleic acid molecule include a nucleic acid sequence encoding a NSP3 polypeptide comprising the amino acid sequence set forth as SEQ ID NO: 9. In additional embodiments, the nucleic acid molecule includes a nucleic acid sequence at least about 99.3% identical, at least about 99.4% identical, at least about 99.5% identical, at least about 99.6% identical, at least 99.7% identical, at least 99.8% identical, or at least about 99.9% identical, to the nucleic acid sequence set forth as SEQ ID NO: 20. In a specific non-limiting example, the nucleic acid molecule includes or consists of the nucleic sequence set forth as SEQ ID NO: 20.

In some embodiments, a nucleic acid molecule is disclosed encoding a NSP4 polypeptide comprising the amino acid sequence set forth as SEQ ID NO: 10. In additional embodiments, nucleic acid molecule includes a nucleic acid sequence at least about 99.2% identical, at least 99.3% identical, at least 99.4% identical, about 99.5% identical, about 99.6% identical, about 99.7% identical, at least about 99.8% identical, or at least about 99.9% identical, to the nucleic acid sequence set forth as SEQ ID NO: 21. In some embodiments, the nucleic acid molecule includes or consist of the nucleic acid sequence set forth as SEQ ID NO: 21.

In some embodiments, a nucleic acid molecule is disclosed encoding a NSPS polypeptide comprising an amino acid sequence at least about 99.6% identical, at least 99.7% identical, at least 99.8% identical, or at least about 99.9% identical, to the amino acid sequence set forth as SEQ ID NO: 11. In a specific non-limiting example, the nucleic acid molecule includes a nucleic acid sequence encoding a NSP5 polypeptide comprising the amino acid sequence set forth as SEQ ID NO: 11. In additional embodiments, the nucleic acid molecule includes a NSP5 nucleic acid sequence at least about 99.6% identical, about 99.7% identical, at least about 99.8% identical, or at least about 99.9% identical, to the nucleic acid sequence set forth as SEQ ID NO: 22. In a specific non-limiting example, the rotavirus includes or consists of the nucleic sequence set forth as SEQ ID NO: 22.

One or more of these polynucleotides, or vectors including one or more of these nucleic acid molecules (e.g., DNA or RNA), can be included in a pharmaceutical composition. In specific non-limiting examples, the polynucleotides in the composition encode VP4, VP7, or both VP4 and VP7.

Vectors comprising any of the nucleic acid molecules disclosed herein, or encoding the proteins and peptides disclosed herein, are provided by the present disclosure, and can be used to transform cells. The vector can be any suitable vector, such as a plasmid vector or a viral vector. In some embodiments, the vector comprises a promoter, an origin of replication and/or a selectable marker. The vector can also encode a reporter. In some examples, the nucleic acid molecule of the vector is operably linked to a promoter. Exemplary promoters include viral promoters, such as cytomegalovirus immediate early gene promoter ("CMV"), herpes simplex virus thymidine kinase ("tk"), SV40 early transcription unit, polyoma, retroviruses, papilloma virus, hepatitis B virus, and human and simian immunodeficiency viruses. Other promoters are isolated from mammalian genes, including the immunoglobulin heavy chain, immunoglobulin light chain, T-cell receptor, HLA DQ α and DQ β, β-interferon, interleukin-2, interleukin-2 receptor, MHC class II, HLA-DRα, β-actin, muscle creatine kinase, prealbumin (transthyretin), elastase I, metallothionein, collagenase, albumin, fetoprotein, β-globin, c-fos, c-HA-ras, insulin, neural cell adhesion molecule (NCAM), α1-antitrypsin, H2B (TH2B) histone, type I collagen, glucose-regulated proteins (GRP94 and GRP78), rat growth hormone, human serum amyloid A (SAA), troponin I (TNI), platelet-derived growth factor, and dystrophin, dendritic cell-specific promoters, such as CD11c, macrophage-specific promoters, such as CD68, Langerhans cell-specific promoters, such as Langerin, and promoters specific for keratinocytes, and epithelial cells of the skin and lung.

In some embodiments, the promoter is inducible. An inducible promoter is a promoter which is inactive or exhibits low activity except in the presence of an inducer substance. Examples of inducible promoters include, but are not limited to, MT II, MMTV, collagenase, stromelysin, SV40, murine MX gene, α-2-macroglobulin, MHC class I gene h-2kb, HSP70, proliferin, tumor necrosis factor, or thyroid stimulating hormone gene promoter. In other embodiments, the promoter is a constitutive promoter that results in high levels of transcription upon introduction into a host cell in the absence of additional factors. Optionally, the transcription control sequences include one or more enhancer elements, which are binding recognition sites for one or more transcription factors that increase transcription above that observed for the minimal promoter alone.

It may be desirable to include a polyadenylation signal to effect proper termination and polyadenylation of the gene transcript. Exemplary polyadenylation signals have been isolated from bovine growth hormone, SV40 and the herpes simplex virus thymidine kinase genes. Any of these or other polyadenylation signals can be utilized in the context of the adenovirus vectors described herein.

The vector can be, for example, a viral vector. A number of viral vectors have been constructed, including polyoma, SV40 (Madzak et al., 1992, J. Gen. Virol., 73:15331536), adenovirus (Berkner, 1992, Cur. Top. Microbiol. Immunol., 158:39-6; Berliner et al., 1988, Bio Techniques, 6:616-629; Gorziglia et al., 1992, J. Virol., 66:4407-4412; Quantin et al., 1992, Proc. Nad. Acad. Sci. USA, 89:2581-2584; Rosenfeld et al., 1992, Cell, 68:143-155; Wilkinson et al., 1992, Nucl. Acids Res., 20:2233-2239; Stratford-Perricaudet et al., 1990, Hum. Gene Ther., 1:241-256), vaccinia virus (Mackett et al., 1992, Biotechnology, 24:495-499), adeno-associated virus (Muzyczka, 1992, Curr. Top. Microbiol. Immunol., 158:91-123; On et al., 1990, Gene, 89:279-282), herpes viruses including HSV and EBV (Margolskee, 1992, Curr. Top. Microbiol. Immunol., 158:67-90; Johnson et al., 1992, J. Virol., 66:29522965; Fink et al., 1992, Hum. Gene Ther. 3:11-19; Breakfield et al., 1987, Mol. Neurobiol., 1:337-371; Fresse et al., 1990, Biochem. Pharmacol., 40:2189-2199), Sindbis viruses (H. Herweijer et al., 1995, Human Gene Therapy 6:1161-1167; U.S. Pat. No. 5,091,309 and U.S. Pat. No. 5,2217,879), alphaviruses (S. Schlesinger, 1993, Trends Biotechnol. 11:18-22; I. Frolov et al., 1996, Proc. Natl. Acad. Sci. USA 93:11371-11377) and retroviruses of avian (Brandyopadhyay et al., 1984, Mol. Cell Biol., 4:749-754; Petropouplos et al., 1992, J. Virol., 66:3391-3397), murine (Miller, 1992, Curr. Top. Microbiol. Immunol., 158:1-24; Miller et al., 1985, Mol. Cell Biol., 5:431-437; Sorge et al., 1984, Mol. Cell Biol., 4:1730-1737; Mann et al., 1985, J. Virol., 54:401-407), and human origin (Page et al., 1990, J. Virol., 64:5370-5276; Buchschalcher et al., 1992, J. Virol., 66:2731-2739). Baculovirus (Autographa californica multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif).

Also provided are host cells including these vectors. The host cell can be a eukaryotic cell or a prokaryotic cell. Non-limiting examples of suitable host cells include bacteria, archea, insect, fungi (for example, yeast), plant, and animal cells (for example, mammalian cells, such as human). Exemplary cells of use include *Escherichia coli, Bacillus subtilis, Saccharomyces cerevisiae, Salmonella typhimurium*, SF9 cells, C129 cells, 293 cells, Neurospora, and immortalized mammalian myeloid and lymphoid cell lines. Techniques for the propagation of mammalian cells in culture are well-known (see, Jakoby and Pastan (eds), 1979, Cell Culture. Methods in Enzymology, volume 58, Academic Press, Inc., Harcourt Brace Jovanovich, N.Y.). Examples of commonly used mammalian host cell lines are VERO and HeLa cells, CHO cells, and WI38, BHK, and COS cell lines, although cell lines may be used, such as cells designed to provide higher expression desirable glycosylation patterns, or other features. Techniques for the transformation of yeast cells, such as polyethylene glycol transformation, protoplast transformation and gene guns are also known in the art (see Gietz and Woods Methods in Enzymology 350: 87-96, 2002).

Transformation of a host cell with recombinant DNA can be carried out by conventional techniques as are well known to those skilled in the art. Where the host is prokaryotic, such as, but not limited to, *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation. When the host is a eukaryote, such methods of transfection of DNA as calcium phosphate coprecipitates, conventional mechanical procedures such as microinjection, electroporation, insertion of a plasmid encased in liposomes, or virus vectors can be used.

A number of procedures can be employed when recombinant protein is being purified, such as from a host cell. For example, proteins having established molecular adhesion properties can be reversible fused to the protein. With the appropriate ligand or substrate, a specific protein can be selectively adsorbed to a purification column and then freed from the column in a relatively pure form. The fused protein is then removed by enzymatic activity. Finally, protein could be purified using immunoaffinity columns. Recombinant protein can be purified from any suitable source, include yeast, insect, bacterial, and mammalian cells.

Recombinant proteins can be expressed from recombinant nucleic acids, such as from plasmids, and purified by transformed bacteria in large amounts, typically after promoter induction; but expression can be constitutive. Promoter induction with IPTG is one example of an inducible promoter system. Bacteria are grown according to standard procedures in the art. Fresh or frozen bacteria cells are used for isolation of protein.

Proteins expressed in bacteria can form insoluble aggregates ("inclusion bodies"). Several protocols are suitable for purification of protein inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2-3 passages through a French Press, homogenized using a homignizer, such as Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies can be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation can occur upon removal (by dialysis, for example) or dilution of the denaturant, allowing re-formation of immunologically and/or biologically active protein. Other suitable buffers are known to those skilled in the art. Human proteins are separated from other bacterial proteins by standard separation techniques, e.g., with Ni-NTA agarose resin.

Alternatively, it is possible to purify recombinant protein from bacteria periplasm. After lysis of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM MgSO4 and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

Solubility fractionation can be used as a standard protein separation technique for purifying proteins. As an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

The molecular weight of the protein can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

The protein can also be separated from other proteins on the basis of its size, net surface charge, hydrophobicity, and affinity for ligands or substrates using column chromatography. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Any of the disclosed polypeptides, polynucleotides, and recombinant can be used in immunogenic compositions to elicit an immune response, such as to provide protection against infection by a rotavirus. Thus, the compositions disclosed herein can be used prophylactically or therapeutically. The compositions can be used to produce an immune response in a healthy subject or a subject infected with a rotavirus. The immunogenic composition optionally includes an adjuvant. The disclosed polypeptide or polynucleotides can be included in pharmaceutical compositions, such as those disclosed above.

Further provided is a method of eliciting an immune response to rotavirus in a subject by administering to the subject a therapeutically effective amount of a disclosed polypeptide, or nucleic acid molecule encoding the polypeptide, or an immunogenic composition as disclosed herein. In some embodiments, the subject is administered the recombinant polypeptide, polypeptide or immunogenic composition prophylactically to prevent infection by a rotavirus. In other cases, the disclosed compositions can be used for treating an existing rotavirus infection. Methods for administering immunogenic compositions are disclosed above.

Nucleic acid vaccines encoding a G9P[6] polypeptide, as disclosed herein, can be used to elicit an immune response to treat or prevent a rotavirus infection. Numerous gene delivery techniques are well known in the art, such as those described by Rolland (1998) *Crit. Rev. Therap. Drug Carrier Systems* 15:143-198, and references cited therein. Appropriate nucleic acid expression systems contain the necessary DNA sequences for expression in the patient (such as a suitable promoter and terminating signal). In a preferred embodiment, the DNA can be introduced using a viral expression system (e.g., vaccinia, pox virus, retrovirus, or adenovirus), which can involve the use of a non-pathogenic (defective), replication competent virus. Suitable systems are disclosed, for example, in Fisher-Hoch et al. (1989) *Proc. Natl. Acad. Sci. USA* 86:317-321; Flexner et al. (1989) *Ann. N.Y. Acad. Sci.* 569:86-103; Flexner et al. (1990) *Vaccine* 8:17-21; U.S. Pat. Nos. 4,603,112, 4,769,330, 4,777,127 and 5,017,487; PCT Publication No. WO 89/01973; Great Britain Publication No. 2,200,651; European Publication No. 0,345,242; PCT Publication No. WO 91/02805; Berkner (1988) *Biotechniques* 6:616-627; Rosenfeld et al. (1991) *Science* 252:431-434; Kolls et al. (1994) *Proc. Natl. Acad. Sci. USA* 91:215-219; Kass-Eisler et al. (1993) *Proc. Natl. Acad. Sci. USA* 90:11498-11502; Guzman et al. (1993) *Circulation* 88:2838-2848; and Guzman et al. (1993) *Cir. Res.* 73:1202-1207. Techniques for incorporating DNA into such expression systems are well known to those of ordinary skill in the art. The DNA can also be "naked," as described, for example, in Ulmer et al. (1993) *Science* 259:1745-1749 and reviewed by Cohen (1993) *Science* 259:1691-1692. The uptake of naked DNA can be increased by coating the DNA onto biodegradable beads, which are efficiently transported into the cells. It will be apparent that a vaccine can comprise both a polynucleotide and a polypeptide component. Such vaccines can provide for an enhanced immune response.

Vaccine preparation is generally described in, for example, Powell and Newman, eds., *Vaccine Design* (the subunit and adjuvant approach), Plenum Press (NY, 1995). Vaccines can be designed to generate antibody immunity and/or cellular immunity such as that arising from CTL or CD4+ T cells.

A non-specific immune response enhancer can be any substance that enhances an immune response to an exogenous antigen. Examples of non-specific immune response enhancers include adjuvants, biodegradable microspheres (e.g., polylactic galactide) and liposomes (into which the compound is incorporated; see, e.g., U.S. Pat. No. 4,235,877). Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or IL-2, -7, or -12, can also be used as adjuvants. These are of use in inducing an immune response and can be included in the disclosed compositions.

The disclosure is illustrated by the following non-limiting Examples.

EXAMPLES

Currently licensed monovalent human rotavirus vaccine ROTARIX® (G1P[8]) has showed broad cross-reactive immunity and cross protection against homotypic Wa-like and heterotypic DS-1 like strains among children worldwide. However, this vaccine appears to confer lower efficacy against DS-1 like strains in some regions, a lingering question whether a second strain is needed to provide full protection against all strains. However, DS-1 like strains usually have fastidious growth in cell culture, making it difficult to develop a low cost vaccine. In addition, recent data that some infants with certain histo-blood group antigens (Lewis-negative) who received rotavirus vaccines are still susceptible to P6 rotavirus strains suggest that a vaccine with P6 specificity may add value. Disclosed herein is a G9P[6] strain, designated CDC-6, and its use to induce an immune response.

Example 1

Isolation and Characterization

A G9P[6] strain, designated CDC-6, was isolated from a fecal specimen collected from an infant in the United States by serial passages and plaque purification in cell culture under Good Laboratory Practice conditions. Viral genome was sequenced with Illumina, a next generation sequencing format. Illumina data was analyzed with CLC Genomic Workbench 7. RotaC v2.0 online tool was used for full genotyping. Phylogenetic trees were generated with Mega 5.1 software using neighbor-joining method (1000 bootstrap) and Kimura-2 correction.

Unlike most human rotaviruses, CDC-6 can grow to a titer of $10^7$-$10^8$ ffu/ml in Vero cells and demonstrates strong stability, as evidenced by predominant (>90%) triple-layered particles during upstream production and downstream purification processes. The CDC-6 strain displays a short RNA electropherotype. Full genome analysis revealed its genotype constellation as G9-P[6]-I2-R2-C2-M2-A2-N2-T2-E2-H2, with nine genes (I2-R2-C2-M2-A2-N2-T2-E2-H2) similar to DS-1 like human rotaviruses. The CDC-6 VP4 gene is similar (99.22%) to that of the strain US1205 (G9P[6]) from USA collected in 1996. The CDC-6 VP7 gene is closely related to G9 strain KC268 (99.25%) from USA collected in 1999-2000 and strains (98.87-99.25%) from South Africa collected in 1998-1999, which cluster with circulating G9 strains in lineage III but differ from lineage I (WI61 and F45) or lineage II (116E) strains. The CDC-6 strain possessed favorable virological and molecular features and can be used as a new live oral or an inactivated rotavirus vaccine.

Example 2

Adaptation and Passaging

The virus is passaged as disclosed in U.S. Published Patent Application No. 2015/0079122, incorporated herein by reference. Briefly, one milliliter (ml) of a 10% virus suspension in DMEM is supplemented with neomycin in a 1.7 ml sterile low bind tube, mixed well and then centrifuged for 10 minutes (min) at 3,000 rpm in an Eppendorf micro centrifuge. The supernatant is transferred to a new tube and centrifuged for 10 min at 10,000 rpm (8,000.times.g). The clarified supernatant is sterilized by passing through a 0.45 micron pore filter. The supernatant is tested by EIA (Rotaclone; Meridian Biosciences) and if OD value is >1.0, it is stored at 4° C. before use for infection. Stool extraction and Rotaclone testing can be done the day before infection.

The culture medium is removed from cell monolayers in individual roller tubes. Each roller tube is washed with 2 ml of maintenance medium, then 2 ml maintenance medium is added to each tube and incubated at 37° C. in a rolling apparatus until virus inoculum is ready.

An aliquot of 0.5 ml of supernatant is transferred to a sterile tube and 1 microliter of $CaCl_2$ stock (300 grams per liter) is added to make a final concentration of 800 micrograms per milliliter. The tube is incubated at room temperature for 30 min before adding 3 microliters of porcine trypsin stock (2.5 milligrams per milliliter)—final concentration of 15 micrograms per milliliter. The mixture is incubated for 60 min at 37° C. The same volume of MEM is treated in the same way as a mock inoculum. Separate pipette tips are used for pipetting virus suspension and trypsin solutions. All pipetting of virus is done within a biological safety cabinet.

Medium is removed from each roller tube and 0.2 to 0.3 milliliter of trypsinized virus suspension or mock inoculums is added to each roller tube using separate sterile pipette. The caps are tightened and the tubes incubated at 37° C. on a roller tube apparatus located in an incubator. After 2 hours (hrs) incubation, inoculum is removed using a 1 ml pipette and washed gently with 2 ml maintenance medium.

Two milliliters of maintenance medium containing various concentrations (10, 20 or 30 micrograms per ml depending on strain) of trypsin is added into each tube and incubated for 2 hours at 37° C. on a roller tube apparatus located in an incubator.

The cells are observed daily for cytopathic effect (CPE), harvested at day 4 and stored at −70° C. The cells are subjected to freeze-thaw two times before the next passage.

The freeze-thawed cell lysates are treated with CaC12 and trypsin as described above and subsequent passages are performed as above. The cells are subjected to freeze-thaw at least once and assayed for rotavirus antigen by Rotaclone kit or virus titer is determined by FFA assays.

Example 3

Production and Purification of Rotavirus Strains

Production of rotavirus is accomplished by use of large scale production roller bottles (see U.S. Published Patent Application No. 2015/0079122, incorporated herein by reference). Briefly, Vero cells are cultured in Dulbecco's Modified Eagle Medium (DMEM) supplemented with 5% fetal bovine serum (Invitrogen Corp., Grand Island, N.Y.) and 50 micrograms/milliliter of neomycin (Sigma Corp., St. Louis, Mo.). Confluent monolayers of Vero cells in roller bottles are infected with a particular rotavirus strain at a multiplicity of infection of 0.1.

Rotavirus obtained by large scale production is purified according to procedures known in the art. Briefly described, rotavirus is harvested from infected cultures of Vero cells at four days post-infection. Triple-layered rotavirus particles are purified from supernatants by centrifugation through 40% sucrose cushions in TNC buffer for 2 hours at 106,750.times.g using a SW32Ti rotor and then through isopycnic centrifugations in CsCl gradients for 17 hours at 111,160 g using an SW40Ti rotor. Rotavirus particles can also be purified using sucrose gradients. TNC buffer is 10 mM Tris, pH 8.0, 140 mM NaCl, and 10 mM $CaCl_2$. Purified rotavirus particles are resuspended in diluent buffer which is Hanks Balanced Salt Solution with $CaCl_2$ and $MgCl_2$, obtained from Invitrogen Corp., Grand Island, N.Y., supplemented with 10% sorbitol (Sigma Corp., St. Louis, Mo.). The resuspended isolated rotavirus is stored at −70° C. until it is inactivated and administered to a subject.

Purified rotavirus is analyzed for purity and identity by any of various techniques, illustratively including SDS-PAGE followed by Coomassie blue staining, Western blot using a rotavirus-specific antibody and/or electron microscopy. In addition, purity and identity of purified rotavirus strains is accomplished by identification of particular structural viral proteins.

Example 4

Immunogenicity of Inactivated Rotavirus (IRV)

Immunogenicity of rotavirus strains is tested in a mouse model. Purified killed rotavirus particles are administered intramuscularly to mice without an adjuvant. Animals are immunized with amounts of killed rotavirus protein in the range between 2 and 20 micrograms.

Immunogenicity is assayed by measuring immunoglobulin titers including IgM, IgA and IgG in blood samples obtained at various times after administration. Neutralizing antibody titers are measured by microneutralization assay as described in detail in Jiang, B., Vaccine, 17:1005-1013, 1999, herein by reference. Briefly, mouse sera are serially diluted two-fold in duplicate wells and incubated with trypsin-inactivated RRV rotavirus. Activated rotavirus or similarly treated serum-free MEM medium is incubated in the absence of mouse serum and serve as positive and negative controls, respectively. MA104 cells in MEM medium supplemented with a final concentration of 10 micrograms/milliliter trypsin and 0.5% chick serum, obtained from Invitrogen Corp., Grand Island, N.Y., are added to each well. After incubation at 37° C. for 18 hours, cells are fixed with formalin. Rotavirus antigens in MA104 cells are detected by incubating cells with rabbit anti-RRV hyperimmune serum, HRP-labeled anti-rabbit IgG, and then tetramethyl benzidine. Neutralizing antibody titer in a serum is defined as the reciprocal of the highest dilution giving a 70% reduction in absorbance value compared to that in the virus control.

Antibody titers in mice injected with killed purified rotavirus particles are compared with antibody titers in control mice. Antibody titers in control mice are typically less than 100. Mice are vaccinated intramuscularly (i.m.) twice and rotavirus-specific total (IgA, IgG, and IgM) and neutralizing antibodies are determined by EIA. For total antibody, each serum specimen is tested at an initial dilution of 1:100. Pre-bleed serum specimens have no detectable antibody at this dilution. A value of 20 is used for determining geometric mean titers and illustration. Neutralizing antibody is tested at an initial dilution of 1:20. Antibody titers are expressed as the geometric means for each group (n=7 or 6). Error bars represent 1 standard error.

Example 5

Adjuvant

In a further example, $Al(OH)_3$ is added as an adjutant to rotavirus particles in a vaccine administered to mice. Animals are immunized intramuscularly once with 2 micrograms or 0.2 micrograms of killed purified rotavirus particles in the presence or absence of 600 micrograms $Al(OH)_3$. $Al(OH)_3$ dramatically enhances total antibody titers in mice at both concentrations of rotavirus administered. No antibody titers (less than 100 dilutions) are detected in control mice immunized with 600 micrograms of $Al(OH)_3$.

Example 6

Gnotobiotic Piglet Model

A gnotobiotic piglet model of rotavirus disease is used. This piglet model allows testing under defined conditions avoiding problems of environment exposure of animals and using disease as the outcome variable. This model also allows testing of an inactivated rotavirus vaccine having a G1 serotype against a homotypic Wa challenge. Gnotobiotic piglets are a good animal model for infection and disease with human rotavirus strains. (See Saif L J, et al., Archives of Virology, 1996; 12:S153-61; and Iosef C, et al., Vaccine, 2002; 20:1741-53, both incorporated herein by reference.) The study is designed as disclosed in U.S. Published Patent Application No. 2015/0079122, incorporated herein by reference.

Thirteen infant gnotobiotic piglets are selected and randomly assigned to four groups as indicated in the table below.

| Group Name | Number of Piglets in Group | CDC-6 Antigen (micrograms) | Aluminum hydroxide (micrograms) |
|---|---|---|---|
| AA | 4 | 0 | 600 |
| BB | 4 | 5 | 0 |
| CC | 3 | 5 | 600 |
| DD | 2 | 0 (buffer) | 0 (buffer) |

Each group of animals is kept in separate isolators. Animals in groups BB and CC are vaccinated intramuscularly three times with an inactivated rotavirus vaccine without or with an adjuvant, respectively. The vaccine formulation in this example includes 5 micrograms of killed purified CDC-6 rotavirus in diluent mixed with 600 micrograms of aluminum hydroxide. Animals in groups AA and DD are vaccinated with 600 micrograms of aluminum hydroxide and buffer, respectively, in the same manner. Antigen adsorption is determined by the Bradford method which showed that more than 90% of the antigen was bound to aluminum hydroxide. Both bound and unbound antigen was injected in these immunizations.

As shown in the above table, piglets are immunized with a vaccine formulation including no antigen and 600 micrograms of aluminum hydroxide; 5 micrograms of antigen and no aluminum hydroxide; 5 micrograms of antigen and 600 micrograms of aluminum hydroxide; or no antigen and no aluminum hydroxide (e.g., buffer alone). Each vaccination is carried out by injecting 0.5 milliliters of the vaccine formulation into muscles of the hind legs of the piglets. After three doses of the vaccine formulation administered at intervals of 10-12 days, piglets are orally challenged with virulent rotavirus. Prior to virus challenge, each piglet is inoculated with 3 milliliters of sodium bicarbonate to neutralize acids in the stomach. Fecal specimens are collected from the challenged piglets daily for 10 days. Blood samples are collected throughout the experiment at intervals of 7-14 days. Piglets that are mock vaccinated with aluminum hydroxide only or diluent buffer only all shed rotavirus up to 5 days and at high titer. By contrast, piglets that are vaccinated with inactivated rotavirus without aluminum hydroxide and/or with aluminum hydroxide are protected, as evidenced by complete protection, a shortened 1-day shedding or a delayed and reduced shedding. Piglets vaccinated with antigen develop significant levels of serum IgG. The results show effectiveness of vaccine formulation.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. An isolated polypeptide, comprising an amino acid sequence at least 99.3% identical to the amino acid sequence of SEQ ID NO: 4.

2. The isolated polypeptide of claim 1, comprising the amino acid sequence of SEQ ID NO: 4.

3. An isolated nucleic acid molecule encoding the polypeptide of claim 2.

4. A vector comprising the isolated nucleic acid molecule of claim 1, operably linked to a heterologous promoter.

5. An isolated host cell transformed with the vector of claim 4.

6. A pharmaceutical composition comprising an effective amount of the polypeptide of claim 1, a nucleic acid molecule encoding the polypeptide, or a vector comprising the nucleic acid molecule, and a pharmaceutically acceptable carrier.

7. The pharmaceutical composition of claim 6, further comprising an inactivated G1P[8] rotavirus.

8. The pharmaceutical composition of claim 7, wherein the G1P[8] rotavirus is heat inactivated.

9. The pharmaceutical composition of claim 7, wherein the inactivated G1P[8] rotavirus is CDC-9.

10. The pharmaceutical composition of claim 7, further comprising an adjuvant.

11. A method of inducing an immune response to a rotavirus protein in a subject, comprising administering an effective amount of the pharmaceutical composition of claim 10 to the subject, thereby inducing the immune response to the rotavirus protein in the subject.

12. The method of claim 11, wherein administering the effective amount of the pharmaceutical composition comprises a prime and a boost.

13. The method of claim 11, wherein the subject does not have a rotavirus infection.

14. The method of claim 11, wherein the subject has a rotavirus infection.

15. The method of claim 11, wherein the subject is a human.

16. The method of claim 15, wherein the subject is a) a child of less than 5 years of age or b) a child of less than 1 year of age.

17. The method of claim 11, comprising administering the pharmaceutical composition parenterally to the subject.

18. The method of claim 11, wherein the method further comprises administering an attenuated or inactivated G1P[8] rotavirus to the subject.

19. The method of claim 18, wherein the inactivated G1P[8] rotavirus is heat inactivated.

* * * * *

SEQUENCE LISTING

<160> NUMBER OF SEQ ID NOS: 22

<210> SEQ ID NO 1
<211> LENGTH: 1088
<212> TYPE: PRT
<213> ORGANISM: Rotavirus G9

<400> SEQUENCE: 1

Met Gly Lys Tyr Asn Leu Ile Leu Ser Glu Tyr Leu Ser Phe Ile Tyr
1 5 10 15

Asn Ser Gln Ser Ala Val Gln Ile Pro Ile Tyr Tyr Ser Ser Asn Ser
20 25 30

Glu Leu Glu Ser Arg Cys Ile Glu Phe His Ser Lys Cys Leu Glu Asn
35 40 45

Ser Lys Asn Gly Leu Ser Leu Lys Lys Leu Phe Asn Glu Tyr Ser Asp
50 55 60

Val Ile Glu Asn Ala Thr Leu Leu Ser Ile Leu Ser Tyr Ser Tyr Asp
65 70 75 80

Lys Tyr Asn Ala Val Glu Arg Lys Leu Val Lys Tyr Ala Lys Gly Lys
85 90 95

Pro Leu Glu Ala Asp Leu Thr Val Asn Glu Leu Asp Tyr Glu Asn Asn
100 105 110

Lys Ile Thr Ser Glu Leu Phe Pro Thr Ala Glu Glu Tyr Thr Asp Ser
115 120 125

Leu Met Asp Pro Ala Ile Leu Thr Ser Leu Ser Ser Asn Leu Asn Ala
130 135 140

Val Met Phe Trp Leu Glu Lys His Glu Asn Asp Thr Ala Glu Lys Phe
145 150 155 160

Lys Ile Tyr Lys Arg Arg Leu Asp Leu Phe Thr Ile Val Ala Ser Thr
165 170 175

Val Asn Lys Tyr Gly Val Pro Arg His Asn Ala Lys Tyr Arg Tyr Glu
180 185 190

Tyr Asp Val Met Lys Asp Lys Pro Tyr Tyr Leu Val Thr Trp Ala Asn
195 200 205

Ser Ser Ile Glu Met Leu Met Ser Val Phe Ser His Glu Asp Tyr Leu
210 215 220

Ile Ala Arg Glu Leu Ile Val Leu Ser Tyr Ser Asn Arg Ser Thr Leu
225 230 235 240

Ala Lys Leu Val Ser Ser Pro Met Ser Ile Leu Val Ala Leu Val Asp
245 250 255

Ile Asn Gly Thr Phe Ile Thr Asn Glu Glu Leu Glu Leu Glu Phe Ser
260 265 270

Asn Lys Tyr Val Arg Ala Ile Val Pro Asp Gln Thr Phe Asp Glu Leu
275 280 285

-continued

```
Lys Gln Met Leu Asn Ser Met Arg Lys Ala Gly Leu Val Asp Ile Pro
    290                 295                 300

Lys Met Ile Gln Asp Trp Leu Val Asp Cys Ser Ile Glu Lys Phe Pro
305                 310                 315                 320

Leu Met Ala Lys Ile Tyr Ser Trp Ser Phe His Val Gly Phe Arg Lys
                325                 330                 335

Gln Lys Met Leu Asp Ala Ala Leu Asp Gln Leu Lys Thr Glu Tyr Thr
            340                 345                 350

Glu Asp Val Asp Asp Glu Met Tyr Arg Glu Tyr Thr Met Leu Ile Arg
        355                 360                 365

Asp Glu Val Val Lys Met Leu Glu Glu Ser Val Lys His Asp Asp His
    370                 375                 380

Leu Leu Gln Asp Ser Glu Leu Ala Gly Leu Leu Ser Met Ser Ser Ala
385                 390                 395                 400

Ser Asn Gly Glu Ser Arg Gln Leu Lys Phe Gly Arg Lys Thr Val Phe
                405                 410                 415

Ser Thr Lys Lys Asn Met His Val Met Asp Asp Met Ala Asn Gly Arg
            420                 425                 430

Tyr Thr Pro Gly Ile Ile Pro Pro Val Asn Ala Asp Lys Pro Ile Pro
        435                 440                 445

Leu Gly Arg Arg Asp Val Pro Gly Arg Arg Thr Arg Ile Ile Phe Ile
    450                 455                 460

Leu Pro Tyr Glu Tyr Phe Ile Ala Gln His Ala Val Val Glu Lys Met
465                 470                 475                 480

Leu Ile Tyr Ala Lys His Thr Arg Glu Tyr Ala Glu Phe Tyr Ser Gln
                485                 490                 495

Ser Asn Gln Leu Leu Ser Tyr Gly Asp Val Thr Arg Phe Leu Ser Asn
            500                 505                 510

Asn Ala Met Val Leu Tyr Thr Asp Val Ser Gln Trp Asp Ser Ser Gln
        515                 520                 525

His Asn Thr Gln Pro Phe Arg Lys Gly Ile Ile Met Gly Leu Asp Ile
    530                 535                 540

Leu Ala Asn Met Thr Asn Asp Ala Lys Val Ile Gln Thr Leu Asn Leu
545                 550                 555                 560

Tyr Lys Gln Thr Gln Ile Asn Leu Met Asp Ser Tyr Val Gln Ile Pro
                565                 570                 575

Asp Gly Asn Val Ile Lys Lys Ile Gln Tyr Gly Ala Val Ala Ser Gly
            580                 585                 590

Glu Lys Gln Thr Lys Ala Ala Asn Ser Ile Ala Asn Leu Ala Leu Ile
        595                 600                 605

Lys Thr Val Leu Ser Arg Ile Ser Asn Lys Tyr Ser Phe Ala Thr Lys
    610                 615                 620

Ile Ile Arg Val Asp Gly Asp Asp Asn Tyr Ala Val Leu Gln Phe Asn
625                 630                 635                 640

Thr Glu Val Thr Lys Gln Met Val Gln Asp Val Ser Asn Asp Val Arg
                645                 650                 655

Glu Thr Tyr Ala Arg Met Asn Ala Lys Val Lys Ala Leu Val Ser Thr
            660                 665                 670

Val Gly Ile Glu Ile Ala Lys Arg Tyr Ile Ala Gly Gly Lys Ile Phe
        675                 680                 685

Phe Arg Ala Gly Ile Asn Leu Leu Asn Asn Glu Lys Arg Gly Gln Ser
    690                 695                 700
```

-continued

```
Thr Gln Trp Asp Gln Ala Ala Val Leu Tyr Ser Asn Tyr Ile Val Asn
705                 710                 715                 720

Arg Leu Arg Gly Phe Glu Thr Asp Arg Glu Phe Ile Leu Thr Lys Ile
                725                 730                 735

Met Gln Met Thr Ser Val Ala Ile Thr Gly Ser Leu Arg Leu Phe Pro
            740                 745                 750

Ser Glu Arg Val Leu Thr Thr Asn Ser Thr Phe Lys Val Phe Asp Ser
        755                 760                 765

Glu Asp Phe Ile Ile Glu Tyr Gly Thr Thr Asp Asp Glu Val Tyr Ile
    770                 775                 780

Gln Arg Ala Phe Met Ser Leu Ser Ser Gln Arg Ser Gly Ile Ala Asp
785                 790                 795                 800

Glu Ile Ala Ala Ser Pro Thr Phe Lys Asn Tyr Val Ser Arg Leu Ser
                805                 810                 815

Glu Gln Leu Leu Phe Ser Lys Asn Asn Ile Val Ser Arg Gly Ile Ala
            820                 825                 830

Leu Thr Glu Lys Ala Lys Leu Asn Ser Tyr Ala Pro Ile Ser Leu Glu
        835                 840                 845

Lys Arg Arg Ala Gln Ile Ser Ala Leu Leu Thr Met Leu Gln Lys Pro
    850                 855                 860

Val Thr Phe Lys Ser Asn Lys Ile Thr Ile Asn Asp Ile Leu Lys Asp
865                 870                 875                 880

Ile Lys Pro Phe Phe Thr Val Ser Glu Ala His Leu Pro Ile Gln Tyr
                885                 890                 895

Gln Lys Phe Met Pro Thr Val Pro Glu Asn Val Gln Tyr Ile Ile Gln
            900                 905                 910

Cys Ile Gly Ser Arg Thr Tyr Gln Ile Glu Asp Asp Gly Ser Lys Ser
        915                 920                 925

Ala Ile Ser Arg Leu Ile Ser Lys Tyr Ser Val Tyr Lys Pro Ser Ile
    930                 935                 940

Glu Glu Leu Tyr Lys Val Ile Ser Leu His Glu Asn Glu Ile Gln Leu
945                 950                 955                 960

Tyr Leu Ile Ser Leu Gly Ile Pro Lys Ile Asp Ala Asp Thr Tyr Val
                965                 970                 975

Gly Ser Lys Ile Tyr Ser Gln Asp Lys Tyr Arg Ile Leu Glu Ser Tyr
            980                 985                 990

Val Tyr Asn Leu Leu Ser Ile Asn  Tyr Gly Cys Tyr Gln  Leu Phe Asp
        995                 1000                1005

Phe Asn  Ser Pro Asp Leu Glu  Lys Leu Ile Arg Ile  Pro Phe Lys
    1010                1015                1020

Gly Lys  Ile Pro Ala Val Thr  Phe Ile Leu His Leu  Tyr Ala Lys
    1025                1030                1035

Leu Glu  Val Ile Asn His Ala  Ile Lys Asn Gly Ser  Trp Ile Ser
    1040                1045                1050

Leu Phe  Cys Asn Tyr Pro Lys  Ser Glu Met Ile Lys  Leu Trp Lys
    1055                1060                1065

Lys Met  Trp Asn Ile Thr Ser  Leu Arg Ser Pro Tyr  Thr Asn Ala
    1070                1075                1080

Asn Phe  Phe Gln Asp
    1085

<210> SEQ ID NO 2
<211> LENGTH: 879
<212> TYPE: PRT
```

-continued

<213> ORGANISM: Rotavirus G9

<400> SEQUENCE: 2

```
Met Ala Tyr Arg Lys Arg Gly Ala Arg Arg Glu Ala Asn Leu Asn Asn
1               5                   10                  15

Asn Asp Arg Met Gln Glu Lys Ile Asp Glu Lys Gln Asp Ser Asn Lys
            20                  25                  30

Ile Gln Leu Ser Asp Lys Val Leu Ser Lys Lys Glu Glu Ile Val Thr
        35                  40                  45

Asp Ser His Glu Glu Val Lys Val Thr Asp Glu Leu Lys Lys Ser Thr
    50                  55                  60

Lys Glu Glu Ser Lys Gln Leu Leu Glu Val Leu Lys Thr Lys Glu Glu
65                  70                  75                  80

His Gln Lys Glu Ile Gln Tyr Glu Ile Leu Gln Lys Thr Ile Pro Thr
                85                  90                  95

Phe Glu Pro Lys Glu Thr Ile Leu Arg Lys Leu Glu Asp Ile Lys Pro
            100                 105                 110

Glu Leu Ala Lys Lys Gln Thr Lys Leu Phe Arg Ile Phe Glu Pro Lys
        115                 120                 125

Gln Leu Pro Ile Tyr Arg Ala Asn Gly Glu Arg Glu Leu Arg Asn Arg
    130                 135                 140

Trp Tyr Trp Lys Leu Lys Lys Asp Thr Leu Pro Asp Gly Asp Tyr Asp
145                 150                 155                 160

Val Arg Glu Tyr Phe Leu Asn Leu Tyr Asp Gln Val Leu Thr Glu Met
                165                 170                 175

Pro Asp Tyr Leu Leu Leu Lys Asp Met Ala Val Glu Asn Lys Asn Ser
            180                 185                 190

Arg Asp Ala Gly Lys Val Val Asp Ser Glu Thr Ala Ser Ile Cys Asp
        195                 200                 205

Ala Ile Phe Gln Asp Glu Glu Thr Glu Gly Ala Val Arg Arg Phe Ile
    210                 215                 220

Ala Glu Met Arg Gln Arg Val Gln Ala Asp Arg Asn Val Val Asn Tyr
225                 230                 235                 240

Pro Ser Ile Leu His Pro Ile Asp Tyr Ala Phe Asn Glu Tyr Phe Leu
                245                 250                 255

Gln His Gln Leu Val Glu Pro Leu Asn Asn Asp Ile Ile Phe Asn Tyr
            260                 265                 270

Ile Pro Glu Arg Ile Arg Asn Asp Val Asn Tyr Ile Leu Asn Met Asp
        275                 280                 285

Arg Asn Leu Pro Ser Thr Ala Arg Tyr Ile Arg Pro Asn Leu Leu Gln
    290                 295                 300

Asp Arg Leu Asn Leu His Asp Asn Phe Glu Ser Leu Trp Asp Thr Ile
305                 310                 315                 320

Thr Thr Ser Asn Tyr Ile Leu Ala Arg Ser Val Val Pro Asp Leu Lys
                325                 330                 335

Glu Leu Val Ser Thr Glu Ala Gln Ile Gln Lys Met Ser Gln Asp Leu
            340                 345                 350

Gln Leu Glu Ala Leu Thr Ile Gln Ser Glu Thr Gln Phe Leu Thr Gly
        355                 360                 365

Ile Asn Ser Gln Ala Ala Asn Asp Cys Phe Lys Thr Leu Ile Ala Ala
    370                 375                 380

Met Leu Ser Gln Arg Thr Met Ser Leu Asp Phe Val Thr Thr Asn Tyr
385                 390                 395                 400
```

```
Met Ser Leu Ile Ser Gly Met Trp Leu Leu Thr Val Val Pro Asn Asp
                405                 410                 415

Met Phe Ile Arg Glu Ser Leu Val Ala Cys Gln Leu Ala Ile Val Asn
            420                 425                 430

Thr Ile Ile Tyr Pro Ala Phe Gly Met Gln Arg Met His Tyr Arg Asn
        435                 440                 445

Gly Asp Pro Gln Thr Pro Phe Gln Ile Ala Glu Gln Gln Ile Gln Asn
    450                 455                 460

Phe Gln Val Ala Asn Trp Leu His Phe Val Asn Asn Asn Gln Phe Arg
465                 470                 475                 480

Gln Ala Val Ile Asp Gly Val Leu Asn Gln Val Leu Asn Asp Asn Ile
                485                 490                 495

Arg Asn Gly His Val Ile Asn Gln Leu Met Glu Ala Leu Met Gln Leu
            500                 505                 510

Ser Arg Gln Gln Phe Pro Thr Met Pro Ile Asp Tyr Lys Arg Ser Ile
        515                 520                 525

Gln Arg Gly Ile Leu Leu Leu Ser Asn Arg Leu Gly Gln Leu Val Asp
    530                 535                 540

Leu Thr Arg Leu Leu Ala Tyr Asn Tyr Glu Thr Leu Met Ala Cys Ile
545                 550                 555                 560

Thr Met Asn Met Gln His Val Gln Thr Leu Thr Thr Glu Lys Leu Gln
                565                 570                 575

Leu Thr Ser Val Thr Ser Leu Cys Met Leu Ile Gly Asn Ala Thr Val
            580                 585                 590

Ile Pro Ser Pro Gln Thr Leu Phe His Tyr Tyr Asn Val Asn Val Asn
        595                 600                 605

Phe His Ser Asn Tyr Asn Glu Arg Ile Asn Asp Ala Val Ala Ile Ile
    610                 615                 620

Thr Ala Ala Asn Arg Leu Asn Leu Tyr Gln Lys Lys Met Lys Ala Ile
625                 630                 635                 640

Val Glu Asp Phe Leu Lys Arg Leu Tyr Ile Phe Asp Val Ser Arg Val
                645                 650                 655

Pro Asp Asp Gln Met Tyr Arg Leu Arg Asp Arg Leu Arg Leu Leu Pro
            660                 665                 670

Val Glu Ile Arg Arg Leu Asp Ile Phe Asn Leu Ile Leu Met Asn Met
        675                 680                 685

Asp Gln Ile Glu Arg Ala Ser Asp Lys Ile Ala Gln Gly Val Ile Ile
    690                 695                 700

Ala Tyr Arg Asp Met His Leu Glu Arg Asp Glu Met Tyr Gly Tyr Val
705                 710                 715                 720

Asn Ile Ala Arg Asn Leu Glu Gly Phe Gln Gln Ile Asn Leu Glu Glu
                725                 730                 735

Leu Met Arg Ser Gly Asp Tyr Ala Gln Ile Thr Asn Met Leu Leu Asn
            740                 745                 750

Asn Gln Pro Val Ala Leu Val Gly Ala Leu Pro Phe Ile Thr Asp Ser
        755                 760                 765

Ser Val Ile Ser Leu Ile Ala Lys Leu Asp Ala Thr Val Phe Ala Gln
    770                 775                 780

Ile Val Lys Leu Arg Lys Val Asp Thr Leu Lys Pro Ile Leu Tyr Lys
785                 790                 795                 800

Ile Asn Ser Asp Ser Asn Asp Phe Tyr Leu Val Ala Asn Tyr Asp Trp
                805                 810                 815

Val Pro Thr Ser Thr Thr Lys Val Tyr Lys Gln Val Pro Gln Gln Phe
```

-continued

```
            820                 825                 830

Asp Phe Arg Asn Ser Met His Met Leu Thr Ser Asn Leu Thr Phe Thr
        835                 840                 845

Val Tyr Ser Asp Leu Leu Ala Phe Val Ser Ala Asp Thr Val Glu Pro
    850                 855                 860

Ile Asn Ala Val Ala Phe Asp Asn Met Arg Ile Met Asn Glu Leu
865                 870                 875


<210> SEQ ID NO 3
<211> LENGTH: 835
<212> TYPE: PRT
<213> ORGANISM: Rotavirus G9

<400> SEQUENCE: 3

Met Lys Val Leu Ala Leu Arg His Ser Val Ala Gln Val Tyr Ala Asp
1               5                   10                  15

Thr Gln Val Tyr Thr His Asp Asp Ser Lys Asp Glu Tyr Glu Asn Ala
            20                  25                  30

Phe Leu Ile Ser Asn Leu Thr Thr His Asn Ile Leu Tyr Leu Asn Tyr
        35                  40                  45

Asn Val Lys Thr Leu Gln Ile Leu Asn Lys Ser Gly Ile Ala Ala Val
    50                  55                  60

Glu Ile Gln Lys Ile Asp Glu Leu Phe Thr Leu Ile Arg Cys Asn Phe
65                  70                  75                  80

Thr Tyr Asp Tyr Ile Asp Asp Val Val Tyr Leu His Asp Tyr Ser Tyr
                85                  90                  95

Tyr Thr Asn Asn Glu Ile Arg Thr Asp Gln His Trp Ile Thr Lys Thr
            100                 105                 110

Asn Ile Glu Asp Tyr Leu Leu Pro Gly Trp Lys Leu Thr Tyr Val Gly
        115                 120                 125

Tyr Asn Gly Ser Asp Thr Arg Gly His Tyr Asn Phe Ser Phe Arg Cys
    130                 135                 140

Gln Asn Ala Ala Thr Asp Asp Asp Ala Ile Ile Glu Tyr Ile Tyr Ser
145                 150                 155                 160

Asp Glu Leu Asp Phe Gln Ser Phe Ile Leu Lys Lys Ile Lys Glu Arg
                165                 170                 175

Met Thr Thr Ser Leu Pro Ile Ala Arg Leu Ser Asn Arg Val Phe Arg
            180                 185                 190

Asp Lys Leu Phe Lys Thr Leu Ser Val Asn His Asp Lys Val Val Asn
        195                 200                 205

Ile Gly Pro Arg Asn Glu Ser Met Phe Thr Phe Leu Asp Tyr Pro Ser
    210                 215                 220

Ile Lys Gln Phe Ser Asn Gly Pro Tyr Leu Val Lys Asp Thr Ile Lys
225                 230                 235                 240

Leu Lys Gln Glu Arg Trp Leu Gly Lys Arg Leu Ser Gln Phe Asp Ile
                245                 250                 255

Gly Gln Tyr Lys Asn Met Leu Asn Val Leu Thr Thr Leu Tyr Gln Tyr
            260                 265                 270

Tyr Asp Ile Tyr His Glu Lys Pro Ile Val Tyr Met Ile Gly Ser Ala
        275                 280                 285

Pro Ser Tyr Trp Ile Tyr Asp Val Lys Gln Tyr Ser Asn Leu Lys Phe
    290                 295                 300

Glu Thr Trp Asp Pro Leu Asp Thr Pro Tyr Ser Asn Leu His His Lys
305                 310                 315                 320
```

-continued

```
Glu Leu Phe Tyr Met Asn Asp Val Gln Lys Leu Lys Asp Asn Ser Ile
                325                 330                 335

Leu Tyr Ile Asp Ile Arg Thr Asp Arg Gly Thr Val Asp Trp Lys Glu
            340                 345                 350

Trp Arg Lys Ile Val Glu Arg Gln Thr Ile Asp Asn Leu His Ile Ala
        355                 360                 365

Tyr Lys Tyr Leu Ser Thr Gly Lys Ala Lys Val Cys Cys Val Lys Met
    370                 375                 380

Thr Ala Met Asp Leu Glu Leu Pro Ile Ser Ala Lys Leu Leu His His
385                 390                 395                 400

Pro Thr Thr Glu Ile Arg Ser Glu Phe Tyr Leu Val Met Asp Ile Trp
                405                 410                 415

Asp Ser Lys Asn Ile Lys Arg Phe Ile Pro Lys Gly Val Leu Tyr Ser
            420                 425                 430

Tyr Ile Asn Asn Thr Ile Thr Glu Asn Val Phe Ile Gln Gln Pro Phe
        435                 440                 445

Lys Leu Lys Thr Leu Lys Asn Glu Tyr Ile Ile Ala Leu Tyr Ala Leu
    450                 455                 460

Ser Asn Asp Phe Asn Asn Arg Glu Asp Val Val Lys Leu Ile Asn Asn
465                 470                 475                 480

Gln Lys Lys Ala Leu Met Thr Val Arg Ile Asn Asn Thr Phe Lys Asp
                485                 490                 495

Glu Pro Lys Val Gly Phe Lys Asn Ile Tyr Asp Trp Thr Phe Leu Pro
            500                 505                 510

Thr Asp Phe Glu Thr Asn Gly Ser Ile Ile Thr Ser Tyr Asp Gly Cys
        515                 520                 525

Leu Gly Ile Phe Gly Leu Ser Ile Ser Leu Ala Ser Lys Pro Thr Gly
    530                 535                 540

Asn Asn His Leu Phe Ile Leu Ser Gly Thr Asp Lys Tyr Phe Lys Leu
545                 550                 555                 560

Asp Gln Phe Ala Asn His Met Ser Ile Ser Arg Arg Ser His Gln Ile
                565                 570                 575

Arg Phe Ser Glu Ser Ala Thr Ser Tyr Ser Gly Tyr Ile Phe Arg Asp
            580                 585                 590

Leu Ser Asn Asn Asn Phe Asn Leu Ile Gly Thr Asn Ile Glu Asn Ser
        595                 600                 605

Val Ser Gly His Val Tyr Asn Ala Leu Ile Tyr Tyr Arg Tyr Asn Tyr
    610                 615                 620

Ser Phe Asp Leu Lys Arg Trp Ile Tyr Leu His Ser Thr Gly Lys Ala
625                 630                 635                 640

Ser Ile Glu Gly Gly Lys Tyr Tyr Glu His Ala Pro Ile Glu Leu Ile
                645                 650                 655

Tyr Ala Cys Arg Ser Ala Arg Glu Phe Ala Lys Leu Gln Asp Asp Leu
            660                 665                 670

Thr Val Leu Arg Tyr Ser Asn Glu Ile Glu Asn Tyr Ile Asn Lys Val
        675                 680                 685

Tyr Ser Ile Thr Tyr Ala Asp Asp Pro Asn Tyr Phe Ile Gly Val Lys
    690                 695                 700

Phe Lys Asn Ile Pro Tyr Lys Tyr Asn Val Lys Val Pro His Leu Thr
705                 710                 715                 720

Phe Gly Val Leu Asn Ile Ser Glu Gln Met Leu Pro Asp Val Ile Thr
                725                 730                 735

Ile Leu Lys Arg Phe Lys Asn Glu Leu Phe Gly Met Glu Val Thr Thr
```

```
            740                 745                 750

Ser Tyr Thr Tyr Met Leu Ser Asp Glu Val Tyr Val Ala Asn Ile Ser
        755                 760                 765

Gly Val Leu Ser Thr Tyr Phe Lys Ile Tyr Asn Glu Phe Tyr Lys Glu
    770                 775                 780

Gln Ile Thr Phe Gly Gln Ser Arg Met Phe Ile Pro His Val Thr Leu
785                 790                 795                 800

Ser Phe Ser Asn Glu Lys Thr Val Arg Ile Asp Thr Thr Lys Leu Tyr
                805                 810                 815

Ile Asp Ser Ile Tyr Leu Arg Lys Ile Lys Gly Asp Thr Val Phe Asp
            820                 825                 830

Met Thr Gly
        835


<210> SEQ ID NO 4
<211> LENGTH: 775
<212> TYPE: PRT
<213> ORGANISM: Rotavirus G9

<400> SEQUENCE: 4

Met Ala Ser Leu Ile Tyr Arg Gln Leu Leu Thr Asn Ser Tyr Thr Val
1               5                   10                  15

Glu Leu Ser Asp Glu Ile Asn Thr Ile Gly Ser Glu Lys Ser Gln Asn
            20                  25                  30

Val Thr Ile Asn Pro Gly Pro Phe Ala Gln Thr Asn Tyr Ala Pro Val
        35                  40                  45

Thr Trp Ser His Gly Glu Val Asn Asp Ser Thr Thr Ile Glu Pro Val
    50                  55                  60

Leu Asp Gly Pro Tyr Gln Pro Thr Asn Phe Lys Pro Pro Asn Asp Tyr
65                  70                  75                  80

Trp Ile Leu Leu Asn Pro Thr Asn Gln Gln Val Val Leu Glu Gly Thr
                85                  90                  95

Asn Lys Ile Asp Ile Trp Val Ala Leu Leu Leu Val Glu Pro Asn Val
            100                 105                 110

Thr Asn Gln Ser Arg Gln Tyr Thr Leu Phe Gly Glu Thr Lys Gln Ile
        115                 120                 125

Thr Val Glu Asn Asn Thr Asn Lys Trp Lys Phe Phe Glu Met Phe Arg
    130                 135                 140

Ser Asn Val Ser Ala Glu Phe Gln His Lys Arg Thr Leu Thr Ser Asp
145                 150                 155                 160

Thr Lys Leu Ala Gly Phe Met Lys Phe Tyr Asn Ser Val Trp Thr Phe
                165                 170                 175

Arg Gly Glu Thr Pro His Ala Thr Thr Asp Tyr Ser Ser Thr Ser Asn
            180                 185                 190

Leu Ser Glu Val Glu Thr Val Ile His Val Glu Phe Tyr Ile Ile Pro
        195                 200                 205

Arg Ser Gln Glu Ser Lys Cys Ser Glu Tyr Ile Asn Thr Gly Leu Pro
    210                 215                 220

Pro Met Gln Asn Thr Arg Asn Ile Val Pro Val Ala Leu Ser Ser Arg
225                 230                 235                 240

Ser Val Thr Tyr Gln Arg Ala Gln Val Asn Glu Asp Ile Ile Ile Ser
                245                 250                 255

Lys Thr Ser Leu Trp Lys Glu Met Gln Cys Asn Arg Asp Ile Ile Ile
            260                 265                 270
```

-continued

```
Arg Phe Lys Phe Asn Asn Ser Ile Val Lys Leu Gly Gly Leu Gly Tyr
        275                 280                 285

Lys Trp Ser Glu Ile Ser Phe Lys Ala Ala Asn Tyr Gln Tyr Ser Tyr
    290                 295                 300

Leu Arg Asp Gly Glu Gln Val Thr Ala His Thr Thr Cys Ser Val Asn
305                 310                 315                 320

Gly Val Asn Asn Phe Ser Tyr Asn Gly Gly Ser Leu Pro Thr Asp Phe
                325                 330                 335

Ser Val Ser Arg Tyr Glu Val Ile Lys Glu Asn Ser Tyr Val Tyr Val
            340                 345                 350

Asp Tyr Trp Asp Asp Ser Gln Ala Phe Arg Asn Met Val Tyr Val Arg
        355                 360                 365

Ser Leu Ala Ala Asn Leu Asn Ser Val Lys Cys Ser Gly Gly Thr Tyr
    370                 375                 380

Asn Phe Gln Leu Pro Val Gly Ala Trp Pro Val Met Ser Gly Gly Ala
385                 390                 395                 400

Val Ser Leu His Phe Ala Gly Val Thr Leu Ser Thr Gln Phe Thr Asp
                405                 410                 415

Phe Val Ser Leu Asn Ser Leu Arg Phe Arg Phe Ser Leu Thr Val Glu
            420                 425                 430

Glu Pro Pro Phe Ser Ile Leu Arg Thr Arg Val Ser Gly Leu Tyr Gly
        435                 440                 445

Leu Pro Ala Phe Asn Pro Asn Asp Gly His Glu Tyr Tyr Glu Ile Ala
    450                 455                 460

Gly Arg Phe Ser Leu Ile Ser Leu Val Pro Ser Asn Asp Asp Tyr Gln
465                 470                 475                 480

Thr Pro Ile Met Asn Ser Val Thr Val Arg Gln Asp Leu Glu Arg Gln
                485                 490                 495

Leu Gly Asp Leu Arg Glu Glu Phe Asn Ser Leu Ser Gln Glu Ile Ala
            500                 505                 510

Met Thr Gln Leu Ile Asp Leu Ala Leu Leu Pro Leu Asp Met Phe Ser
        515                 520                 525

Met Phe Ser Gly Ile Lys Ser Thr Ile Asp Val Ala Lys Ser Met Val
    530                 535                 540

Thr Lys Val Met Lys Lys Phe Lys Lys Ser Gly Leu Ala Thr Ser Ile
545                 550                 555                 560

Ser Glu Leu Thr Gly Ser Leu Ser Asn Ala Ala Ser Ser Val Ser Arg
                565                 570                 575

Ser Ser Ser Ile Arg Ser Asn Ile Ser Ser Ile Ser Val Trp Thr Asp
            580                 585                 590

Val Ser Glu Gln Ile Ala Gly Ser Ser Asp Ser Val Arg Asn Ile Ser
        595                 600                 605

Thr Gln Thr Ser Ala Ile Ser Lys Arg Leu Arg Leu Arg Glu Ile Thr
    610                 615                 620

Thr Gln Thr Glu Gly Met Asn Phe Asp Asp Ile Ser Ala Ala Val Leu
625                 630                 635                 640

Lys Thr Lys Ile Asp Arg Ser Thr His Ile Ser Pro Asn Thr Leu Pro
                645                 650                 655

Asp Ile Ile Thr Glu Ser Ser Glu Lys Phe Ile Pro Lys Arg Ala Tyr
            660                 665                 670

Arg Val Leu Lys Asp Asp Glu Val Met Glu Ala Asp Val Asp Gly Lys
        675                 680                 685

Phe Phe Ala Tyr Lys Val Gly Thr Phe Glu Glu Val Pro Phe Asp Val
```

-continued

```
    690                 695                 700

Asp Lys Phe Val Asp Leu Val Thr Asp Ser Pro Val Ile Ser Ala Ile
705                 710                 715                 720

Ile Asp Phe Lys Thr Leu Lys Asn Leu Asn Asp Asn Tyr Gly Ile Thr
                725                 730                 735

Arg Ser Gln Ala Leu Asp Leu Ile Arg Ser Asp Pro Arg Val Leu Arg
            740                 745                 750

Asp Phe Ile Asn Gln Asn Asn Pro Ile Ile Lys Asn Arg Ile Glu Gln
        755                 760                 765

Leu Ile Leu Gln Cys Arg Leu
    770                 775


<210> SEQ ID NO 5
<211> LENGTH: 397
<212> TYPE: PRT
<213> ORGANISM: Rotavirus G9

<400> SEQUENCE: 5

Met Asp Val Leu Tyr Ser Leu Ser Lys Thr Leu Lys Asp Ala Arg Asp
1               5                   10                  15

Lys Ile Val Glu Gly Thr Leu Tyr Ser Asn Val Ser Asp Leu Ile Gln
            20                  25                  30

Gln Phe Asn Gln Met Ile Ile Thr Met Asn Gly Asn Glu Phe Gln Thr
        35                  40                  45

Gly Gly Ile Gly Asn Leu Pro Ile Arg Asn Trp Asn Phe Asp Phe Gly
    50                  55                  60

Leu Leu Gly Thr Thr Leu Leu Asn Leu Asp Ala Asn Tyr Val Glu Thr
65                  70                  75                  80

Ala Arg Asn Thr Ile Asp Tyr Phe Val Asp Phe Val Asp Asn Val Cys
                85                  90                  95

Met Asp Glu Met Val Arg Glu Ser Gln Arg Asn Gly Ile Ala Pro Gln
            100                 105                 110

Ser Asp Ser Leu Arg Lys Leu Ser Gly Ile Lys Phe Lys Arg Ile Asn
        115                 120                 125

Phe Asp Asn Ser Ser Glu Tyr Ile Glu Asn Trp Asn Leu Gln Asn Arg
    130                 135                 140

Arg Gln Arg Thr Gly Phe Thr Phe His Lys Pro Asn Ile Phe Pro Tyr
145                 150                 155                 160

Ser Ala Ser Phe Thr Leu Asn Arg Ser Gln Pro Ala His Asp Asn Leu
                165                 170                 175

Met Gly Thr Met Trp Leu Asn Ala Gly Ser Glu Ile Gln Val Ala Gly
            180                 185                 190

Phe Asp Tyr Ser Cys Ala Ile Asn Ala Pro Ala Asn Thr Gln Gln Phe
        195                 200                 205

Glu His Ile Val Gln Leu Arg Arg Val Leu Thr Thr Ala Thr Ile Thr
    210                 215                 220

Leu Leu Pro Asp Ala Glu Arg Phe Ser Phe Pro Arg Val Ile Asn Ser
225                 230                 235                 240

Ala Asp Gly Ala Thr Thr Trp Tyr Phe Asn Pro Val Ile Leu Arg Pro
                245                 250                 255

Asn Asn Val Glu Val Glu Phe Leu Leu Asn Gly Gln Ile Ile Asn Thr
            260                 265                 270

Tyr Gln Ala Arg Phe Gly Thr Ile Val Ala Arg Asn Phe Asp Thr Ile
        275                 280                 285
```

```
Arg Leu Ser Phe Gln Leu Met Arg Pro Pro Asn Met Thr Pro Ser Val
    290                 295                 300

Ala Ala Leu Phe Pro Asn Ala Gln Pro Phe Glu His His Ala Thr Val
305                 310                 315                 320

Gly Leu Thr Leu Lys Ile Glu Ser Ala Val Cys Glu Ser Val Leu Ala
                325                 330                 335

Asp Ala Ser Glu Thr Met Leu Ala Asn Val Thr Ser Val Arg Gln Glu
            340                 345                 350

Tyr Ala Ile Pro Val Gly Pro Val Phe Pro Pro Gly Met Asn Trp Thr
        355                 360                 365

Asp Leu Ile Thr Asn Tyr Ser Pro Ser Arg Glu Asp Asn Leu Gln Arg
    370                 375                 380

Val Phe Thr Val Ala Ser Ile Arg Ser Met Leu Val Lys
385                 390                 395


<210> SEQ ID NO 6
<211> LENGTH: 326
<212> TYPE: PRT
<213> ORGANISM: Rotavirus G9

<400> SEQUENCE: 6

Met Tyr Gly Ile Glu Tyr Thr Thr Ile Leu Thr Phe Leu Ile Ser Ile
1               5                   10                  15

Val Leu Leu Asn Tyr Ile Leu Lys Ser Leu Thr Ser Ala Met Asp Phe
            20                  25                  30

Ile Ile Tyr Arg Phe Leu Leu Leu Ile Val Ile Ala Ser Pro Phe Val
        35                  40                  45

Lys Thr Gln Asn Tyr Gly Ile Asn Leu Pro Ile Thr Gly Ser Met Asp
    50                  55                  60

Thr Ala Tyr Ala Asn Ser Ser Gln Gln Glu Thr Phe Leu Thr Ser Thr
65                  70                  75                  80

Leu Cys Leu Tyr Tyr Pro Thr Glu Ala Ser Thr Gln Ile Gly Asp Thr
                85                  90                  95

Glu Trp Lys Asp Thr Leu Ser Gln Leu Phe Leu Thr Lys Gly Trp Pro
            100                 105                 110

Thr Gly Ser Val Tyr Phe Lys Glu Tyr Thr Asp Ile Ala Ser Phe Ser
        115                 120                 125

Ile Asp Pro Gln Leu Tyr Cys Asp Tyr Asn Val Val Leu Met Lys Tyr
    130                 135                 140

Asp Ser Thr Leu Lys Leu Asp Met Ser Glu Leu Ala Asp Leu Ile Leu
145                 150                 155                 160

Asn Glu Trp Leu Cys Asn Pro Met Asp Ile Thr Leu Tyr Tyr Tyr Gln
                165                 170                 175

Gln Thr Asp Glu Ala Asn Lys Trp Ile Ser Met Gly Gln Ser Cys Thr
            180                 185                 190

Ile Lys Val Cys Pro Leu Asn Thr Gln Thr Leu Gly Ile Gly Cys Ile
        195                 200                 205

Thr Thr Asn Thr Ala Thr Phe Glu Glu Val Ala Thr Asn Glu Lys Leu
    210                 215                 220

Val Ile Thr Asp Val Val Asp Gly Val Asn His Lys Leu Asp Val Thr
225                 230                 235                 240

Thr Asn Thr Cys Thr Ile Arg Asn Cys Lys Lys Leu Gly Pro Arg Glu
                245                 250                 255

Asn Val Ala Ile Ile Gln Val Gly Gly Ser Asp Val Leu Asp Ile Thr
            260                 265                 270
```

```
Ala Asp Pro Thr Thr Ala Pro Gln Thr Glu Arg Met Met Arg Val Asn
        275                 280                 285

Trp Lys Lys Trp Trp Gln Val Phe Tyr Thr Val Val Asp Tyr Ile Asn
    290                 295                 300

Gln Ile Val Gln Val Met Ser Lys Arg Ser Arg Leu Leu Asn Ser Ala
305                 310                 315                 320

Ala Phe Tyr Tyr Arg Val
                325


<210> SEQ ID NO 7
<211> LENGTH: 486
<212> TYPE: PRT
<213> ORGANISM: Rotavirus G9

<400> SEQUENCE: 7

Met Ala Thr Phe Lys Asp Ala Cys Tyr Gln Tyr Lys Lys Leu Asn Lys
1               5                   10                  15

Leu Asn Asn Ala Val Leu Lys Leu Gly Ala Asn Asp Val Trp Arg Pro
            20                  25                  30

Ser Thr Leu Thr Lys Arg Lys Gly Trp Cys Leu Asp Cys Cys Gln His
        35                  40                  45

Thr Asp Leu Thr Tyr Cys Gln Gly Cys Leu Ile Tyr His Val Cys Glu
    50                  55                  60

Trp Cys Ser Gln Tyr Ser Arg Cys Phe Leu Asp Asn Asp Pro His Leu
65                  70                  75                  80

Leu Arg Met Arg Thr Phe Arg Asn Glu Ile Thr Lys Ser Asp Leu Glu
                85                  90                  95

Asn Leu Ile Asn Met Tyr Asp Thr Ser Phe Pro Ile Asn Gln Lys Ile
            100                 105                 110

Val Asn Lys Phe Ala Asn Ala Ile Lys Gln His Lys Cys Arg Asn Glu
        115                 120                 125

Tyr Leu Ile Gln Trp Tyr Asn His Phe Leu Met Pro Ile Thr Leu Gln
    130                 135                 140

Ser Leu Ser Ile Glu Leu Asp Gly Asp Ile Tyr Tyr Ile Phe Gly Tyr
145                 150                 155                 160

Tyr Asp Asp Met His Lys Ile Asn Gln Thr Pro Phe Ser Phe Thr Asn
                165                 170                 175

Leu Ile Ser Lys Tyr Asp Val Leu Leu Leu Asp Ser Ile Asn Phe Asp
            180                 185                 190

Arg Met Ala Phe Leu Pro Leu Thr Leu Gln Gln Glu Tyr Ala Leu Arg
        195                 200                 205

Tyr Phe Ser Lys Ser Arg Phe Ile Thr Glu Arg Arg Lys Cys Ile Glu
    210                 215                 220

Ile Ser His Phe Ser Asp Asn Ile Leu Asn Asp Leu His Asn Pro Asn
225                 230                 235                 240

Phe Thr Leu Gln Val Ile Arg Asn Cys Ser Asn Met Ser Val Glu Trp
                245                 250                 255

Asn Lys Ala Cys Asn Leu Ile Arg Asn Ile Ser Asn Tyr Phe Asp Ile
            260                 265                 270

Phe Lys Ser Ser His Thr Glu Ser Tyr Asn Ile Ser Pro Arg Cys Arg
        275                 280                 285

Val Phe Thr Gln Tyr Lys Leu Lys Ile Ala Ser Lys Leu Ile Lys Pro
    290                 295                 300

Asn Tyr Val Ala Ser Asn His Asn Ser Leu Ala Thr Glu Val His Asn
```

```
305                 310                 315                 320

Cys Lys Trp Cys Ser Ile Asn Asn Asn Ser Ile Val Trp Thr Asp Phe
                325                 330                 335

Arg Ile Lys Asn Val Tyr Asn Asp Ile Phe Asn Phe Ile Arg Ala Leu
            340                 345                 350

Val Lys Ser Asn Leu Tyr Val Gly His Cys Ser Ser Glu Glu Lys Ile
        355                 360                 365

Tyr Glu Ser Ile Lys Asp Ile Leu Asn Val Cys Lys Glu Asn Glu Trp
    370                 375                 380

Asn Met Leu Val Thr Glu Ile Phe Asn Gln Leu Asp Pro Ile Lys Leu
385                 390                 395                 400

Asn Glu Asp Ser Tyr Val Leu Leu Asn Tyr Glu Ile Asn Trp Asn Val
                405                 410                 415

Met Asn Val Leu Ile Asn Ser Ile Gly Lys Val Pro Lys Ile Leu Thr
            420                 425                 430

Leu Ser Asp Val Ile Ser Ile Leu Arg Ile Ile Ile Tyr Asp Trp Phe
        435                 440                 445

Asp Ile Arg Phe Met Arg Asn Thr Pro Met Thr Thr Phe Thr Val Asn
    450                 455                 460

Lys Leu Lys Gln Leu Tyr Glu Lys Asp Arg Thr Ala Glu Tyr Asp Ser
465                 470                 475                 480

Gly Val Ser Asp Val Glu
                485


<210> SEQ ID NO 8
<211> LENGTH: 317
<212> TYPE: PRT
<213> ORGANISM: Rotavirus G9

<400> SEQUENCE: 8

Met Ala Glu Leu Ala Cys Phe Cys Tyr Pro His Leu Glu Asn Asp Ser
1               5                   10                  15

Tyr Lys Phe Ile Pro Phe Asn Asn Leu Ala Ile Lys Cys Met Leu Thr
            20                  25                  30

Ala Lys Val Glu Lys Lys Asp Gln Asp Lys Phe Tyr Asn Ser Ile Ile
        35                  40                  45

Tyr Gly Ile Ala Pro Pro Pro Gln Phe Lys Lys Arg Tyr Asn Thr Asn
    50                  55                  60

Asp Asn Ser Arg Gly Met Asn Tyr Glu Thr Ala Met Phe Asn Lys Val
65                  70                  75                  80

Ala Val Leu Ile Cys Glu Ala Leu Asn Ser Ile Lys Val Thr Gln Ser
                85                  90                  95

Asp Val Ala Ser Val Leu Ser Arg Val Val Ser Val Arg His Leu Glu
            100                 105                 110

Asn Leu Val Leu Arg Arg Glu Asn His Gln Asp Val Leu Phe His Ser
        115                 120                 125

Lys Glu Leu Leu Leu Lys Ser Val Leu Ile Ala Ile Gly His Ser Lys
    130                 135                 140

Glu Ile Glu Thr Thr Ala Thr Ala Glu Gly Gly Glu Ile Val Phe Gln
145                 150                 155                 160

Asn Ala Ala Phe Thr Met Trp Lys Leu Thr Tyr Leu Glu His Lys Leu
                165                 170                 175

Met Pro Ile Leu Asp Gln Asn Phe Ile Glu Tyr Lys Ile Thr Leu Asn
            180                 185                 190
```

```
Glu Asp Lys Pro Ile Ser Glu Ser His Val Lys Glu Leu Ile Ala Glu
        195                 200                 205

Leu Arg Trp Gln Tyr Asn Lys Phe Ala Val Ile Thr His Gly Lys Gly
    210                 215                 220

His Tyr Arg Val Val Lys Tyr Ser Ser Val Ala Asn His Ala Asp Arg
225                 230                 235                 240

Val Tyr Ala Thr Phe Lys Ser Asn Asn Lys Asn Gly Gly Pro Leu Glu
                245                 250                 255

Phe Asn Leu Leu Asp Gln Arg Ile Ile Trp Gln Asn Trp Tyr Ala Phe
            260                 265                 270

Thr Ser Ser Met Lys Gln Gly Asn Ala Leu Asp Val Cys Lys Lys Leu
        275                 280                 285

Leu Phe Gln Lys Met Lys Arg Glu Ser Asn Pro Phe Lys Gly Leu Ser
    290                 295                 300

Thr Asp Arg Lys Met Asp Glu Val Ser Gln Val Gly Ile
305                 310                 315


<210> SEQ ID NO 9
<211> LENGTH: 313
<212> TYPE: PRT
<213> ORGANISM: Rotavirus G9

<400> SEQUENCE: 9

Met Leu Lys Met Glu Ser Thr Gln Gln Met Ala Ser Ser Ile Ile Asn
1               5                   10                  15

Ser Ser Phe Glu Ala Ala Val Val Ala Ala Thr Ser Thr Leu Glu Leu
            20                  25                  30

Met Gly Ile Gln Tyr Asp Tyr Asn Glu Val Tyr Thr Arg Val Lys Ser
        35                  40                  45

Lys Phe Asp Phe Val Met Asp Asp Ser Gly Val Lys Asn Asn Leu Ile
    50                  55                  60

Gly Lys Ala Ala Thr Ile Asp Gln Ala Leu Asn Gly Lys Phe Ser Ser
65                  70                  75                  80

Ser Ile Arg Asn Arg Asn Trp Met Thr Asp Ser Lys Thr Val Ala Arg
                85                  90                  95

Leu Asp Glu Asp Val Asn Lys Leu Arg Leu Leu Leu Ser Ser Lys Gly
            100                 105                 110

Ile Asp Gln Lys Met Arg Val Leu Asn Ala Cys Phe Ser Val Lys Arg
        115                 120                 125

Val Pro Glu Lys Ser Ser Ser Ile Ile Lys Cys Thr Arg Leu Met Lys
    130                 135                 140

Glu Lys Ile Glu Arg Gly Glu Val Glu Val Asp Asp Thr Phe Ile Glu
145                 150                 155                 160

Glu Lys Met Glu Ile Asp Thr Ile Asp Trp Lys Ser Arg Tyr Asp Gln
                165                 170                 175

Leu Glu Arg Arg Phe Glu Ser Leu Lys Gln Arg Val Asn Glu Lys Tyr
            180                 185                 190

Asn Asn Trp Val Ile Lys Ala Arg Lys Ile Asn Glu Asn Met Asn Ser
        195                 200                 205

Leu Gln Asn Val Ile Ser Gln Gln Gln Ala His Ile Asn Glu Leu Gln
    210                 215                 220

Ile Tyr Asn Asp Lys Leu Glu Arg Asp Leu Gln Ser Lys Ile Gly Ser
225                 230                 235                 240

Val Ile Ser Ser Ile Glu Trp Tyr Leu Arg Ser Met Glu Leu Ser Asp
                245                 250                 255
```

Asp Ile Lys Ser Asp Ile Glu Gln Gln Leu Asn Ser Ile Asp His Ile
260 265 270

Asn Pro Val Asn Ala Phe Asp Asp Phe Glu Ser Ile Leu Arg Asn Leu
275 280 285

Ile Ser Asp Tyr Asp Arg Ile Phe Ile Met Phe Lys Gly Leu Leu Gln
290 295 300

Gln Ser Asn Tyr Thr Tyr Thr Tyr Glu
305 310

<210> SEQ ID NO 10
<211> LENGTH: 175
<212> TYPE: PRT
<213> ORGANISM: Rotavirus G9

<400> SEQUENCE: 10

Met Glu Lys Phe Thr Asp Leu Asn Tyr Thr Leu Ser Val Ile Thr Leu
1 5 10 15

Met Asn Ser Thr Leu His Thr Ile Leu Glu Asp Pro Gly Met Ala Tyr
20 25 30

Phe Pro Tyr Ile Ala Ser Val Leu Thr Val Leu Phe Thr Leu His Lys
35 40 45

Ala Ser Ile Pro Thr Met Lys Ile Ala Leu Lys Thr Ser Lys Cys Ser
50 55 60

Tyr Lys Val Val Lys Tyr Cys Ile Val Thr Ile Leu Asn Thr Leu Leu
65 70 75 80

Lys Leu Ala Gly Tyr Lys Glu Gln Ile Thr Thr Lys Asp Glu Ile Glu
85 90 95

Lys Gln Met Asp Arg Val Val Lys Glu Met Arg Arg Gln Leu Glu Met
100 105 110

Ile Asp Lys Leu Thr Thr Arg Glu Ile Glu Gln Val Glu Leu Leu Lys
115 120 125

Arg Ile Tyr Asp Lys Leu Ile Val Arg Ser Thr Asp Glu Ile Asp Met
130 135 140

Thr Lys Glu Ile Asn Gln Lys Asn Val Arg Thr Leu Glu Glu Trp Glu
145 150 155 160

Ser Gly Lys Asn Pro Tyr Glu Pro Lys Glu Val Thr Ala Ala Met
165 170 175

<210> SEQ ID NO 11
<211> LENGTH: 200
<212> TYPE: PRT
<213> ORGANISM: Rotavirus G9

<400> SEQUENCE: 11

Met Ser Leu Ser Ile Asp Val Asn Ser Leu Pro Ser Ile Ser Ser Ser
1 5 10 15

Val Tyr Lys Asn Glu Ser Phe Ser Thr Thr Ser Thr Ile Ser Gly Lys
20 25 30

Ser Ile Gly Arg Ser Glu Gln Tyr Ile Ser Pro Asp Ala Glu Ala Phe
35 40 45

Asn Lys Tyr Met Leu Ser Lys Ser Pro Glu Asp Ile Gly Pro Ser Asp
50 55 60

Ser Ala Ser Asn Asp Pro Leu Thr Ser Phe Ser Ile Arg Ser Asn Ala
65 70 75 80

Val Lys Thr Asn Ala Asp Ala Gly Val Ser Met Asp Ser Ser Ala Gln
85 90 95

-continued

Ser Arg Pro Ser Ser Asp Ile Gly Tyr Asp Gln Met Asp Phe Ser Leu
100 105 110

Asn Lys Gly Ile Lys Ile Asp Ala Thr Met Asp Ser Ser Ile Ser Ile
115 120 125

Ser Thr Thr Ser Lys Lys Glu Lys Ser Lys Gln Glu Asn Lys Asn Lys
130 135 140

Tyr Lys Lys Cys Tyr Pro Lys Ile Glu Ala Glu Ser Asp Ser Asp Glu
145 150 155 160

Tyr Val Leu Asp Asp Ser Asp Ser Asp Asp Gly Lys Cys Lys Asn Cys
165 170 175

Lys Tyr Lys Lys Lys Tyr Phe Ala Leu Arg Leu Arg Met Lys Gln Val
180 185 190

Ala Met Gln Leu Ile Lys Asp Leu
195 200

<210> SEQ ID NO 12
<211> LENGTH: 3302
<212> TYPE: DNA
<213> ORGANISM: Rotavirus G9

<400> SEQUENCE: 12
ggctattaaa gctatacaat ggggaagtat aatctaatct tgtcagaata cttatcattt 60
atatataatt cacaatctgc agttcaaatt ccaatttatt actcttccaa tagtgagttg 120
gaaagtagat gtatagaatt tcattccaaa tgtttagaaa attcaaaaaa tggtctatca 180
ctgaaaaaac tatttaatga atatagtgat gtcattgaga atgctacgtt attatcaata 240
ttatcatact cctacgacaa atataacgcc gttgaacgga aattagtcaa atatgcgaaa 300
ggtaaaccgc ttgaggcaga cctaacggtg aacgaattgg attatgaaaa taataaaata 360
acgtctgagc tgtttccaac agcggaagaa tacaccgact cattgatgga tccagcaatt 420
ctaacttcct tgtcatcaaa tttaaacgca gtcatgtttt ggttggaaaa acacgaaaat 480
gatactgctg aaaaatttaa aatttataaa agaagattag acttattcac tatagtagct 540
tcaaccgtaa acaaatatgg tgtaccaagg cacaatgcaa aatatagata cgaatatgat 600
gtgatgaaag ataaaccata ttacttagtg acatgggcaa attcttcaat tgaaatgcta 660
atgtcagtct tttctcatga agattattta attgcaagag aattgatagt gttgtcatat 720
tctaatagat caactttggc aaaactagta tcatctccaa tgtcaatttt agttgcttta 780
gtggatatta atggaacgtt tattacgaat gaagagttag aattagagtt ttcaaataag 840
tacgtgcggg ccatagtacc agatcaaaca tttgatgaat taaaacagat gcttaacagt 900
atgagaaaag ctggattggt tgatatacct aagatgatac aagactggtt agttgattgt 960
tccatcgaaa aatttccact aatggctaaa atatactcat ggtcgtttca tgttggattc 1020
agaaagcaaa aatgttaga tgctgcctta gaccaattga aaactgagta tacagaagat 1080
gtagatgacg aaatgtatcg tgaatacaca atgctaataa gagatgaagt tgttaaaatg 1140
cttgaagaat cagtaaaaca tgatgaccac ctattacaag attctgaatt agctggtttg 1200
ttgtcaatgt cttcagcatc gaatggagaa tccagacagc ttaaatttgg tagaaaaaca 1260
gttttttcaa ctaaaaagaa catgcatgtt atggatgata tggctaatgg aagatataca 1320
ccaggcataa ttccacctgt aaatgctgat aaaccaatac cgttaggaag aagagacgta 1380
ccaggaagaa gaactagaat aatattcata ttaccgtatg aatattttat agcacagcat 1440
gctgtggttg agaaaatgtt gatctatgca aagcatacta gagaatatgc tgaattctat 1500

-continued tcgcaatcaa atcaactctt atcatacggt gatgttacac gtttcctttc taataatgct 1560
atggtgttat atacagacgt gtctcaatgg gattcatctc aacataatac gcaaccgttt 1620
aggaaaggaa taataatggg attggatata ctagctaaca tgactaatga tgctaaagtt 1680
attcagacat taaatttata taaacaaacg caaattaact tgatggactc atacgttcaa 1740
ataccagatg gtaatgttat taagaaaata cagtatggag ctgtagcatc aggggaaaaa 1800
caaacgaagg cagctaactc tatagcgaat ctggcactaa ttaaaacggt tttatcacgt 1860
atttctaata aatattcatt tgccacaaaa ataataagag ttgacggtga tgataactat 1920
gctgtgctac aatttaatac agaagtaact aaacaaatgg ttcaggatgt ttcgaacgat 1980
gtaagagaaa cttatgcacg aatgaatgct aaagttaaag ctctagtatc cacagtagga 2040
atagaaatag ctaaaagata tattgcagga ggaaaaatat tctttagagc aggaataaat 2100
ttgcttaata atgaaaaaag aggacaaagt acacaatggg atcaggcagc agttttatac 2160
tctaattata tcgtaaacag acttagaggg tttgagactg atagagaatt tattttaact 2220
aaaataatgc aaatgacgtc tgttgctatt actggatcgc taagactttt tccttctgaa 2280
cgtgtattga ctacgaactc tacatttaag gtgtttgatt cagaggattt tattatagag 2340
tatggaacaa ctgatgatga agtatatata cagagagcat tcatgtcttt gtcaagtcag 2400
agatcaggaa tagctgatga aatagccgca tcaccaacat ttaaaaatta tgtgtctaga 2460
ttatcagaac agctactttt ttcaaagaat aatatagtat ctagaggaat agctttgact 2520
gaaaaagcaa agttgaattc atatgcacca atatcacttg aaaaaagacg tgcgcagata 2580
tcagctttgt taacaatgtt gcagaaacca gttaccttca aatcaaacaa aataactata 2640
aacgacatac ttaaagacat aaaaccattt tttacagtaa gcgaagcaca tttgccaata 2700
cagtatcaaa agtttatgcc gaccgtacca gaaaatgtac aatatataat tcagtgtata 2760
gggtcaagaa cttaccagat tgaagatgat ggctcaaaat cagcaatatc ccggcttata 2820
tcaaagtact cagtttataa accgtcgatc gaggaactat ataaagtaat ttcattacat 2880
gagaatgaaa tacaactata tttaatttca ttaggcatac caaaaataga tgctgataca 2940
tatgttggtt caaaaattta ctctcaagat aaatacagga tattggaatc atatgtatat 3000
aacctgttat ccatcaatta cggatgctat caattatttg actttaattc accggacttg 3060
gaaaaattaa ttagaatacc attcaaaggg aagataccag ctgtcacatt tatattacat 3120
ttatatgcta aattagaagt tataaaccat gctattaaga atggttcatg gataagtcta 3180
ttctgtaact atccaaaatc agaaatgata aagttatgga agaaaatgtg gaacattacg 3240
tcgttacgtt cgccatatac caatgcaaat ttctttcaag attagagcgc ttagatgtga 3300
cc 3302

<210> SEQ ID NO 13
<211> LENGTH: 2684
<212> TYPE: DNA
<213> ORGANISM: Rotavirus G9

<400> SEQUENCE: 13
ggctattaaa ggctcaatgg cgtacaggaa acgtggagcg cgccgtgagg cgaacttaaa 60
taataatgat cgaatgcagg agaaaattga tgaaaaacaa gattcaaata aaatacaatt 120
atctgataag gtactttcga agaaagaaga aattgtaacg gatagtcatg aggaagttaa 180
agttactgat gagttaaaaa aatcaacgaa agaagaatca aaacaattgc ttgaagtgtt 240

-continued

```
gaaaacaaag gaagaacatc agaaagaaat acaatatgaa atattacaga aaactatacc    300
aacattcgaa cctaaagaga cgatattgag aaaattagag gatattaaac cagaactagc    360
gaaaaaacag actaagctat ttagaatatt tgaaccgaaa caattaccga tttatagagc    420
aaatggagag agagaattgc gtaatagatg gtattggaaa ttaaaaaaag atacactacc    480
agacggagac tatgatgtga gagagtattt tctgaatttg tatgatcaag tgcttactga    540
aatgccagac tacttattat tgaaagatat ggcagtagaa aataagaatt ctagggatgc    600
aggtaaagtc gttgactcag aaacggctag tatatgcgat gccatatttc aagatgaaga    660
aacggaaggt gccgttagaa gattcattgc agaaatgaga caacgtgtgc aagctgatag    720
aaatgttgtc aattatccat caatattaca tccaatagat tatgcattta atgaatactt    780
tttacaacat caattggttg aaccattgaa taatgatata atatttaatt atataccaga    840
aaggataaga aatgatgtta attatattct caatatggac agaaatttac catcaactgc    900
cagatatata agacctaatt tactgcaaga tagattaaat ttgcacgata attttgaatc    960
actatgggat acaataacta catcaaatta tattttggcg agatcggtag taccagattt   1020
aaaggaatta gtgtcaacgg aagcacaaat tcagaaaatg tcacaagatt tgcaattaga   1080
agcattaaca attcagtcag aaacacaatt tctaacaggt ataaattcac aagcagctaa   1140
cgattgtttt aaaaccttaa ttgcagcaat gttaagtcaa cgtactatgt cattagattt   1200
tgtgactact aattatatgt cattgatttc aggtatgtgg ctattgactg tcgtgccaaa   1260
tgatatgttt ataagggaat cgttagtcgc gtgtcaacta gctatagtaa atacaataat   1320
ctatccagca tttggaatgc aacgaatgca ttatagaaac ggggatccac aaacaccgtt   1380
tcagatagca gaacagcaaa ttcaaaattt ccaagtcgca aattggttac attttgttaa   1440
taataatcaa tttagacagg cagttattga tggtgtattg aatcaggtac tgaatgacaa   1500
tattagaaat ggtcatgtta ttaaccaact gatggaagct ctaatgcagc tgtcgcgaca   1560
acaatttcca accatgccaa ttgattataa gagatcaatt caacgtggaa tattactgtt   1620
atctaacaga cttggtcagt tagttgattt aactagatta ttagcttaca attatgagac   1680
attaatggca tgcattacaa tgaacatgca acatgttcaa accttaacaa cagaaaaatt   1740
acaattaacg tcagttacat cattatgtat gcttattgga aatgcgactg ttataccaag   1800
tccacaaaca ttatttcatt attataacgt taacgttaat tttcattcaa attacaatga   1860
gagaattaat gatgcagtag ctataataac tgctgctaac agactgaatc tatatcagaa   1920
aaaaatgaag gctattgttg aggatttctt aaaaagatta tacatttttg atgtatctag   1980
agttccggac gaccaaatgt atagattaag ggatagatta cgcttattgc cagtagaaat   2040
cagaagattg gatatcttca atctaatact aatgaacatg gatcaaattg aacgtgcctc   2100
agataaaatt gctcaaggtg taatcattgc ttatcgtgac atgcatcttg aaagagatga   2160
gatgtacgga tatgtaaata tagctagaaa tttagaggga tttcaacaga taaatttaga   2220
ggagctgatg agatcaggtg actatgcgca aataactaac atgcttttga ataatcaacc   2280
agtagcattg gttggagcac ttccatttat tactgattca tcagttatat cgctaatagc   2340
aaaacttgac gctacagtgt tcgctcaaat agttaaatta cgaaaagttg atactttaaa   2400
accaatatta tacaagataa attcagactc aaatgacttt tatttagtag ccaattacga   2460
ttgggtgcca acttcgacta caaaagtata caaacaggtt ccgcaacaat ttgattttag   2520
aaattcaatg catatgttaa cttcgaatct tacttttacg gtttattcag atcttctcgc   2580
gttcgtatca gctgacacag tagaacctat aaatgcagtt gcatttgaca atatgcgcat   2640
```

-continued

```
catgaacgaa ttgtagacgc caaccccact gtggagatat gacc                  2684

<210> SEQ ID NO 14
<211> LENGTH: 2591
<212> TYPE: DNA
<213> ORGANISM: Rotavirus G9

<400> SEQUENCE: 14

ggcttttaaa gcaatatcag tagtgtgttt tacctctgat ggtgtaaata tgaaagtatt     60

agctttaaga catagtgtgg ctcaggtgta tgcagacact caggtgtaca cacatgatga    120

ttctaaagat gagtatgaga acgcattctt aatttctaat ctcactacac ataatatatt    180

atatttaaat tataatgtaa aaacgctaca aatattgaat aaatctggta tagctgcagt    240

agagatacag aagatagatg aattattcac gttaattaga tgtaacttta catatgatta    300

cattgatgat gttgtttact tacatgacta ttcatattat actaataatg aaatacggac    360

tgaccaacat tggataacca agacaaatat agaagattat ttattaccag gatggaagct    420

gacatacgtt ggatacaatg gaagtgatac gcgcggacat tataattttt catttagatg    480

tcaaaatgca gctacagatg atgatgcaat aatagagtat atctattcag atgaattaga    540

cttccagagt tttatactca agaagattaa agaaaggatg acaacatcac taccaatagc    600

aagactttca aatcgcgtat ttagagataa gttatttaaa acgttatcag taaatcatga    660

taaagtagtt aatattgggc ccagaaatga atctatgttt actttttag actatccatc    720

aataaaacag ttttcgaatg gaccgtattt agttaaagat acaattaaac tcaaacaaga    780

gagatggctt ggtaaaagat tatcacagtt tgatattggt caatataaga atatgctaaa    840

tgtattaacg actttgtatc aatattacga tatatatcat gaaaaaccaa tcgtatacat    900

gataggatca gcgccctcat attggatata tgacgtcaaa cagtattcta acttgaaatt    960

tgaaacgtgg gatccactag atacaccata ctctaattta catcataagg aattatttta   1020

catgaatgac gtgcaaaaac ttaaagataa ttcaatacta tatatagata taagaacaga   1080

tagaggaact gtagactgga aggaatggcg aaaaatagtg gaaaggcaaa ctattgacaa   1140

tttgcatatt gcatacaaat atctatctac agggaaagct aaggtatgtt gcgttaaaat   1200

gaccgccatg gatttagaat taccgatatc tgcaaaattg cttcaccatc caactacaga   1260

gattagatca gaattttatc tagtgatgga tatatgggac tctaaaaata ttaaaagatt   1320

cataccaaaa ggtgtattat actcatatat aaacaataca attactgaaa acgtattcat   1380

acaacaacct tttaagttga aaacattgaa aaacgaatat ataatagcac tttatgcttt   1440

atcaaatgat tttaacaaca gagaagatgt ggtgaaacta attaataatc agaaaaaagc   1500

gttaatgaca gtgagaatta ataatacgtt taaagatgaa ccaaaagtcg gatttaaaaa   1560

catttacgat tggacatttc taccaacgga ttttgaaact aatggatcaa taattacttc   1620

atatgatggg tgtctaggta tctttggttt atcaatatcg ctagcttcaa aaccaactgg   1680

taataatcat ttgttcattt taagtggaac agacaagtat tttaaactgg atcaatttgc   1740

aaatcatatg agcatatcac gacgatcaca tcagatacga ttttcggagt cagccacttc   1800

atattcggga tatattttta gggatttgtc taataataat ttcaatttaa taggtacgaa   1860

tatagagaat tcagtatccg gacacgtata taatgcattg atttattata gatataatta   1920

ttcatttgac cttaaacgat ggatatactt acattcaaca ggtaaagcta gtattgaagg   1980

tggtaagtat tatgaacatg ctccaattga attgatttat gcatgcagat cagcaagaga   2040
```

-continued

```
atttgcgaaa ctgcaagatg atttaacggt attaagatat tcaaatgaga tagaaaacta   2100

tatcaataaa gtttatagca taacatacgc cgacgatcct aattacttta ttggagttaa   2160

gtttaaaaat attccttata agtataacgt taaagtacca catctcacat ttggcgtgtt   2220

aaatatttct gaacaaatgc taccagatgt aataacgatt ttaaagagat ttaagaatga   2280

gttatttgga atggaagtaa caacgagtta tacgtatatg ttatctgatg aggtgtatgt   2340

agcaaatata agtggtgtac tatcaacata tttcaaaatt tataatgagt tttataaaga   2400

gcaaatcaca tttggacagt caagaatgtt tattcctcat gtaacgttga gttttagtaa   2460

tgagaaaacg gtgagaatag acactacaaa actgtacata gattctattt acttaagaaa   2520

aataaaaggt gacacagtgt ttgatatgac tgggtgagct aaaaacttaa cacactggtc   2580

acgatgtgac c                                                        2591
```

<210> SEQ ID NO 15
<211> LENGTH: 2359
<212> TYPE: DNA
<213> ORGANISM: Rotavirus G9

<400> SEQUENCE: 15

```
ggctataaaa tggcttcgct catttataga cagctactca ctaattcata cacagttgaa     60

ttatcagatg aaattaatac aattggatca gaaaaaagtc aaaatgtaac gattaatccc    120

ggaccgtttg ctcaaacaaa ttatgcacca gtgacttgga gtcatgggga agtgaatgat    180

tcgacaacga tagagccagt actcgatggt ccttatcaac caacaaattt taagccacca    240

aatgattact ggatattatt gaatccaact aatcaacaag ttgtattaga gggtaccaat    300

aaaattgata tttgggttgc tttattactt gttgaaccaa acgtaaccaa tcaaagtaga    360

caatacacat tatttggaga aacgaaacaa attactgtag aaaataacac aaacaaatgg    420

aaattcttcg aaatgttcag aagtaatgtt agtgccgaat ttcaacataa gcgcacttta    480

acatcagaca ctaaattagc tgggtttatg aaattttata atagtgtttg gactttccgc    540

ggtgaaacgc cgcatgctac aactgattac tcgtcaactt caaatttatc tgaagtagaa    600

actgtaatac atgttgagtt ttatataata ccaagatcgc aagaatctaa gtgtagtgaa    660

tacataaata ctggattacc accaatgcag aatacaagga atatagttcc agttgcgtta    720

tcatctaggt cagtgactta tcaacgtgct caggttaatg aggatatcat tatatcaaag    780

acatcgttgt ggaaagaaat gcaatgtaac agagatatta taataaggtt taaatttaat    840

aatagtatag taaaacttgg tgggctaggt tataaatggt cagaaatttc gtttaaagcg    900

gctaattatc agtacagtta cttgcgagat ggagagcaag ttacggcaca tactacttgc    960

tcagttaatg gtgtgaataa cttcagttat aatggaggat cactaccaac tgattttagt   1020

gtatcaagat atgaagtgat taaagagaat tcttatgttt atgttgatta ttgggatgac   1080

tcacaagcat ttaggaacat ggtatatgtc aggtcattgg cagcaaattt aaattcagtg   1140

aagtgtagcg gaggaactta taattttcaa ctaccagttg gtgcatggcc agtgatgagt   1200

ggaggtgcag tgtctttaca tttcgcagga gtcactttat ccactcaatt tactgacttc   1260

gtatcactta attcgttaag atttagattc agtttaaccg ttgaagagcc accgttttca   1320

attttacgta cacgtgtgtc aggattgtac gggctaccag cattcaatcc gaatgacgga   1380

catgaatact atgaaatagc tgggagattt tctcttattt cattagtgcc gtctaatgac   1440

gattatcaaa ctccaatcat gaattcagtt acagtgcgac aagatcttga acgtcaacta   1500

ggtgatttaa gggaggaatt caattcctta tcacaagaaa tagcaatgac gcaattgata   1560
```

-continued gatttagcat tattgccatt agatatgttt tctatgtttt caggtattaa aagcacaatt 1620
gacgtagcca aatcaatggt cacaaaggtg atgaaaaagt ttaagaaatc aggattagct 1680
acatcaatct ctgaattgac tggatcatta tcaaacgctg cttcatcagt ttccagaagt 1740
tcatctatta gatctaacat atcatccata tcagtgtgga cggatgtttc cgaacaaata 1800
gcgggttcgt cagactccgt caggaacatt tccacgcaaa cgtcagctat tagtaaaaga 1860
ttgcgactac gcgaaattac tacacaaact gaaggtatga attttgatga tatttcagcg 1920
gcagttctta aaactaaaat agatagatca actcacataa gcccaaatac attaccagac 1980
ataataactg agtcatctga aaagtttata ccaaaacgag cttatagagt tctaaaagat 2040
gatgaagtga tggaagctga tgtggatggg aagttctttg catataaagt tggcactttt 2100
gaagaagtac catttgacgt agataaattt gttgatttgg taaccgattc tcctgtaatt 2160
tcagctataa ttgattttaa gacgttgaag aatttaaacg acaattatgg tataacgcga 2220
tctcaagcgt tagacttaat cagatctgat cccagagttt tacgcgattt tatcaaccag 2280
aataatccaa ttattaaaaa tagaattgaa cagctaatat tgcaatgtag actgtgagag 2340
ctctatagag gatgtgacc 2359

<210> SEQ ID NO 16
<211> LENGTH: 1356
<212> TYPE: DNA
<213> ORGANISM: Rotavirus G9

<400> SEQUENCE: 16
ggctttaaaa cgaagtcttc aacatggatg tcctgtactc cttatcaaaa actcttaaag 60
atgctagaga caaaattgtc gaaggcacat tatactctaa tgtgagtgat ctaattcaac 120
aatttaacca aatgataatt actatgaatg gaaatgagtt ccaaactgga ggaattggta 180
atctaccaat tagaaattgg aattttgatt ttggattact tggaacaact ctactaaatt 240
tagacgctaa ctacgtcgaa acagcccgta acacaattga ttattttgta gattttgtag 300
ataacgtatg tatggatgaa atggttagag aatcacaaag aaatggaatt gcaccacagt 360
cagactcact tagaaaattg tcaggcatta agttcaaaag gataaatttt gataattcat 420
cggaatatat agagaactgg aatctgcaaa acagaagaca acgaacaggt tttacatttc 480
ataaaccaaa tatttttcct tattcagcgt cattcacact gaatagatca caaccagctc 540
atgataactt gatgggtaca atgtggctga acgcaggatc agaaattcag gtcgctggat 600
tcgactattc gtgtgcaatt aatgcgccag ctaatacaca acaatttgaa catattgtac 660
agctccgaag agttttaact acagctacaa taacactttt accggatgca gaaagattca 720
gttttccaag agtgattaat tcagctgatg gagcaactac atggtatttt aatccagtaa 780
ttcttagacc aaataacgtt gaagtggagt ttctactaaa cgggcagata ataaacactt 840
accaggctag atttggaacg atcgtagcta gaaattttga tacaatcaga ttgtcgtttc 900
agttgatgag accaccaaat atgacaccat cggtagcagc attatttcca aatgcgcaac 960
catttgaaca tcatgctaca gtaggactta cattgaaaat tgaatctgca gtttgtgaat 1020
ctgtacttgc tgacgcaagc gagacaatgc tagcaaatgt gacatctgtt agacaagaat 1080
acgcgatacc agttggacca gtctttccac caggtatgaa ttggactgat ttgatcacta 1140
actattcacc atctagagag gataacttgc agcgtgtatt tacagtggct tccattagaa 1200
gcatgcttgt caaataagga ccaagctaac cacttggtat ccaactttgg tgagtatgta 1260

-continued gctacgtcaa gctgtttgaa ctctgtaagt aaggatgcgc ttacgtattc gctacacaga 1320
gtaatcactc agatgacgta gtgagaggat gtgacc 1356

<210> SEQ ID NO 17
<211> LENGTH: 1061
<212> TYPE: DNA
<213> ORGANISM: Rotavirus G9

<400> SEQUENCE: 17
ggctttaaaa gagagaattt ccgtttggct agcggttagc tccttttaat gtatggtatt 60
gaatatacta caattctaac ctttctgata tcaatagttt tattgaacta tatattaaaa 120
tcactaacta gtgcgatgga ctttataatt tatagatttc ttttacttat tgttattgca 180
tcaccttttg ttaaaacaca aaattatgga attaatttac cgatcactgg ctccatggat 240
acagcatatg caaattcatc acagcaagaa acatttttga cttcaacgct atgcttatat 300
tatcctacag aagcatcaac tcaaattgga gatacggaat ggaaggatac tctgtcccaa 360
ttattcttga ctaaagggtg gccaactgga tcagtctatt ttaaagaata caccgatatc 420
gcttcattct caattgatcc gcaactttat tgtgattata atgttgtact gatgaagtat 480
gattcaacgt taaagctaga tatgtctgaa ttagctgatt taattctaaa tgaatggtta 540
tgtaacccaa tggatataac attatattat tatcagcaaa cagatgaagc gaataaatgg 600
atatcgatgg gacagtcttg taccataaaa gtatgtccat tgaatacgca gactttagga 660
ataggttgta ttaccacaaa tacagcgaca tttgaagagg tggctacaaa tgaaaaatta 720
gtaataaccg atgttgttga tggtgtgaac cataaacttg atgtgactac aaatacctgt 780
acaattagga attgtaagaa gttgggacca agagaaaatg tagcgattat acaagtcggt 840
ggctcagatg tgttagatat tacagcggat ccaactactg caccacaaac tgaacgtatg 900
atgcgagtaa attggaagaa atggtggcaa gttttctata cagtagtaga ttatattaat 960
cagattgtgc aagttatgtc caaaagatca cggttattaa attcagcagc tttttactat 1020
agggtttgat atatcttagg ttagaattgg tcgatgtgac c 1061

<210> SEQ ID NO 18
<211> LENGTH: 1566
<212> TYPE: DNA
<213> ORGANISM: Rotavirus G9

<400> SEQUENCE: 18
ggcttttttt atgaaaagtc ttgtggaagc catggctact tttaaagacg cttgctatca 60
atataaaaaa ttaaacaaat taaataatgc agttttaaag ttaggagcta atgatgtttg 120
gagaccttct actctaacaa aacgtaaagg atggtgctta gattgttgtc aacatacgga 180
cttgacttat tgccaaggat gcttaatata tcatgtttgt gaatggtgta gtcaatatag 240
tagatgcttt cttgataatg atccgcattt actaagaatg cgaactttta gaaatgaaat 300
cacaaagagt gacttagaaa acttaattaa tatgtatgat acatcatttc ctataaatca 360
aaaaatagtt aataagtttg caaacgcaat taaacaacat aaatgtagaa atgagtattt 420
gatacaatgg tataatcatt ttttaatgcc aattacacta cagtctttat caatagaatt 480
agatggagat atatattata tatttggtta ctatgacgat atgcataaaa ttaatcagac 540
tcccttctca ttcacgaatt taattagtaa atatgatgta ttactgctag atagtataaa 600
ttttgacaga atggcatttt taccattaac attacagcaa gagtatgcac ttagatattt 660
ttcaaaatca agatttatta ctgaaagaag gaaatgtatt gaaatttcac atttttcaga 720

-continued

```
taatatatta aatgatttac ataacccgaa ttttacatta caagtgatta gaaattgcag    780

taatatgtca gttgaatgga ataaagcatg taatcttatt agaaatataa gtaattattt    840

cgatatattc aaatcgtcac atactgagtc ttataatata tctcctagat gtagagtatt    900

cacacaatat aaattaaaaa tagcatctaa attaattaaa ccaaattatg tagcatcaaa    960

tcataattcc ttggctactg aagtacacaa ttgcaaatgg tgttcaatta ataataattc   1020

tattgtatgg actgatttca gaattaaaaa tgtttataat gatatattta attttattag   1080

ggctttagtg aaatcaaatc tttacgtggg acattgttct tcagaagaaa agatatatga   1140

atctattaag gatattttaa atgtatgtaa agaaaacgaa tggaacatgt tggtaacgga   1200

aatattcaat caattagatc caataaagct aaatgaggat agctatgttt tgttgaatta   1260

tgaaataaat tggaatgtta tgaatgtatt aattaatagt atcggtaaag taccaaaaat   1320

attaactttg agtgacgtta tttcgatttt acgtataata atatatgatt ggtttgacat   1380

aaggtttatg agaaatactc caatgactac gttcacagtt aataaattaa agcaattata   1440

tgaaaaggat agaactgcag aatatgattc aggtgtatcc gatgttgaat aatttcagag   1500

aaattatgtt cgccaccatg agactctctg cactagagta gcgcctaggc agcataaaat   1560

gtaacc                                                              1566
```

<210> SEQ ID NO 19
<211> LENGTH: 1059
<212> TYPE: DNA
<213> ORGANISM: Rotavirus G9

<400> SEQUENCE: 19

```
ggcttttaaa gcgtctcagt cgccgtttga gccttgcggt gtagccatgg ctgagctagc     60

ttgcttttgc tatccccatt tggagaacga tagctataaa tttattcctt ttaacaattt    120

ggctataaaa tgtatgttga cagcaaaagt agagaaaaaa gatcaggaca aattttacaa    180

ctcgataatc tatggtattg cgccgccgcc acaatttaaa aaacgctata atacaaatga    240

taactcaaga ggaatgaatt atgagactgc aatgtttaac aaagtggcgg tgctaatttg    300

tgaagcactg aattcaatta aagtcacgca gtctgatgtt gcaagtgtac tttcaagagt    360

agtttctgtg agacatcttg agaatttagt attgagaaga gaaaatcatc aggacgttct    420

ttttcactca aaggagctac tactcaaatc agttttaata gctattggtc attcaaagga    480

gattgaaacg actgccactg ctgaaggggg agaaattgtt tttcaaaatg cagcatttac    540

aatgtggaaa ttgacatact tggaacataa actaatgcca attcttgatc aaaactttat    600

tgaatataaa attacattaa atgaagataa accaatttca gagtcacacg taaaagaact    660

tattgctgaa ttacggtggc aatacaataa atttgcagta attacgcatg gtaaaggtca    720

ctatagagtt gtaaaatact cgtcagttgc aaatcacgca gaccgagttt acgctacttt    780

taagagtaat aacaaaaacg gaggtccact agagtttaat ttgcttgacc aaaggataat    840

atggcaaaat tggtacgcat ttacgtcctc aatgaaacaa ggtaatgctc ttgatgtatg    900

caaaaaacta ctcttccaaa aaatgaagcg agaaagtaat ccatttaagg ggctgtcaac    960

tgatagaaaa atggatgaag tttctcaagt aggaatctaa ttcgttatct gtttgaaggt   1020

gggtatggca gagtaagaat tgaaagcgct tatgtgacc                          1059
```

<210> SEQ ID NO 20
<211> LENGTH: 1066
<212> TYPE: DNA

<213> ORGANISM: Rotavirus G9

<400> SEQUENCE: 20

```
ggcttttaat gcttttcagt ggttgatgct caagatggag tctactcagc agatggcatc     60
ttctattatt aactcttctt ttgaagctgc agttgtcgct gcaacttcta cattggaatt    120
aatgggtatt caatatgatt ataatgaagt atatactaga gttaaaagta agtttgattt    180
tgtaatggat gattctggcg ttaagaataa tttaataggt aaagcagcta caattgatca    240
ggctttgaat ggtaagttta gttcatctat cagaaataga aattggatga ctgattcaaa    300
aactgtagca agattagatg aagatgtgaa caaacttaga ttattattgt catcgaaagg    360
aattgatcaa aaaatgagag ttcttaatgc atgctttagt gttaaaagag tacctgaaaa    420
atcgtcatct atcattaaat gtactaggtt aatgaaagag aaaatagaac gtggagaagt    480
cgaagtggat gatacattca ttgaagaaaa aatggaaatt gacactatag attggaaatc    540
cagatatgat caacttgaaa gacgatttga gtcgttaaaa cagcgagtta acgaaaagta    600
caataattgg gttattaagg caaggaaaat aaacgaaaac atgaactctc ttcagaatgt    660
tatttcgcaa caacaagctc atatcaatga attacaaata tataatgata aactagagcg    720
tgatttacaa tcaaaaatag gatcagttat ttcatccatt gaatggtact tacggtctat    780
ggaactatca gatgacatta aatcagatat tgaacaacaa ctcaattcaa tagatcatat    840
taatccagtt aatgcttttg atgattttga gtctattctt cgtaatttaa tatctgatta    900
tgatagaatt tttattatgt ttaaaggatt gttgcagcaa agtaattaca catataccta    960
tgagtaaaca tagcatatta ccatcttcac gtaaccctct atgagcacaa tagttaaaag   1020
ctaacactgt caaaaaccta aatggctata ggggcgttat gtgacc                  1066
```

<210> SEQ ID NO 21
<211> LENGTH: 751
<212> TYPE: DNA
<213> ORGANISM: Rotavirus G9

<400> SEQUENCE: 21

```
ggcttttaaa agttctgttc cgagagagcg cgtgcggaaa gatggaaaag tttaccgacc     60
tcaactacac attgagtgta atcactttaa tgaatagcac attacataca atactagagg    120
atccaggaat ggcgtatttt ccttatattg catctgtcct gacagttttg tttacattac    180
acaaagcgtc aattccaaca atgaaaatag cattgaagac gtcaaaatgt tcgtataaag    240
tagtaaagta ttgcattgtg acaatcctta atacattatt aaagttagca ggttacaaag    300
aacaaattac tactaaagat gaaatagaaa aacaaatgga cagagttgtt aaagaaatga    360
gacgtcaatt agagatgatc gataaactaa ctacacgtga aattgaacaa gtcgaattac    420
ttaaacgcat ctacgataaa ttaatagtgc gatcaactga tgagatagat atgacaaaag    480
aaattaatca aaagaacgta agaacgctag aagagtggga gagcggaaaa aatccttatg    540
aaccaaaaga agtgactgca gcgatgtgag aggttgagct gccgtcgact gtcttcggaa    600
gcggcggagt tctttacagt aaactccatt ggacctgatg gctggctaag aagccatagt    660
cagccatatc gcgtgtggct caagccttaa tcccgtttaa ctaatccggt cagcaccgga    720
cgttaatgga aggaacggtc ttaatgtgac c                                   751
```

<210> SEQ ID NO 22
<211> LENGTH: 816
<212> TYPE: DNA
<213> ORGANISM: Rotavirus G9

-continued

<400> SEQUENCE: 22

```
ggcttttaaa gcgctacagt gatgtctctt agtattgacg tgaatagtct tccttcaatt     60
tcttctagcg tttataaaaa tgaatcgttt tcaacaacgt caactatttc tggaaaatct    120
attggtagga gtgaacagta catttcacca gatgcagaag ctttcaataa gtacatgttg    180
tcaaaatctc cagaagatat tggaccttct gattctgcat cgaacgatcc actcaccagc    240
ttttcgatta gatcgaatgc agttaagaca aatgcagatg ctggcgtgtc tatggattca    300
tcagcacaat cacgaccatc tagcgacatt ggatacgatc aaatggattt ctccttaaat    360
aaaggtatta aaattgatgc tacaatggat tcttcaatat caatatctac tacatcaaag    420
aaggagaaat ctaaacaaga gaacaaaaat aaatataaaa aatgttatcc aaaaattgaa    480
gcagaatctg attctgatga atacgtatta gatgattcag atagtgatga tggaaaatgt    540
aaaaattgca agtataaaaa gaaatatttt gcacttcgtt taagaatgaa acaagttgca    600
atgcaattga ttaaagattt gtgaaaattt tctgattact cttatcatta actgttaaat    660
atttacttat tatacggatg ataagtgttg tttaattata ttatataata gtattattat    720
atcgcgttat tgaatttaac aactttctaa tgagagaaga ttaatgcgtc taccctaaga    780
gatcactagg gagctcccca ctcccgtttt gtgacc                              816
```